(12) United States Patent
Walker

(10) Patent No.: US 9,271,732 B2
(45) Date of Patent: Mar. 1, 2016

(54) MULTI-CHAMBER AUTOMATIC FEED MEDICAL SCREWDRIVER

(76) Inventor: Douglas W. Walker, Ventura, CA (US)

( * ) Notice: Subject to any disclaimer, the term of this patent is extended or adjusted under 35 U.S.C. 154(b) by 655 days.

(21) Appl. No.: 13/609,148

(22) Filed: Sep. 10, 2012

(65) Prior Publication Data

US 2013/0123794 A1     May 16, 2013

Related U.S. Application Data

(63) Continuation of application No. 12/353,363, filed on Jan. 14, 2009, now Pat. No. 8,262,669.

(51) Int. Cl.
*A61B 17/58* (2006.01)
*A61B 17/10* (2006.01)
*A61B 17/86* (2006.01)

(52) U.S. Cl.
CPC ............ *A61B 17/10* (2013.01); *A61B 17/861* (2013.01); *A61B 17/865* (2013.01)

(58) Field of Classification Search
CPC .... B25B 23/065; B25B 23/045; A61B 17/10; A61B 17/105; A61B 17/865
USPC .................................................. 227/137, 138
See application file for complete search history.

(56) References Cited

U.S. PATENT DOCUMENTS

| | | | | |
|---|---|---|---|---|
| 3,812,961 | A * | 5/1974 | Merrick et al. | 206/338 |
| 3,930,297 | A * | 1/1976 | Potucek et al. | 29/431 |
| 3,971,421 | A * | 7/1976 | Damratowski | 81/434 |
| 6,328,746 | B1 * | 12/2001 | Gambale | 606/104 |
| 6,813,977 | B2 * | 11/2004 | Goodhue et al. | 81/433 |
| 7,588,576 | B2 * | 9/2009 | Teague et al. | 606/86 B |
| 8,534,164 | B2 * | 9/2013 | Watt | 81/57.37 |
| 2008/0140086 | A1 * | 6/2008 | Moore et al. | 606/104 |
| 2008/0276761 | A1 * | 11/2008 | Hale et al. | 81/57.37 |

* cited by examiner

*Primary Examiner* — Christian Sevilla
(74) *Attorney, Agent, or Firm* — Koppel, Patrick, Heybl & Philpott

(57) ABSTRACT

A fastener system for placing screws into bone or tissue structure during a medical procedure is disclosed. The fastener system comprises a drive shaft and driver tip that securely and removeably interlocks with the fastener head and drives the fastener into the surgical site, then disengages the fastener and withdraws. The fastener system comprises a multi-chamber cartridge, which can be either reloadable or a pre-loaded disposable one-use unit. Each chamber holds a fastener using one or more of several alignment systems. Example of alignment systems are cantilevers with springs, spring-clips, or molded features within the chamber to hold the fastener in place until the driver tip engages the fastener head. The fastener head also can latch onto the driver tip. As an example, the fastener head can have hooks that lock into a ridge on the driver, and disengage when the driver tip withdraws.

19 Claims, 69 Drawing Sheets

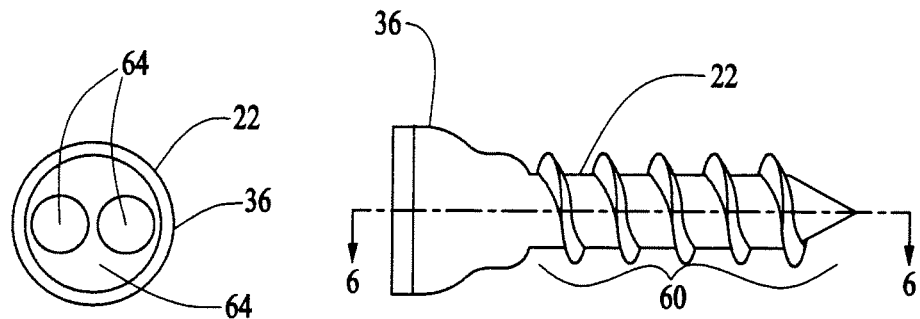
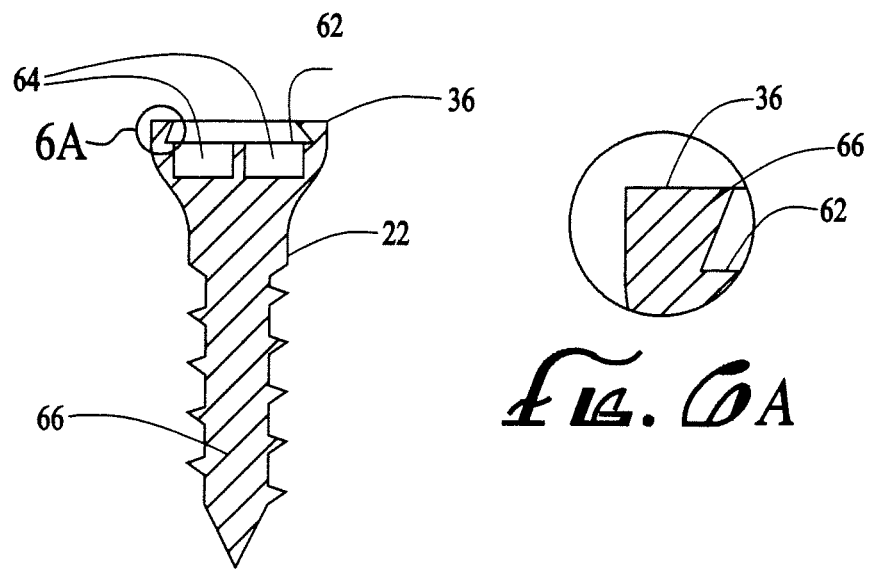

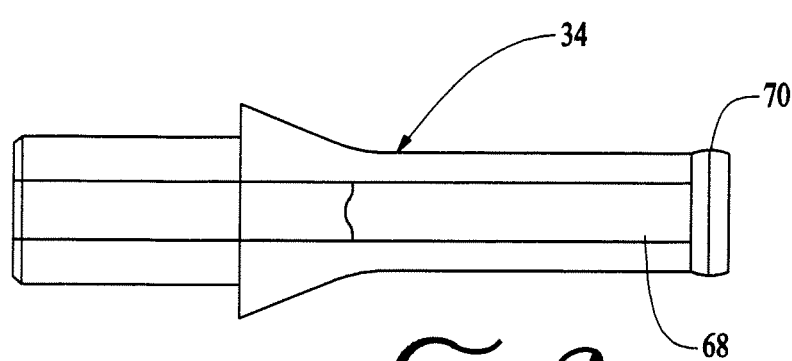
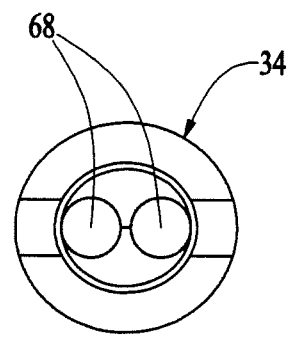
fig. 8        fig. 9
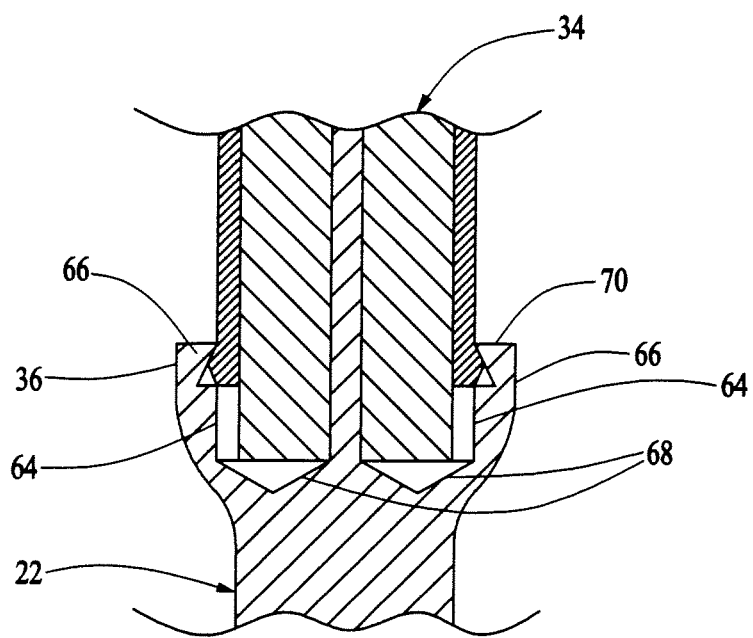
fig. 30

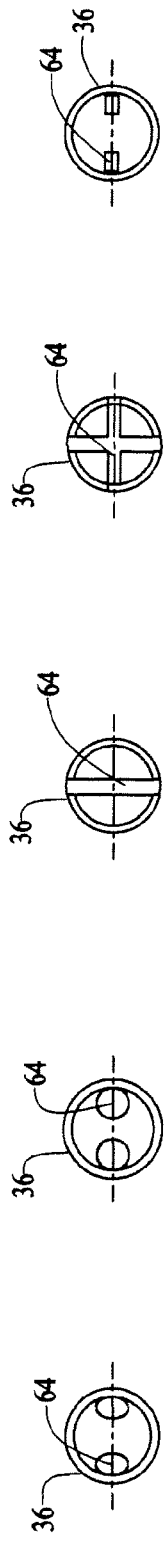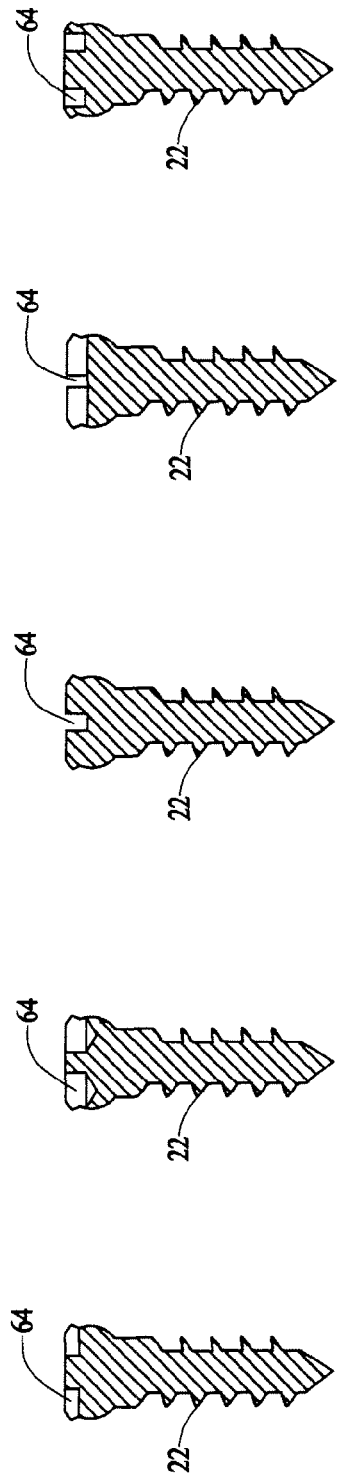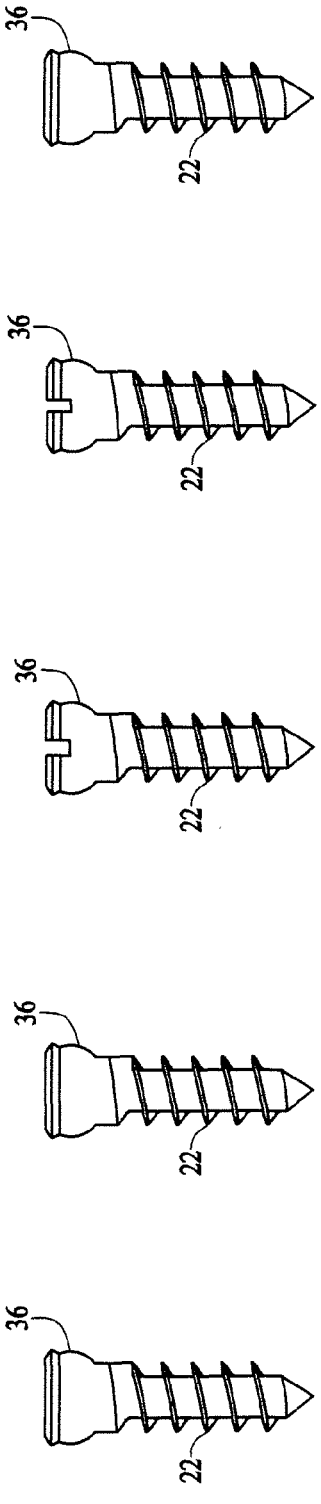

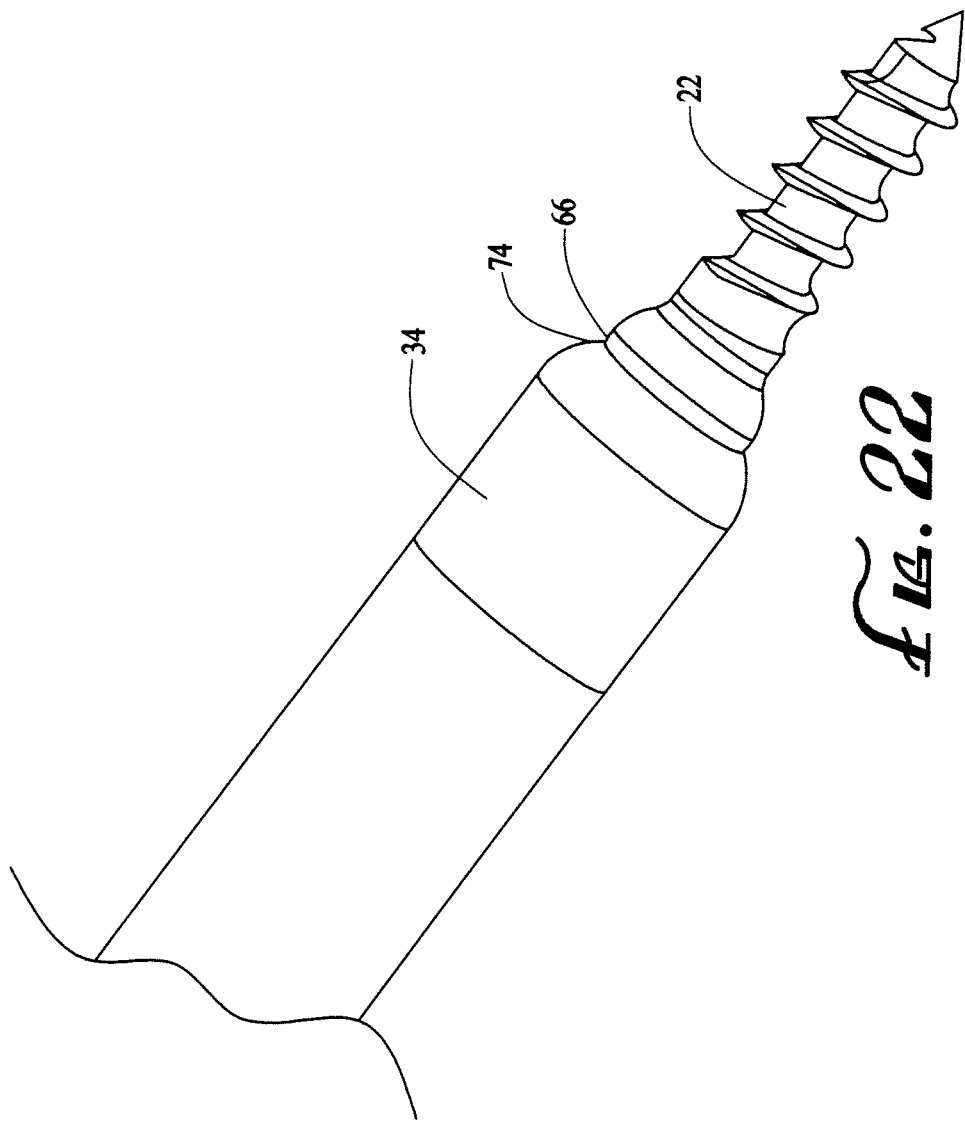

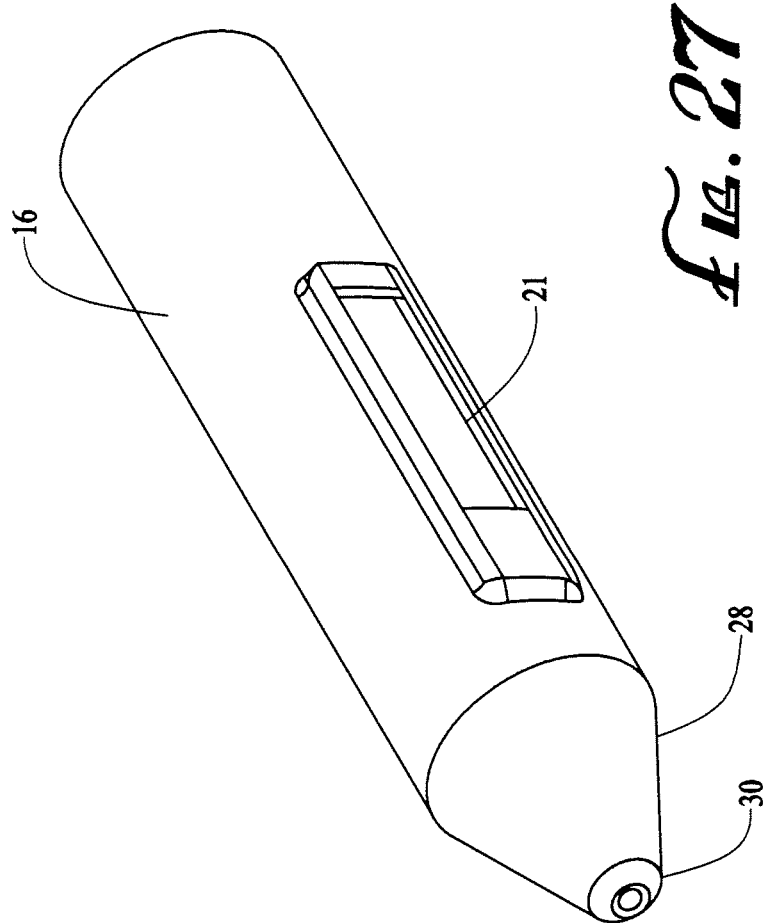

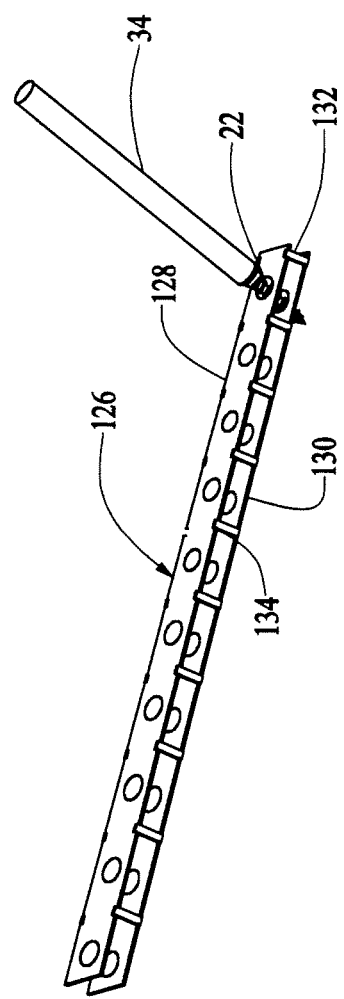

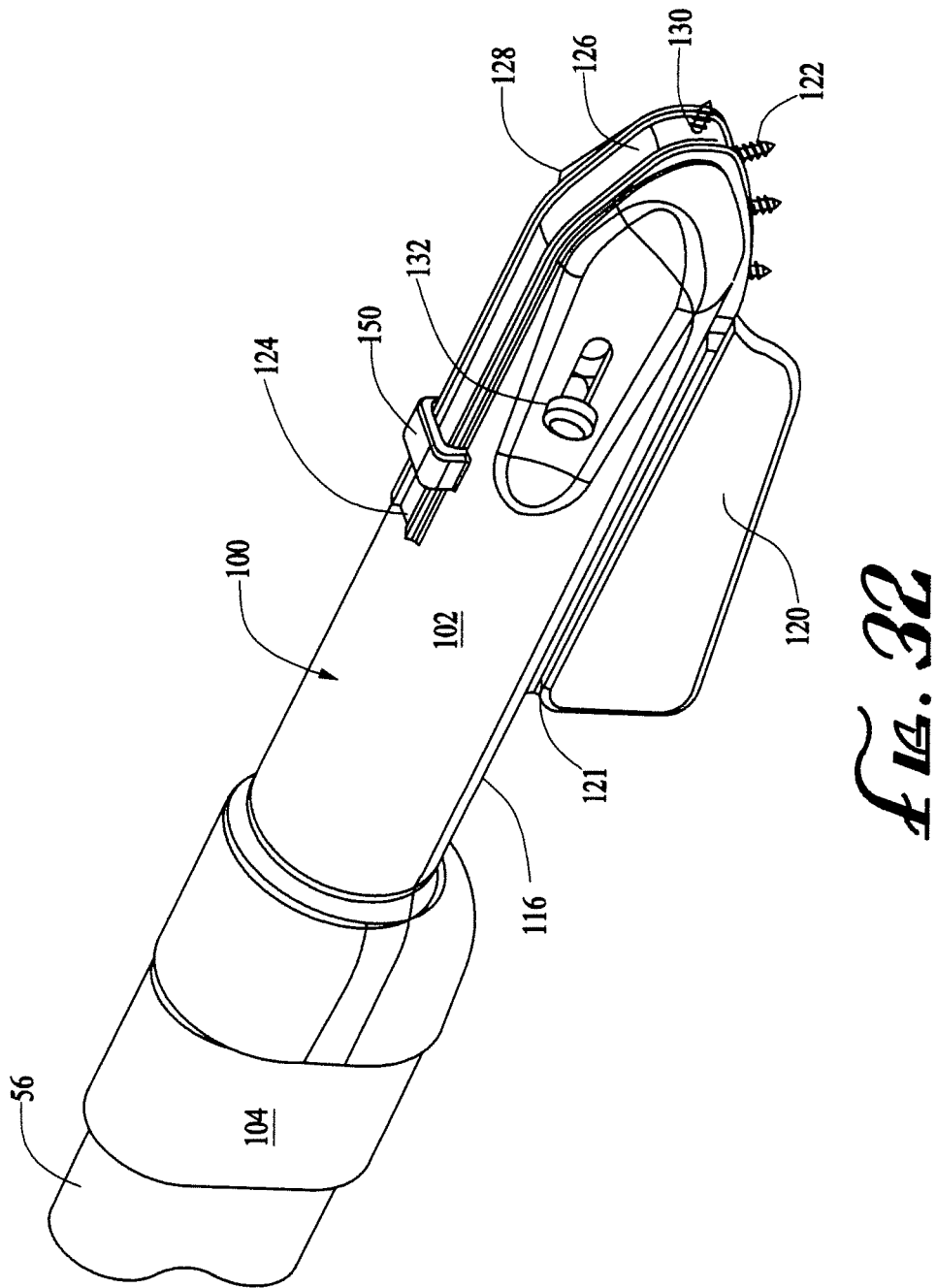

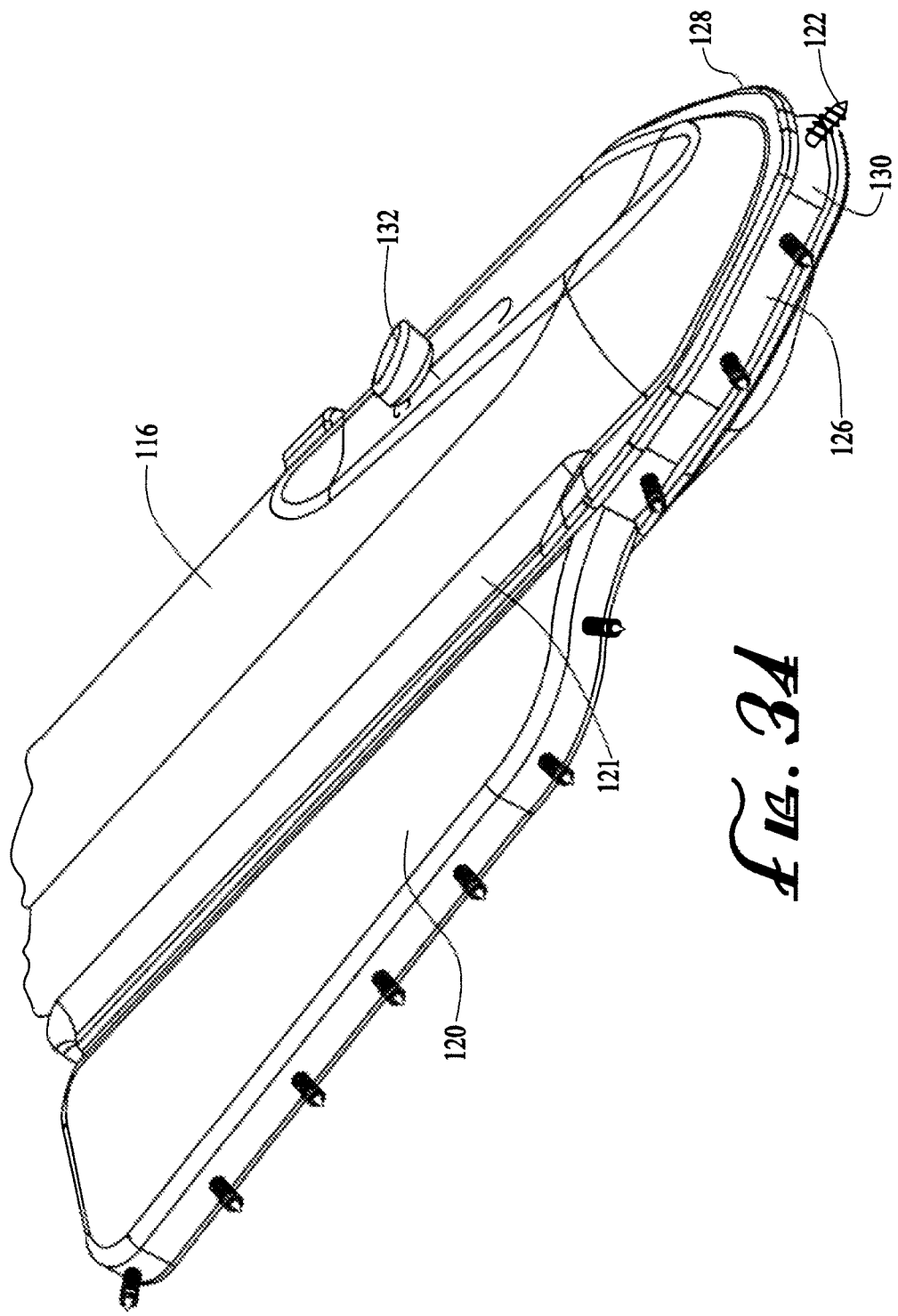

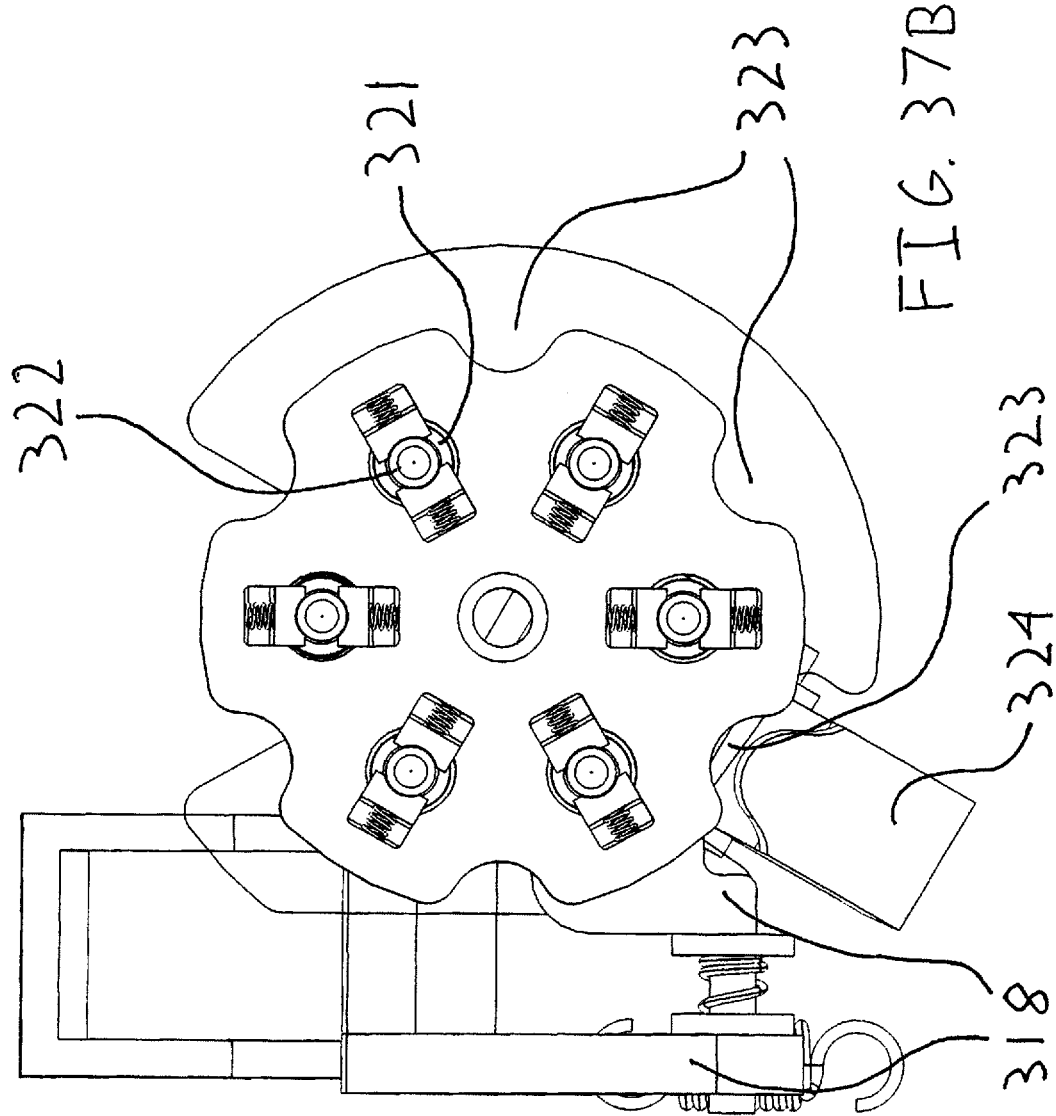

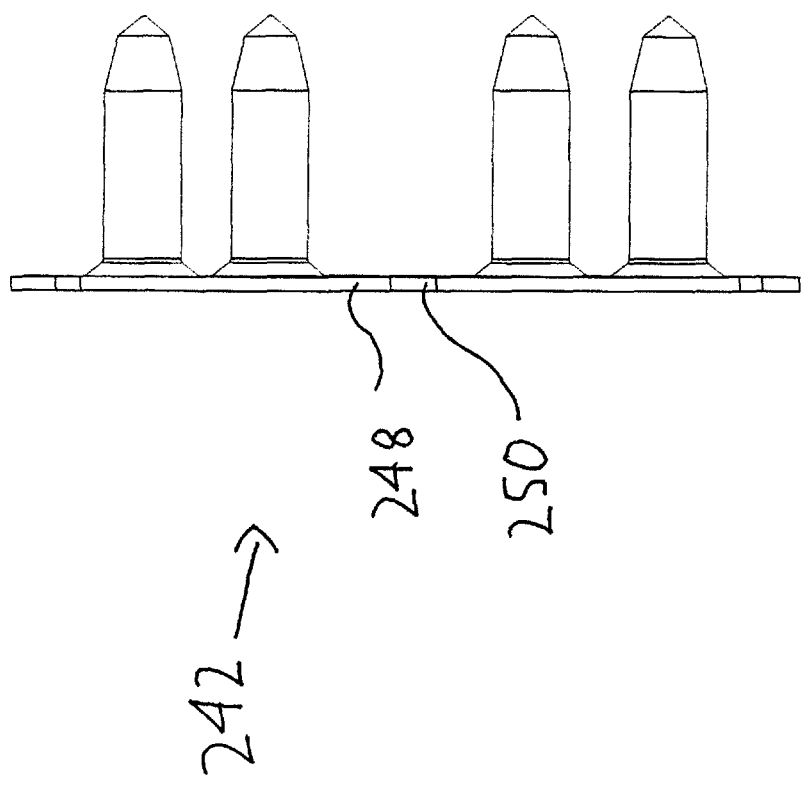

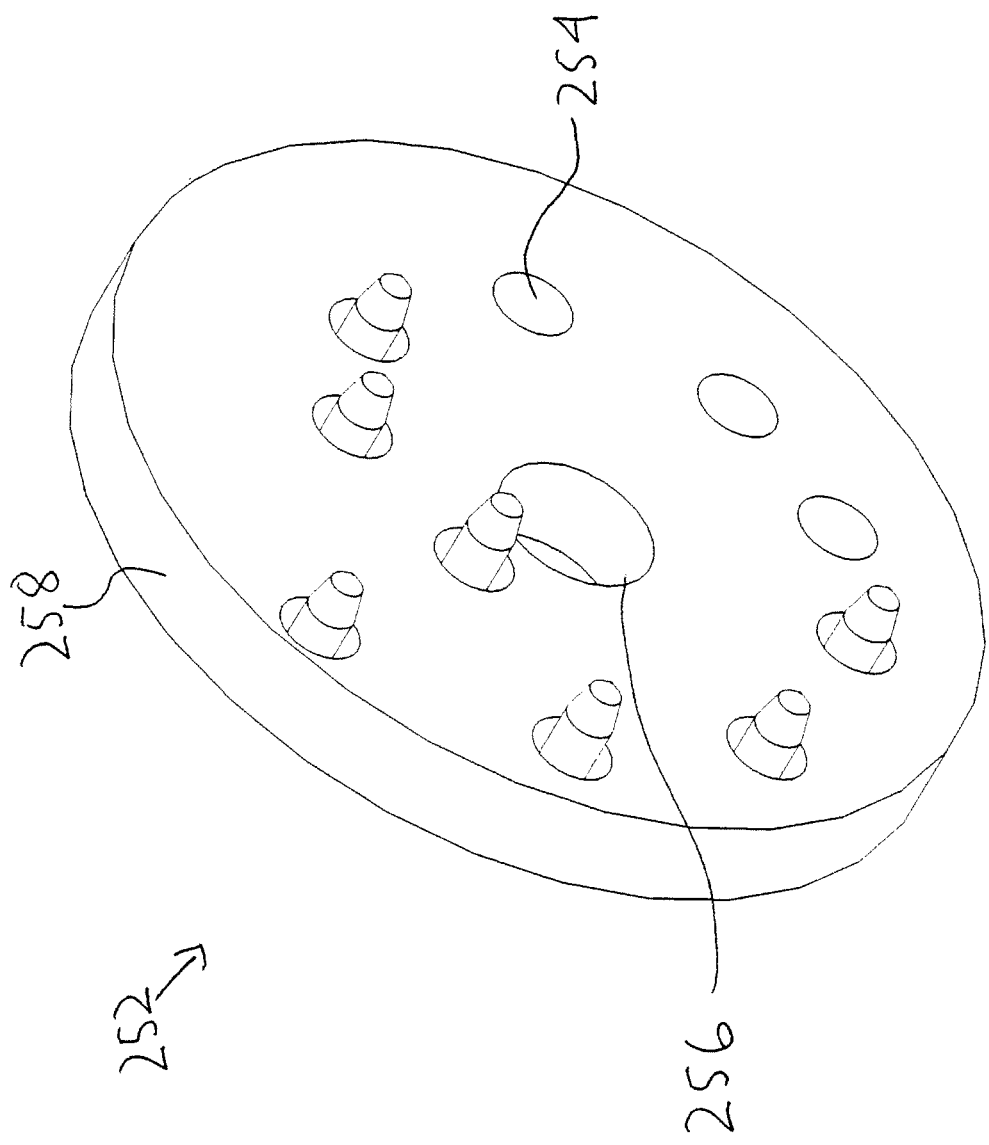

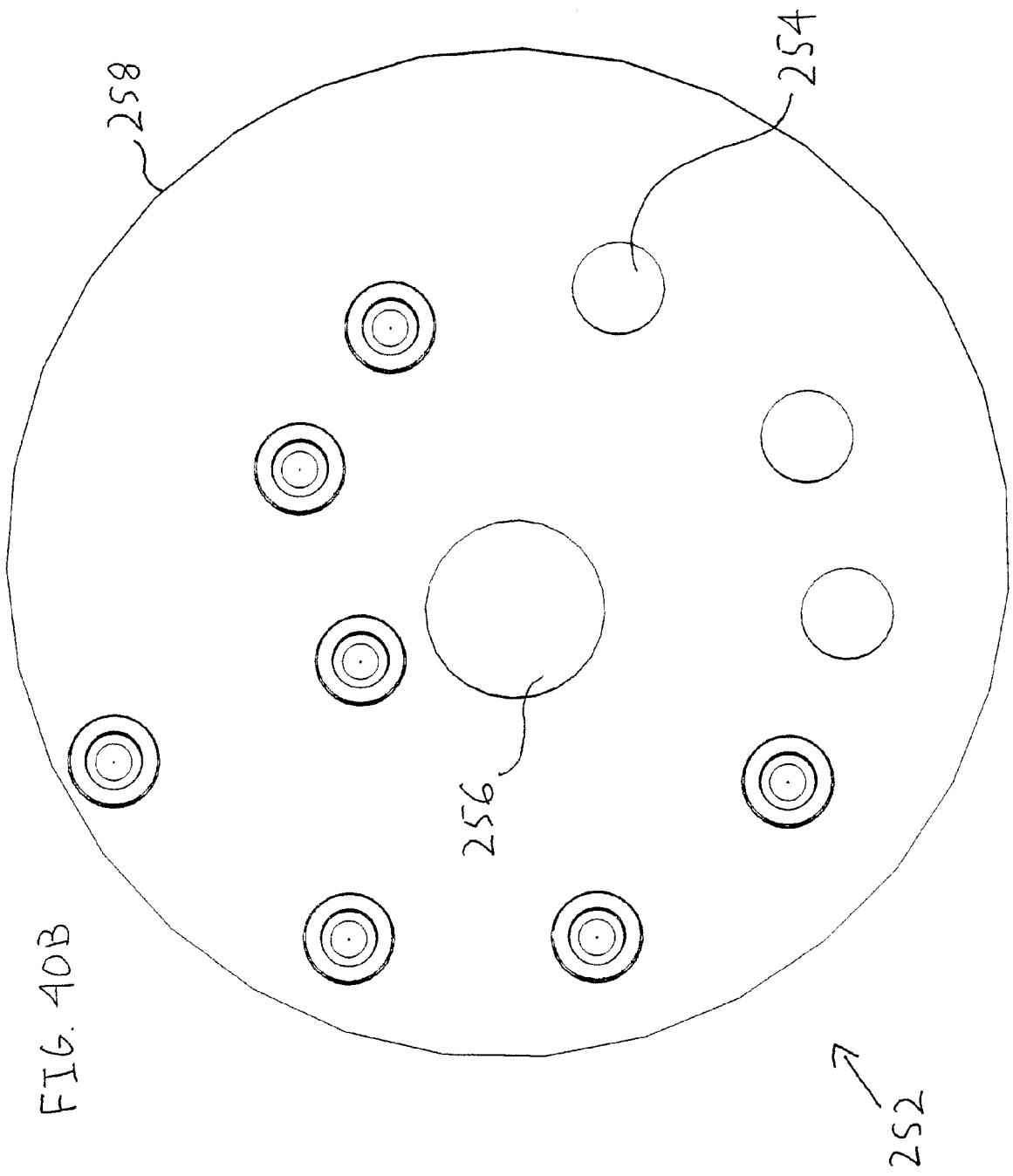

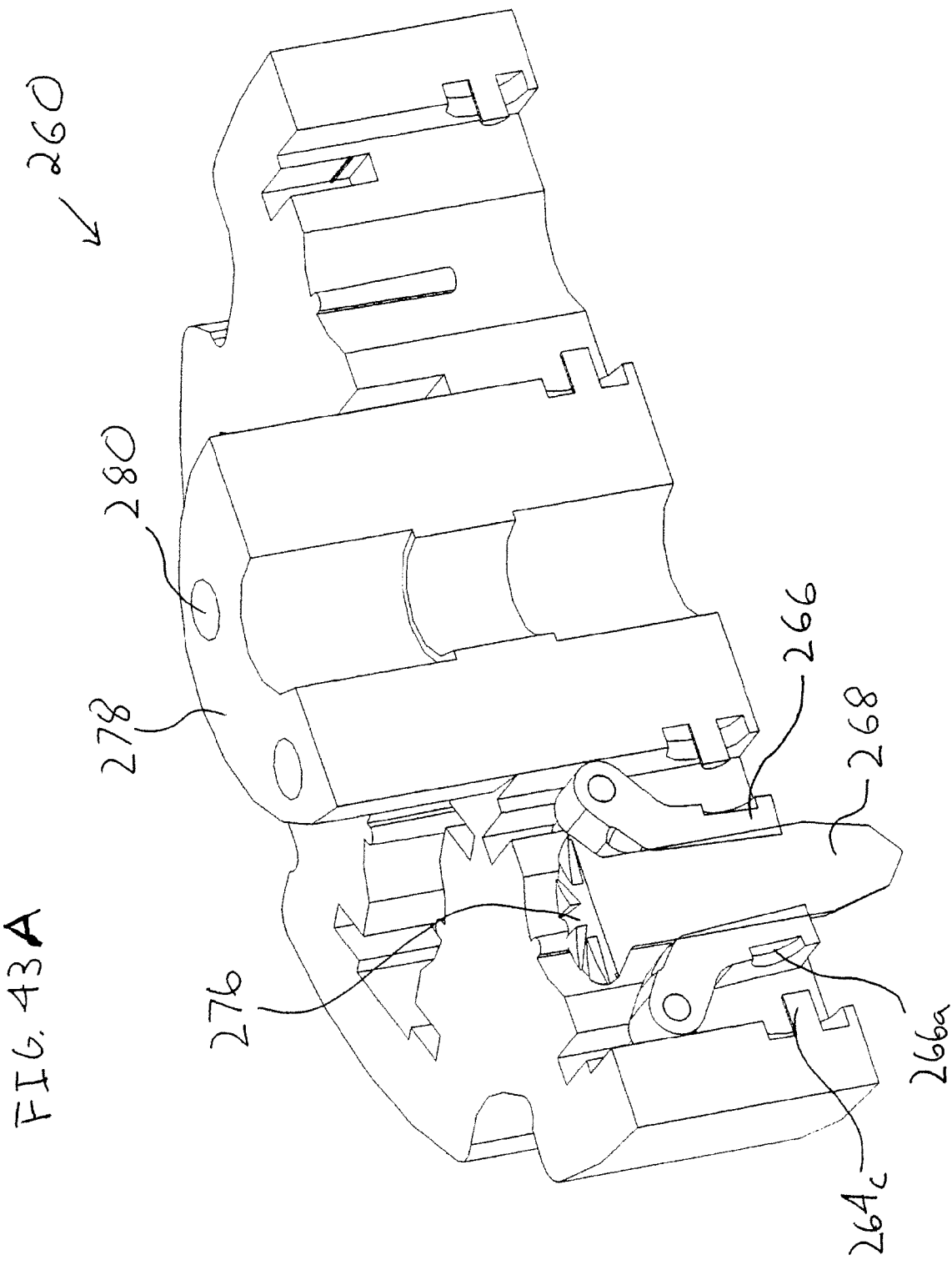

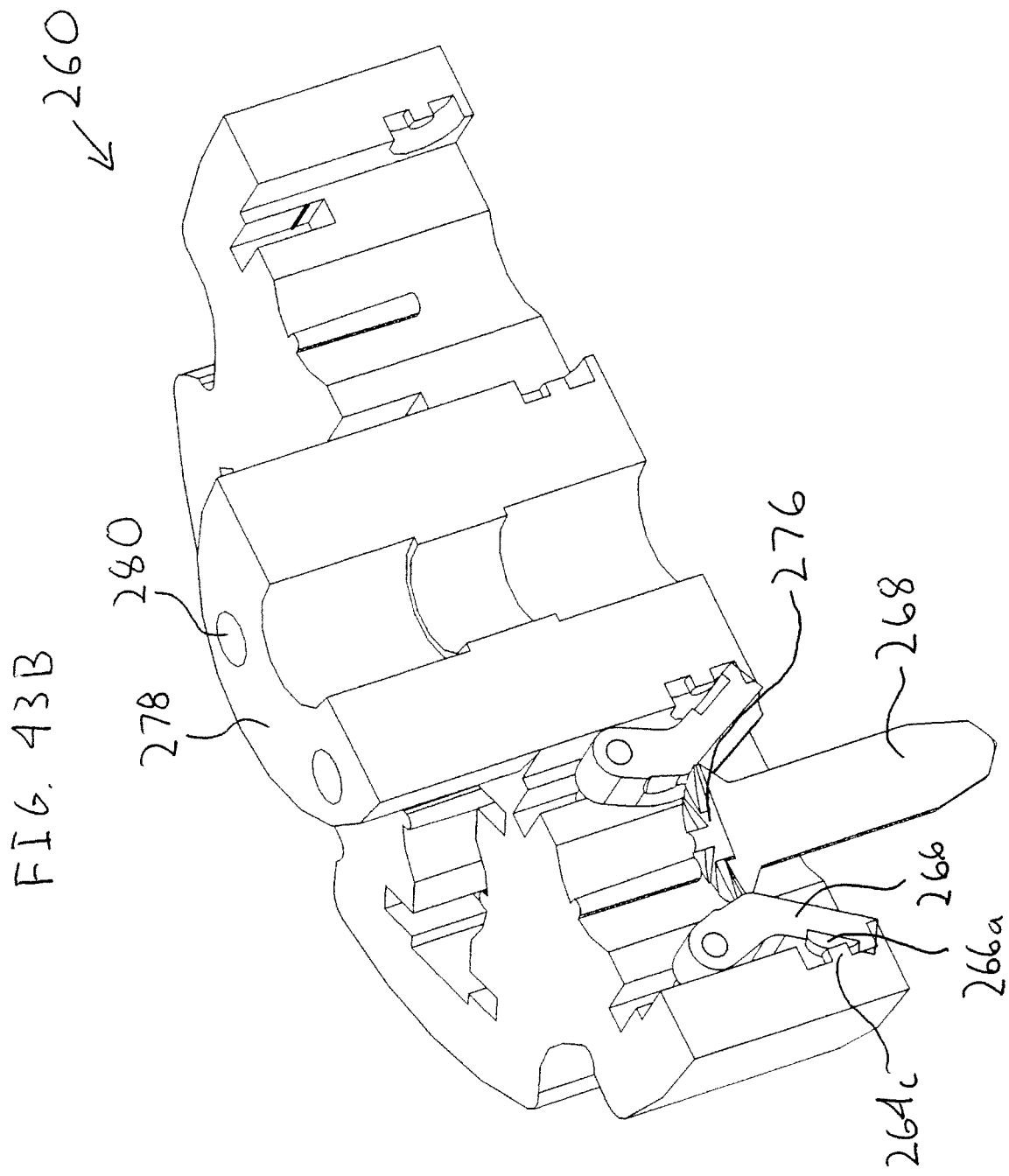

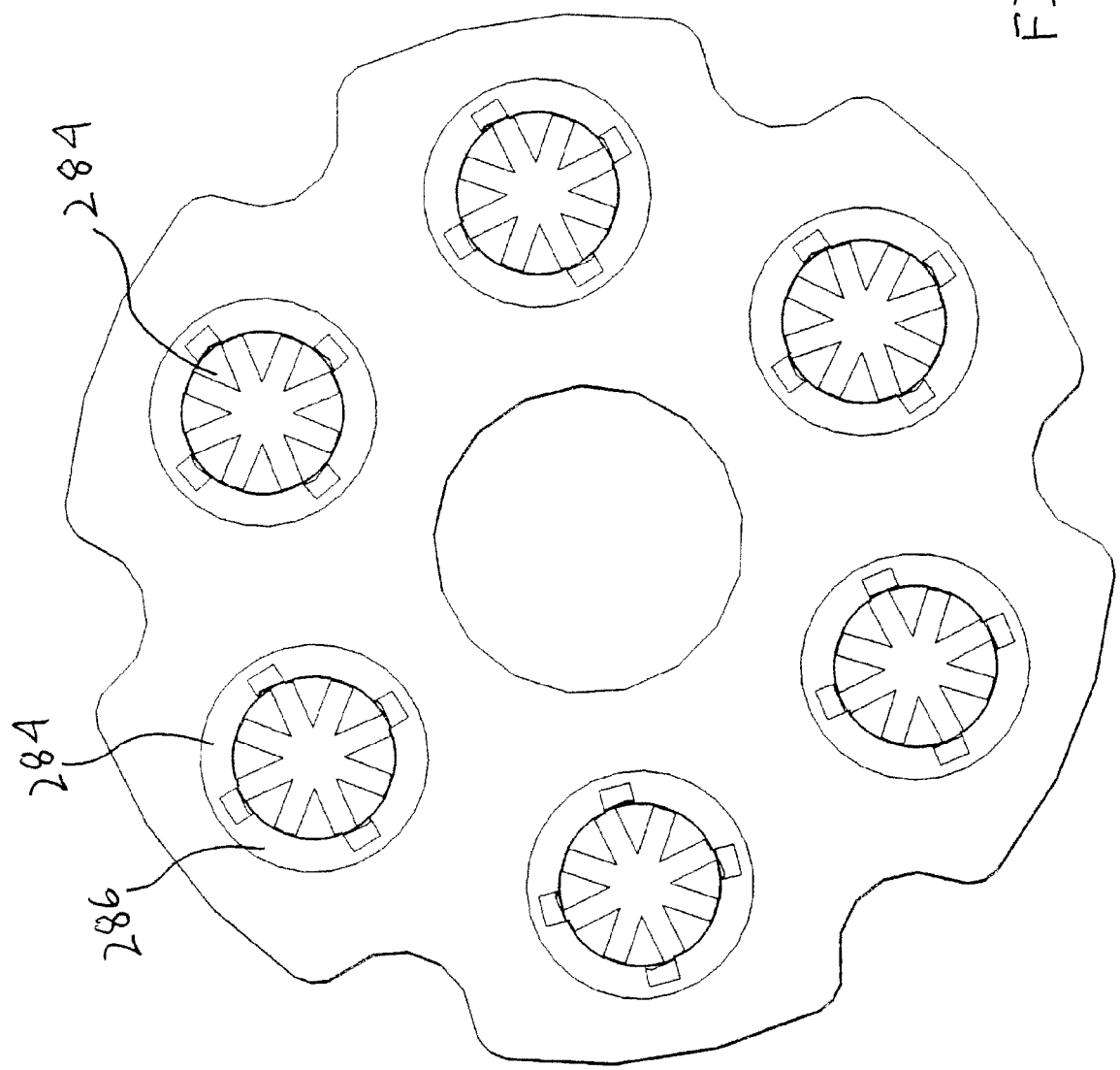

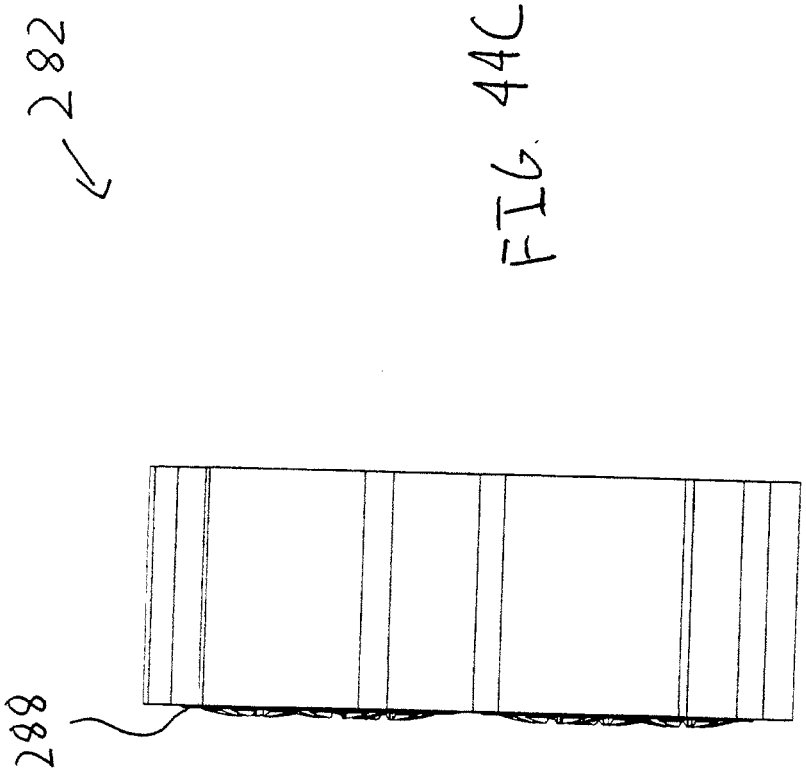

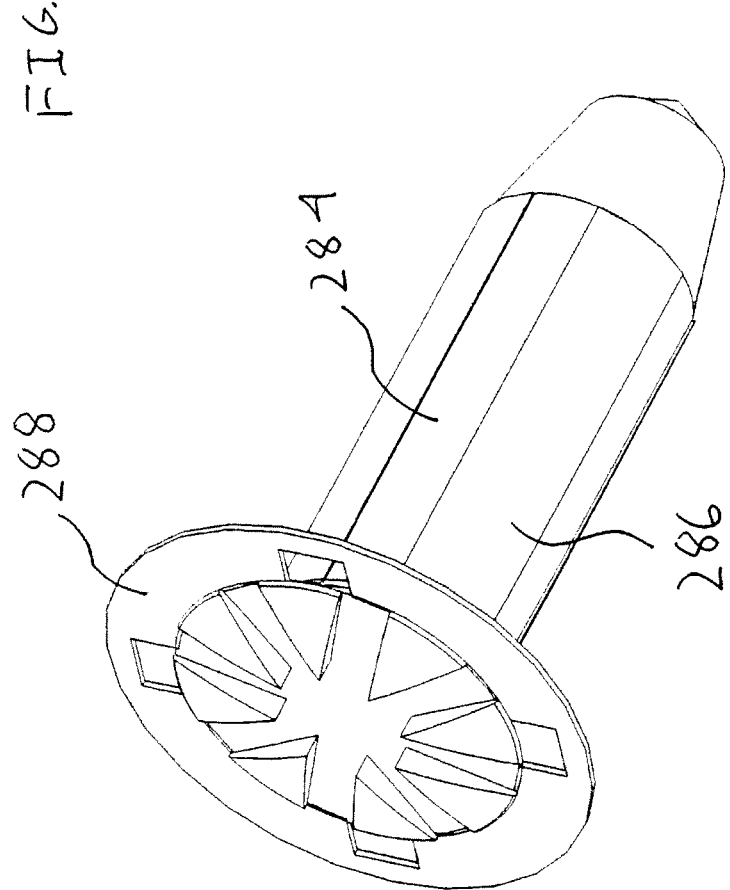

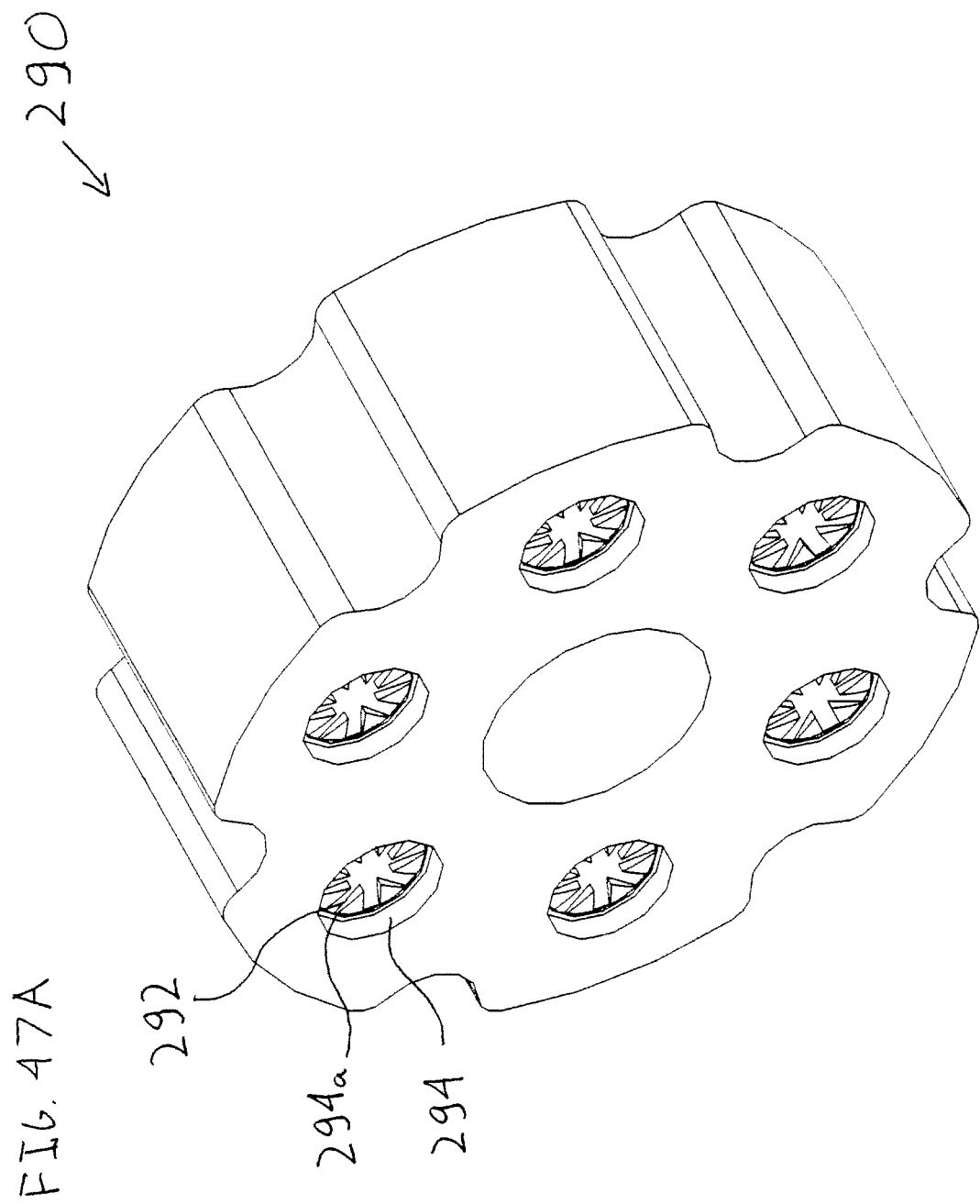

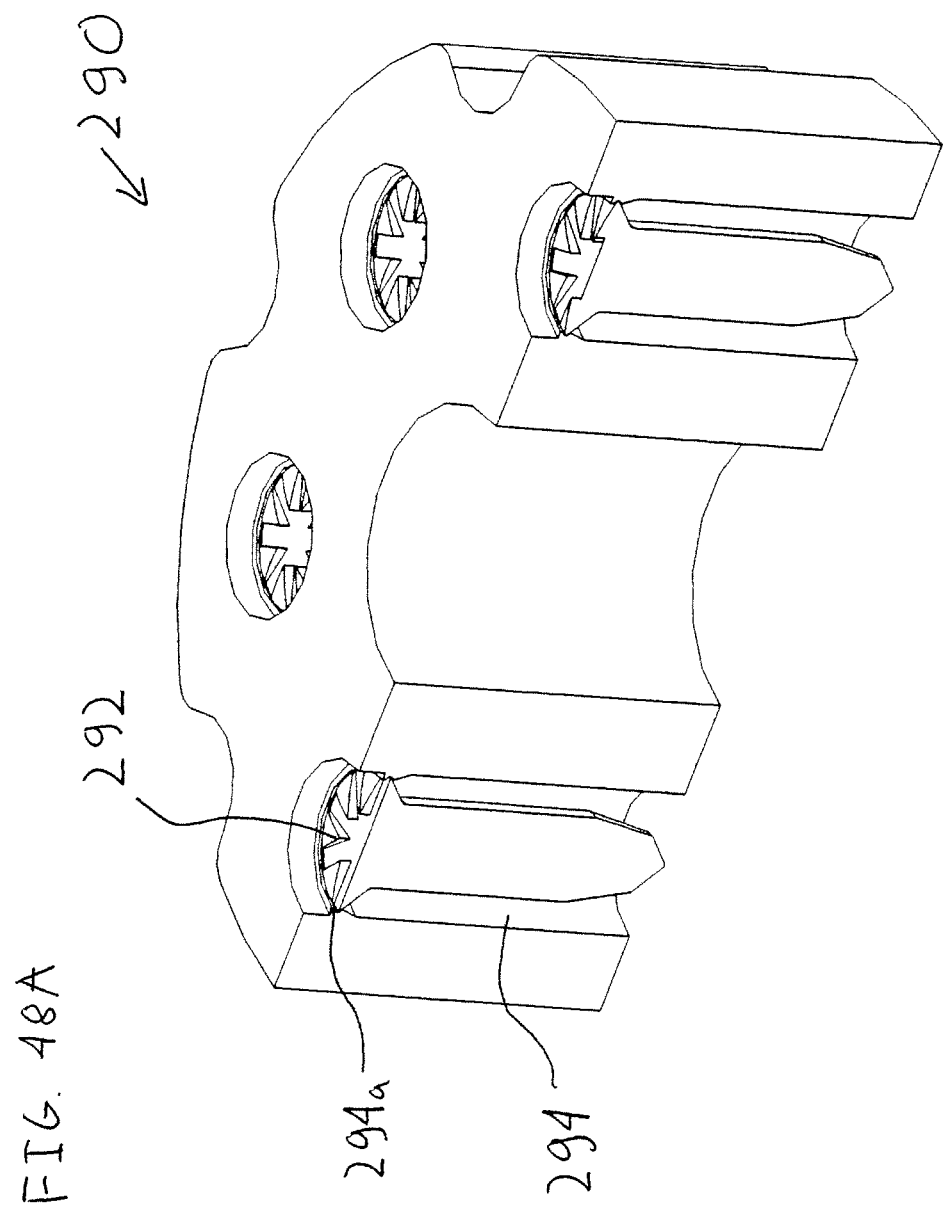

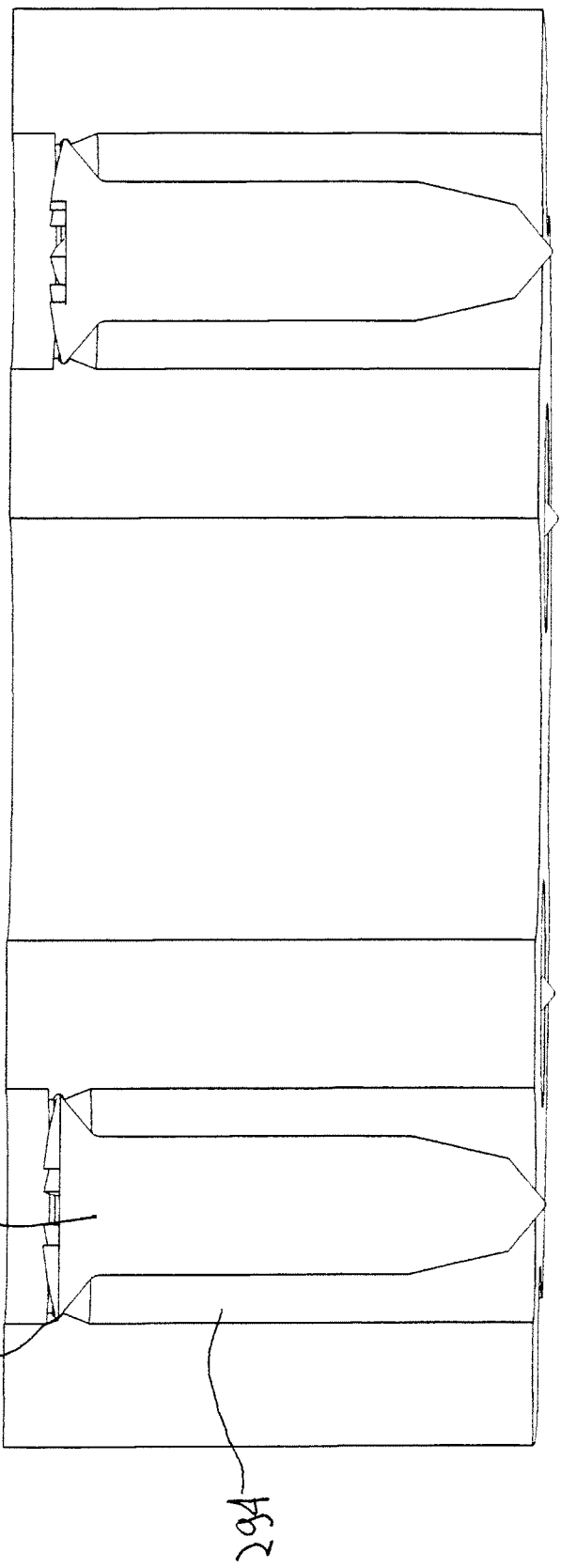

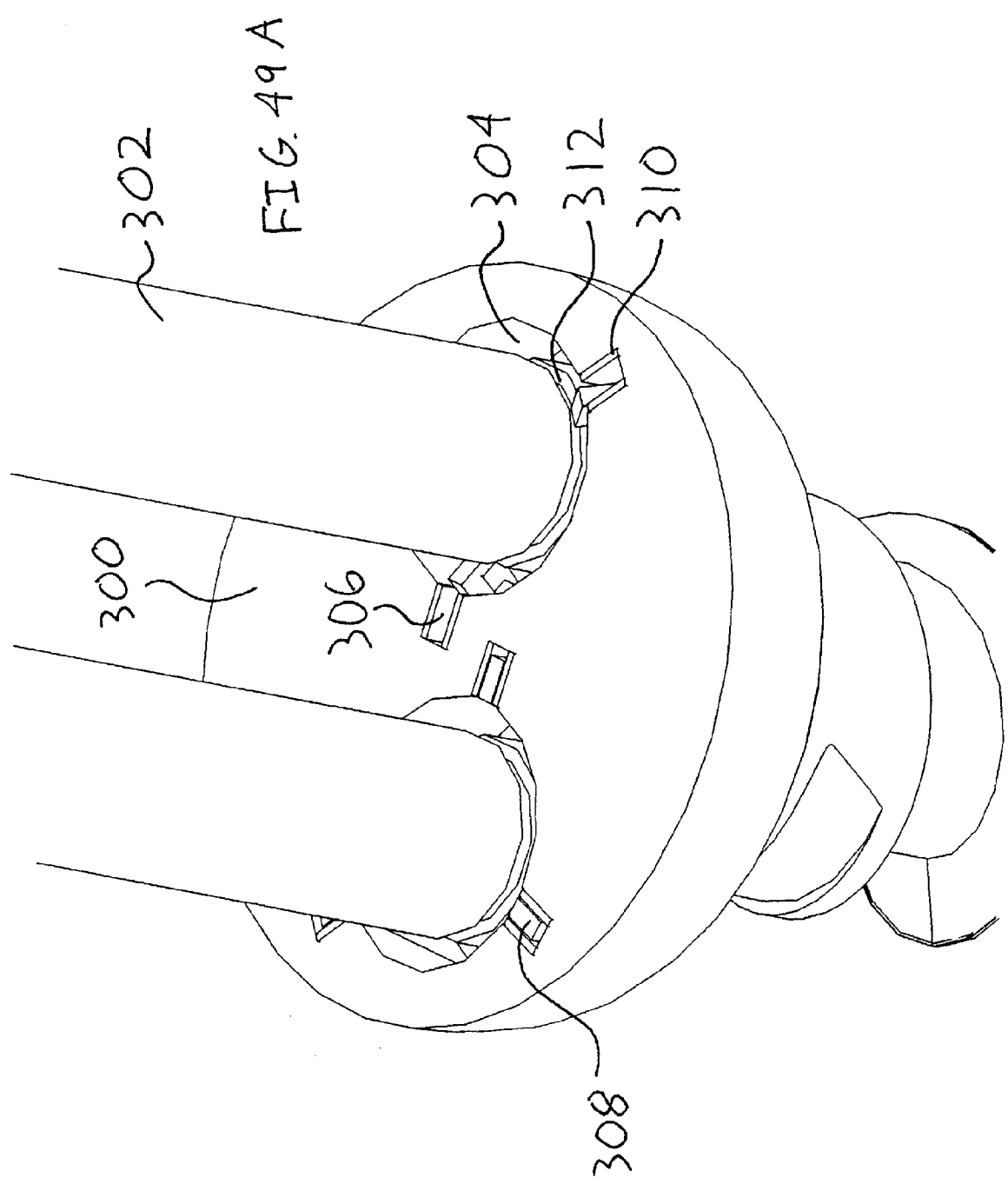

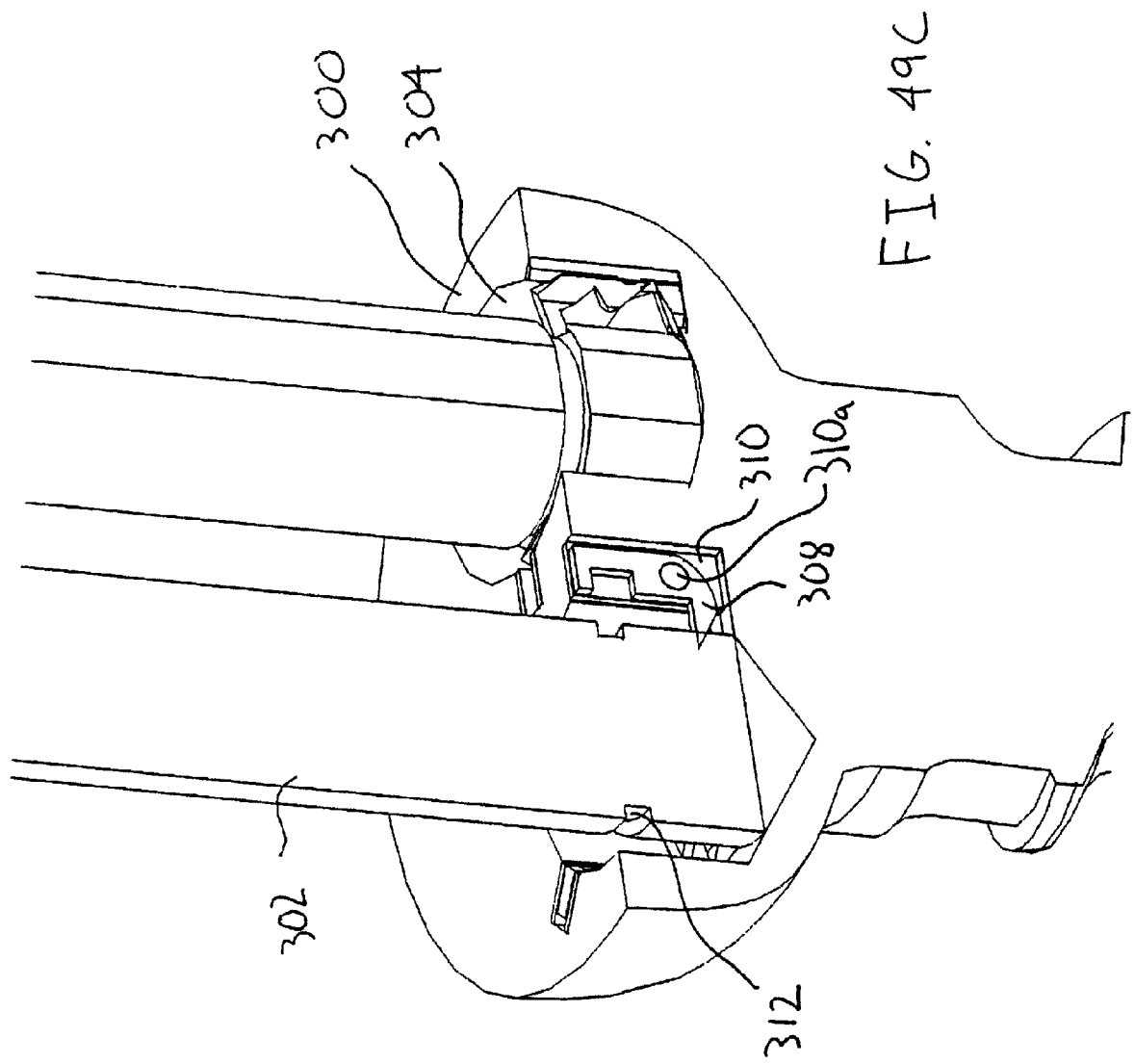

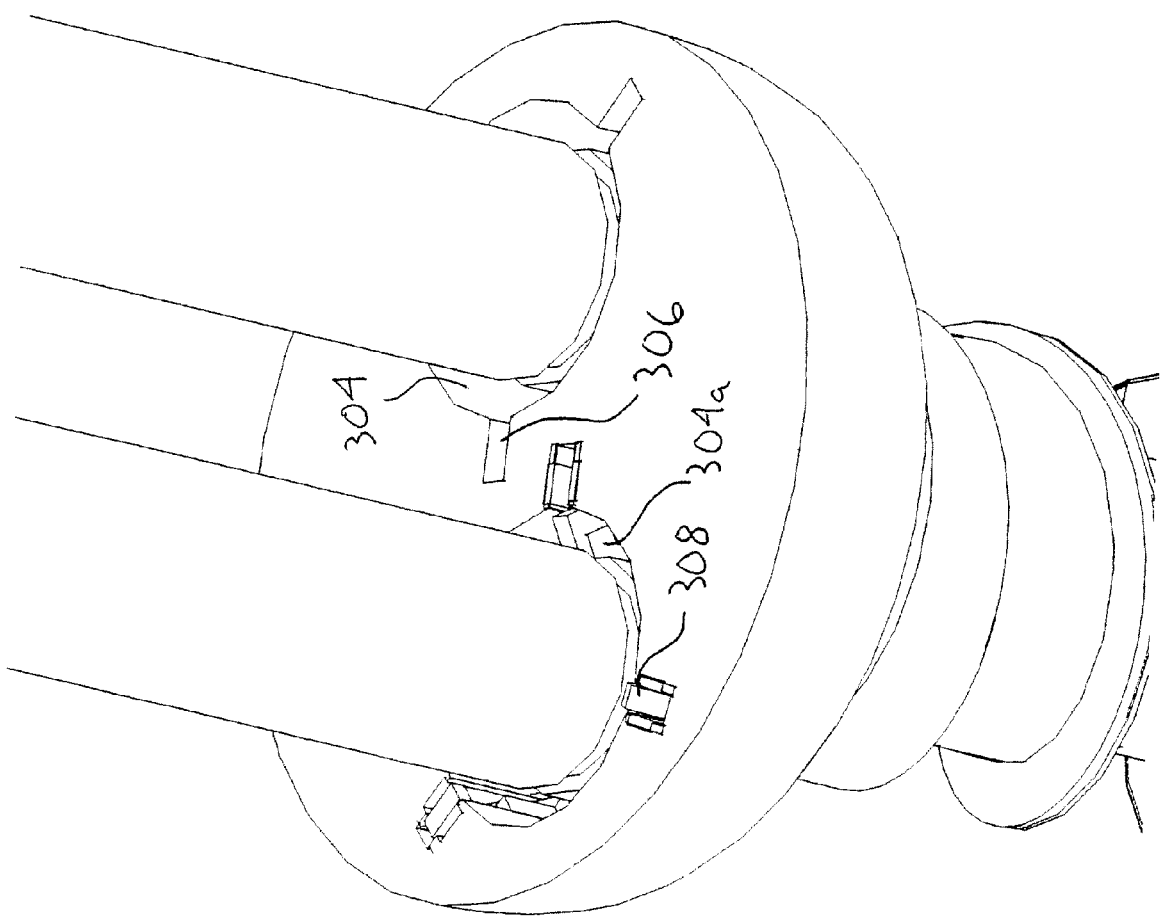

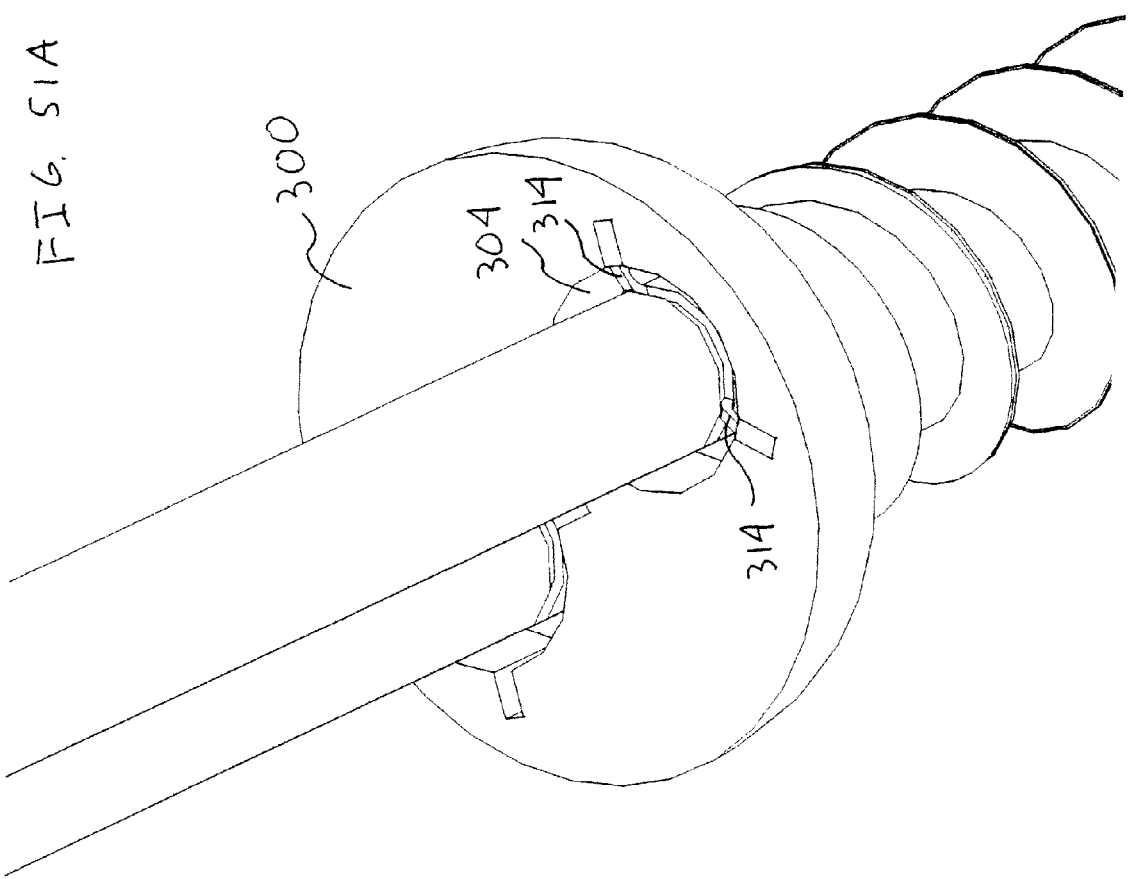

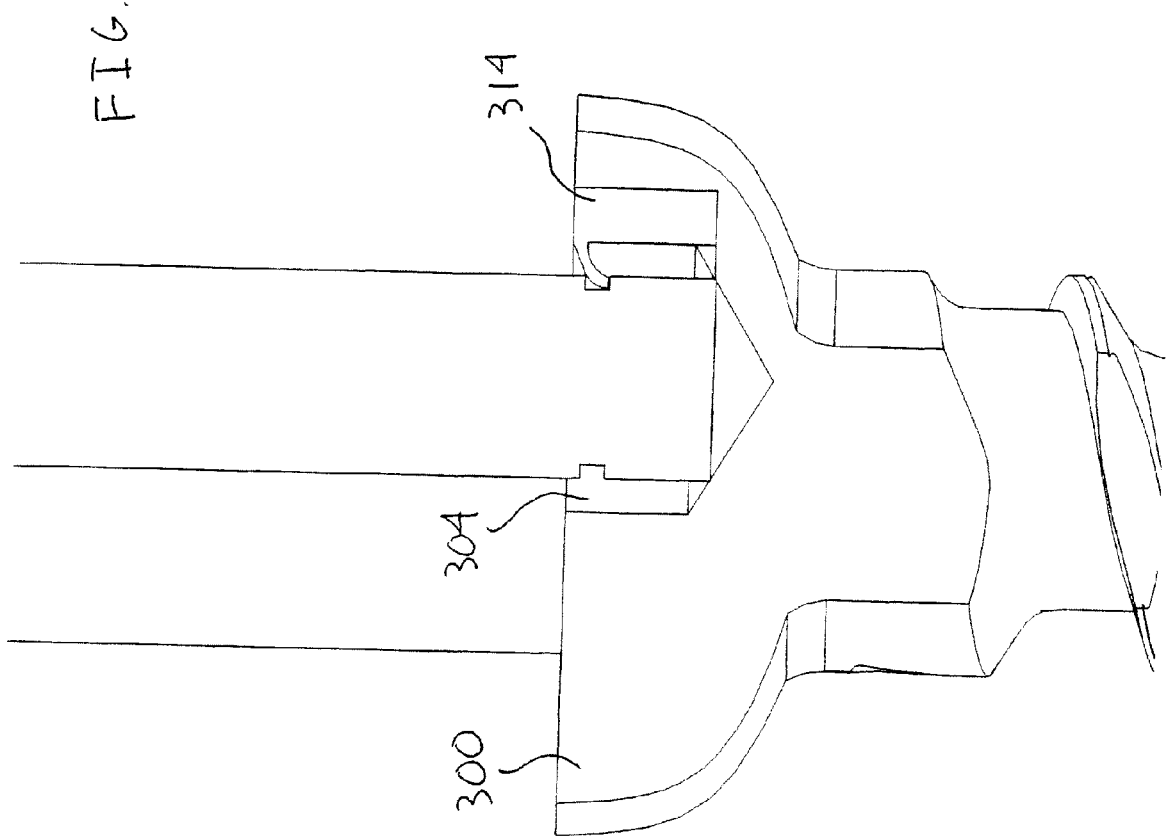

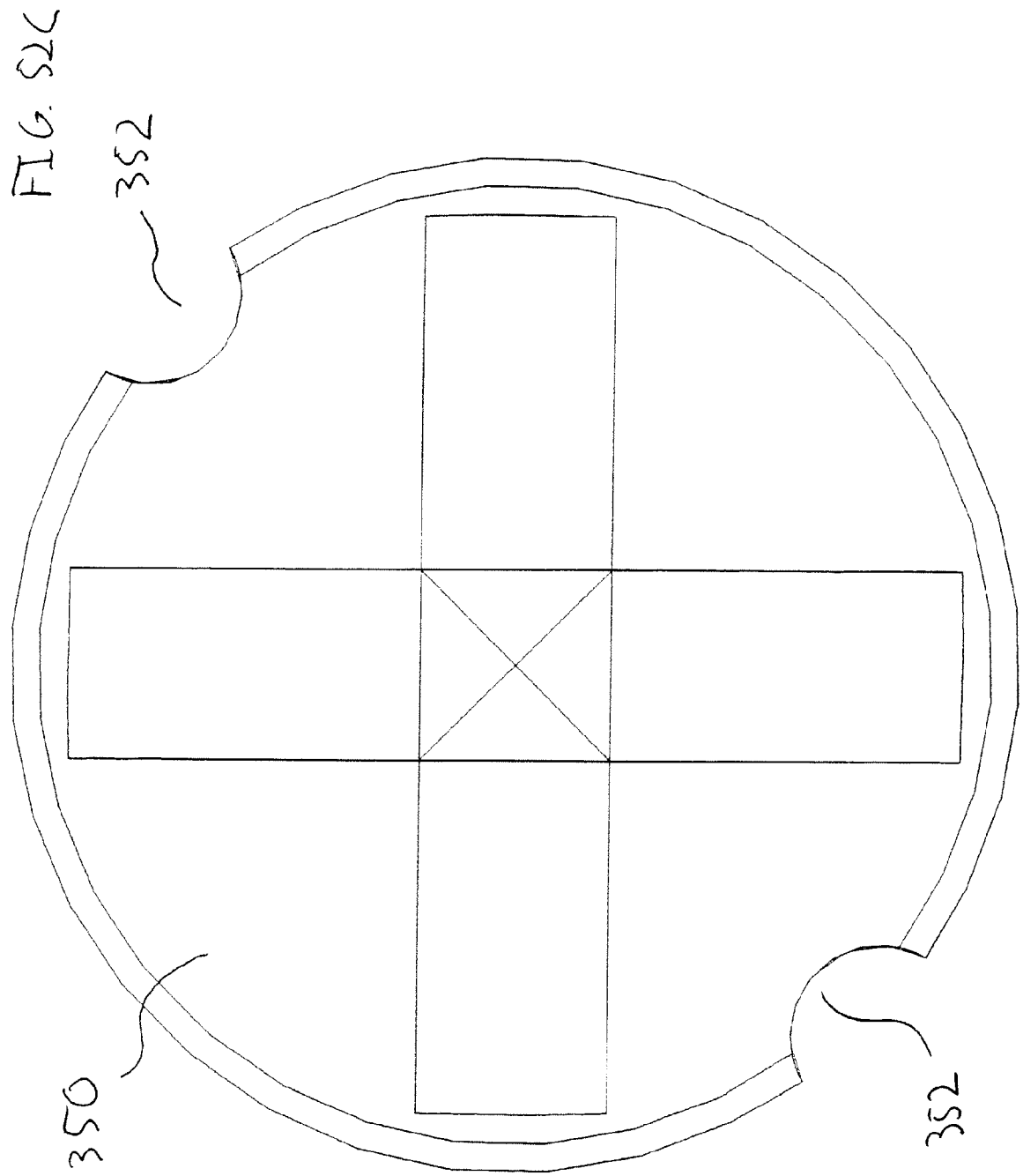

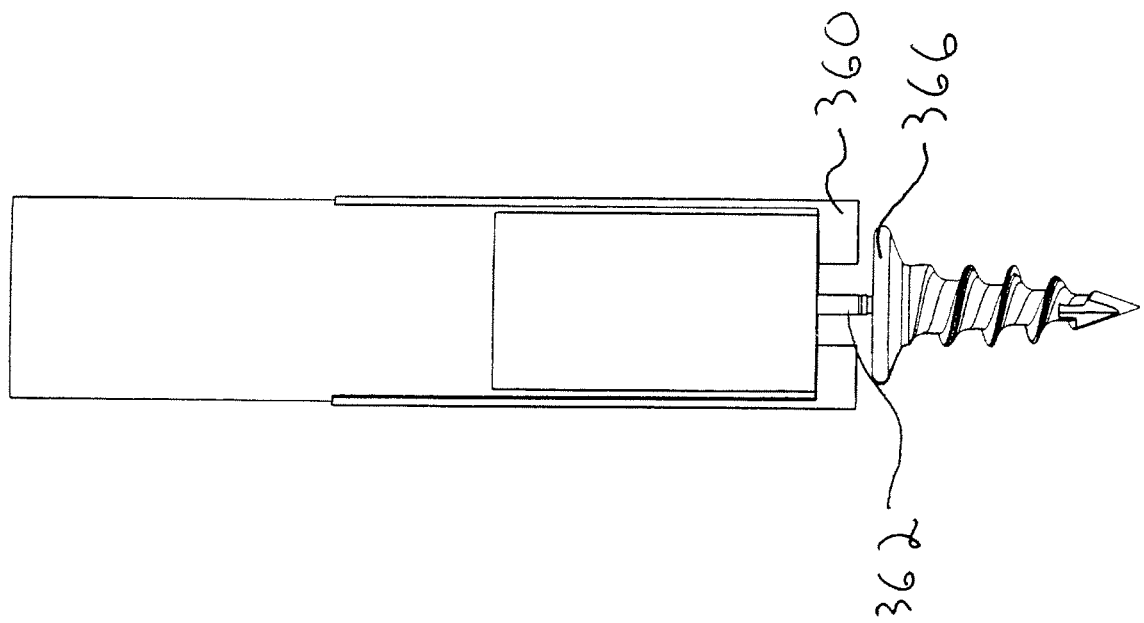

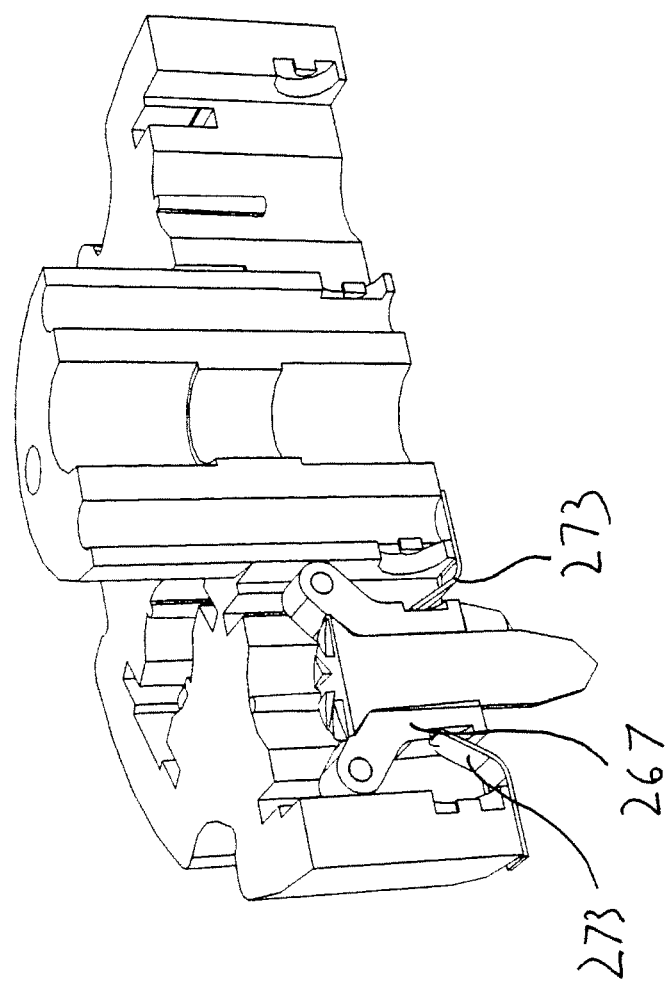

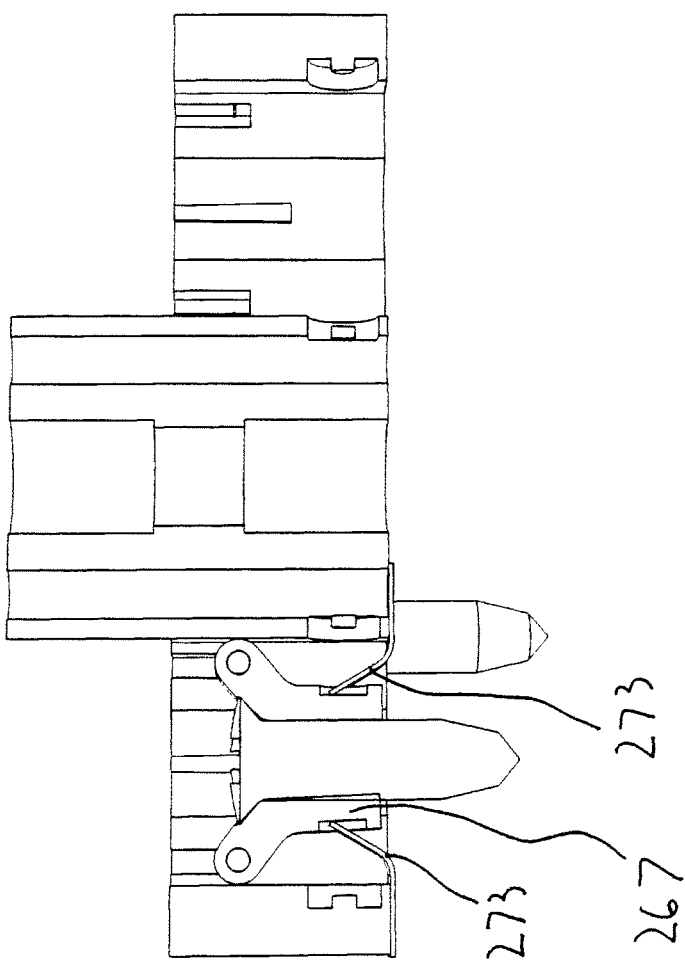

MULTI-CHAMBER AUTOMATIC FEED MEDICAL SCREWDRIVER

This is a Continuation-in-Part of U.S. patent application Ser. No. 12/353,363, filed Jan. 14, 2009, and issued as U.S. Pat. No. 8,262,669 on Sep. 11, 2012.

The present invention is generally directed to a fastener and drive system and methods for the use thereof. The fastener and drive system comprises a driving tool and fasteners fed from a cartridge removeably attached to the driving tool and includes a feed system to position the fastener adjacent the active driving portion of the drive system. In a preferred embodiment the fasteners are held in a revolving chamber. More specifically, the fastener and drive system is designed for placing screw fasteners into tissue or bones during a medical procedure and particularly for the placement of very small fasteners in cranial maxillo-facial procedures and reconstruction of bone supported anatomical features.

BACKGROUND

Surgical reconstruction of hard tissue, such as the placement of prosthetics, the repositioning and attachment of fractured bones and the addition of metallic support plates to repaired bone typically require the placement of fasteners, which may be adhesives, mechanical devices, or combinations thereof. In many instances the fastening system includes screws, which may have special thread and head designs adapted for the particular application or the placement system. These screws are often very small in size and therefore difficult to handle, position and thread into the underlying structure and can easily be dropped into the surgical cavity if they are being manually manipulated.

Systems comprise manual screw drivers or, more recently, cordless, battery powered drivers, to transmit a rotational driving force to screws, which may have specialized heads to match the driver tips. Because a typical procedure may require placement of numerous screws (20-60) the powered drivers are now preferred. A typical power driver is a reusable pencil grip instrument with a replaceable, single use, sterile, disposable battery pack. However, hospital personnel must still perform the tedious task of attaching each screw to the tip of the screwdriver or into a retaining structure on the tip and then handing it to the surgeon or manually loading a feeding system adapted to place the screw in front of the driver tip. The screw head has a recessed structure, such as a slot or a recessed geometric structure for example, cruciform, Phillips, square, hexagonal or exalobe shaped holes, for torque transmission from a matching structure on the tip of the driver. For torque transmission and to limit the tip from disengaging from the structure in the screw head the tolerances of the fit between the tip and the screw head construction are minitnal and in some instances tapered to provide secure engagement (U.S. Pat. No. 4,269,246 to Larson et al.)

There are numerous publications and patents which show devices that relate to the field of the invention. They are directed to the placement of, or automatic delivery of, fasteners to a particular location and systems for driving the fasteners. The following are merely representative of the art; there are others which are primarily repetitive of those discussed herein. Many are for industrial applications and can not meet the needs of a surgeon for use in an enclosed, sterile environment and do not lend themselves to automatic one hand operation. Systems for delivering a fastener to the operative, rotating tip of a screw driver include:

a) Non-Banded Delivery—U.S. Pat. No. 3,946,926 to Willis is an example of a pneumatic or strictly mechanical delivery of fasteners from a hopper. U.S. Pat. No. 4,408,877 to Lindmo et al. appears to cover loose screws fed along a track disposed in front of the screwdriver tip.

b) Stacked Fasteners—U.S. Pat. No. 5,590,574 to Lide is an example of a system that provides a linear arrangement of fasteners stacked head to tail inside the screwdriver.

c) Vertical Band—There are numerous patents to systems in which the fastener (nail or screw) lies across the face of a band and are attached to the band by notches or loops extending from the surface of the band. Alternatively the band may have a thickness so that the fastener can be inserted in a hole which extends through the band from one edge to a parallel opposite edge, for example, U.S. Pat. Nos. 5,758,768, 5,622,024, 5,469,767, and 4,930,630 to Habermehl as well as numerous other Habermehl patents. However, they all appear to use a band which attaches to the side of the fastener and which places the band in a plane coextensive with the axis of the screwdriver.

d) Horizontal Band—There are numerous patents that are directed to systems in which the screw is placed through a hole in the surface of the band with the band resting somewhere along the length of the shank of the screw or just below the head of the screw. These include US Patents to Chen (U.S. Pat. No. 5,522,687), Dohi (U.S. Pat. No. 5,544,746), Hon (U.S. Pat. No. 5,509,768), Huang (U.S. Pat. Nos. 5,931,298, 5,803,691, 5,788,445, 5,779,420), Lejdegard (U.S. Pat. No. 4,018,334), Lin (U.S. Pat. No. 5,775,514), and Shinjo (U.S. Pat. Nos. 5,984,096 and 6,761,268) all of which show various band designs which include extensions created from or formed below the surface of the band designed to grip the shaft of the screw.

Other patents are directed to the surgical fasteners and the design of the head of the fastener and drivers constructed to work with these fasteners or hold the fastener during the placement procedure. None of these patents include automatic delivery of the fasteners.

These prior devices do not provide the ease of operation and the ability to continuously and rapidly place numerous screws into the bone structure while minimizing the risk of loss of the screws during the procedure and the amount of time necessary to prepare the tool and the fasteners for use in the surgical procedure. These deficiencies were addressed in applicant's U.S. Pat. No. 7,406,899, incorporated herein in its entirety by reference.

SUMMARY

Devices and methods are described for placement of fasteners, namely screws, for medical applications which utilizes an automatic delivery system for the fastener and a drive system, preferably powered by replaceable or rechargeable batteries, for automated and continuous delivery and placement of the fasteners from a reloadable or disposable cartridge.

Activating a trigger mechanism causes the tip of the screw driver to extend and interlock with the head of the fastener temporarily held in the cartridge, removing the fastener from the cartridge, rotating the driver tip and fastener for driving the fastener into a tissue or bone structure. Releasing the trigger following positioning of the fastener in the bone or tissue disconnects the screw driver tip from the fastener head, retracts the screw driver tip from the cartridge and causes the fastener carrier system to advance forward to position a subsequent fastener in a location for grasping and driving by the screw driver tip.

BRIEF DESCRIPTION OF THE DRAWINGS

FIG. 5 is a side view of a first embodiment of a screw fastener for use in the fastener placement system.

FIG. 6 is a cross sectional view of the screw of FIG. 5 taken along line 6-6 of FIG. 5.

FIG. 6a is an enlarge view of the circled portion of FIG. 6.

FIG. 7 is a top view of the screw of FIG. 5 showing a first embodiment of structure in the screw head to receive a matching driver tip.

FIG. 8 is a side view of a driver tip designed to interact with the screw head embodiment of FIG. 7.

FIG. 9 is an end view of the driver tip of FIG. 8.

FIGS. 17a, b and c, 18a, b and c, 19a, b and c, 20a, b and c, and 21a, b and c are top, longitudinal cross sections and side views respectively of five embodiments of different hole structure in the head of the fastener as well as an external taper for external grasping of the fastener.

FIG. 22 is a perspective side view of a driver tip holding one of the embodiments of FIGS. 17-21.

FIG. 27 is a bottom perspective side view of the screw delivery portion showing the track for mounting the replaceable cartridge assembly.

FIG. 30 is a cutaway side view of the driver tip inserted into the head of the fastener of FIG. 5.

FIG. 31 is a perspective view of an alternative band structure for holding the fasteners.

FIG. 32 is a perspective side view of a second embodiment of a fastener placement system incorporating features of the invention.

FIG. 34 is a perspective view of the lower side of the embodiment of FIG. 32 showing the fasteners in a carrying strip.

FIGS. 43A and B are perspective cross-sectional views of a cartridge comprising a fastener in an upper and lower position, respectively, and cantilever holders.

FIGS. 48A and B are cross-sectional perspective and side views respectively of a cartridge comprising a fastener held by molded features.

FIG. 49A is a top perspective view and 49C is a cutaway perspective view of an embodiment of a driver tip and a fastener head engagement system.

FIG. 50 is a perspective view respectively of a different driver tip and fastener head engagement system.

FIGS. 51A and B are perspective view and cross-sectional side view of another driver tip to fastener head engagement system.

FIGS. 54A and B are perspective cross-sectional and side cross-sectional views of a chamber comprising another cantilever embodiment.

DETAILED DESCRIPTION

Figure 1:
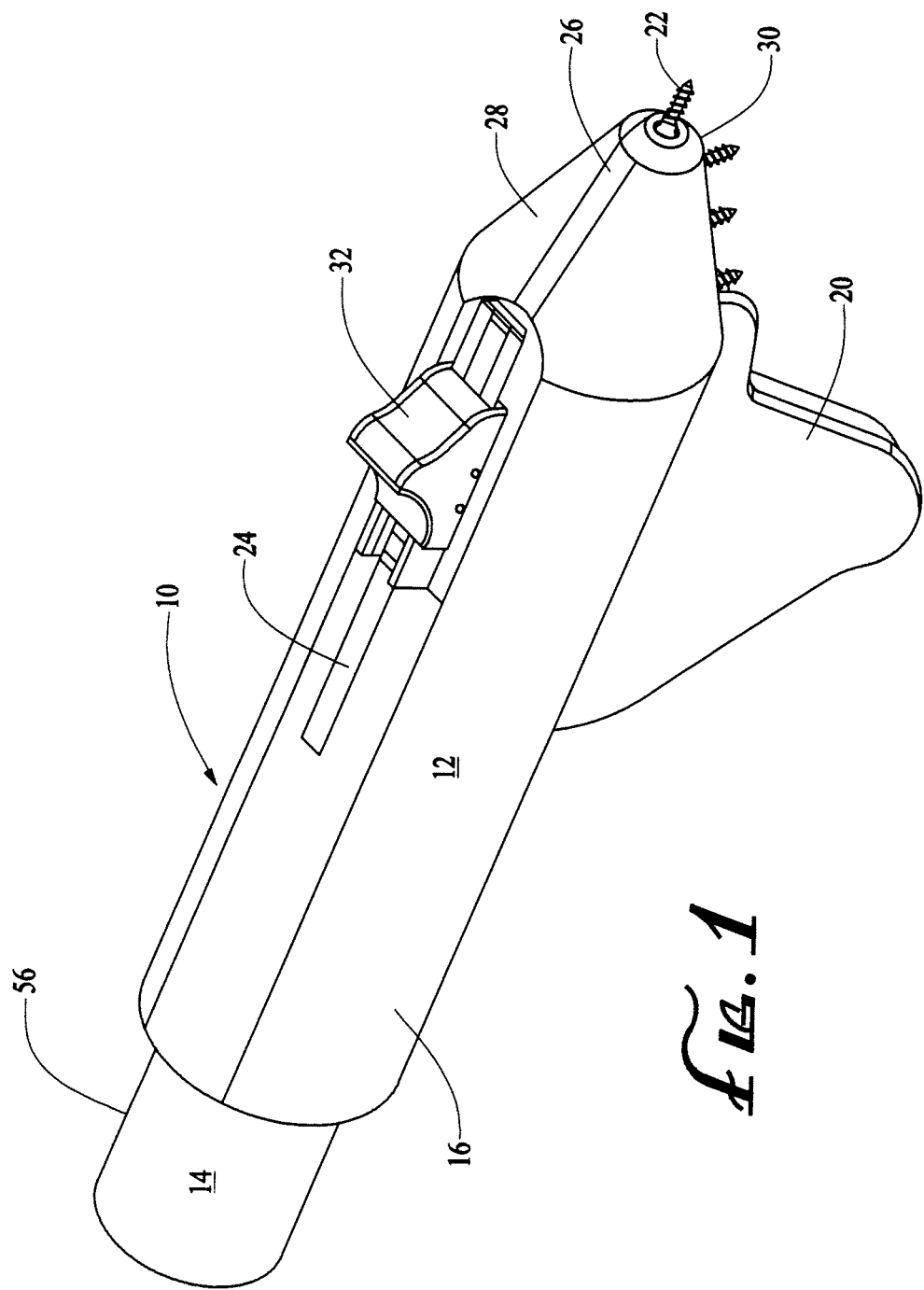
FIG. 1 is a perspective side view of a first embodiment of a fastener placement system incorporating features of the invention.

The fasteners and drivers disclosed herein, referred to in combination as a fastener system, is primarily intended for use in medical procedures which require the placement of small surgical screws, such as would be used in a cranial maxillo-facial procedures, prosthetic or an orthopedic procedure, which are automatically positioned and held in front of the tip of the screwdriver so that multiple screws can be placed in a serial manner by a one hand operation.

The fastener system includes an automatic finger activated driver having a tip which rotates around its central, longitudinal axis by an electrical drive means, such as rechargeable or replaceable batteries. While less preferred, the driver may alternatively be driven by external AC or DC power sources, or pneumatic or hydraulic drives. As a still further alternative gas cylinders inserted in the driver handle instead of batteries can be used to provide a replaceable or rechargeable drive system. As a still further alternative, the rotating tip can be driven by a negative pressure provided by an external vacuum source.

A feature of the system described herein is a fastener head construction and a driver tip configuration which allows the driver tip to be inserted into a depression in the head of the fastener or grasp the outer edge of the head, while at the same time separating the fastener from a carrier strip. This eliminates the task of manually mounting the fastener on the driver tip. The fastener can then be readily transported to the surgical placement site without fear of dropping the fastener and driven into the bone at the surgical placement site. The driver tip is then retracted, leaving the fastener in place in the bone and a subsequent fastener automatically moves into position in front of the driver tip to repeat the procedure.

A preferred embodiment uses a replaceable cartridge which includes multiple fasteners inserted therein. The fasteners are held in the cartridge by structure integral with the edges of holes in the cartridge, the structure gripping the edge of the head of the fastener. However, other cartridges or different retaining structures can be used to hold and place the fasteners in front of the driver tip. Still further, different means, such as a hopper containing fasteners can be used to funnel individual fasteners, one at a time, to a point in front of the driver tip where they are temporarily held until the driver tip locks into or onto the fastener head.

One skilled in the art, based on the disclosure set forth herein, can design other techniques to carry the fastener to a point in front of the driver tip for placement of the tip in the fastener head ready for driving into the surgical site.

In a first embodiment multiple screws are temporarily attached along the length of a band. The screw delivery system includes a removable and replaceable cartridge structure to enclose the band of screws and a track for the band of screws to travel along for placement in front of a screw driver tip. Each successive screw on the band is serially positioned in front of the tip of the screw driver tip. A trigger mechanism causes the band to move forward in front of the tip, placing the fastener in the right position to be engaged by the driver tip. The driver tip includes an enlarged portion which is inserted into the head of the screw or around the head of the screw so that when the screw is separated from the band the screw is retained on the tip by interlocking structures. Moving the tip forward engages the screw head, separates the screw head from the band, inserts pins on the tip or other geometric shapes into or around matching shapes in the fastener head, and provides rotary motion to the screw so that it can be driven into a target surface. This is accomplished by rotating the tip within the driver while the screw driver handle is held fixed (not rotated).

Figure 2:
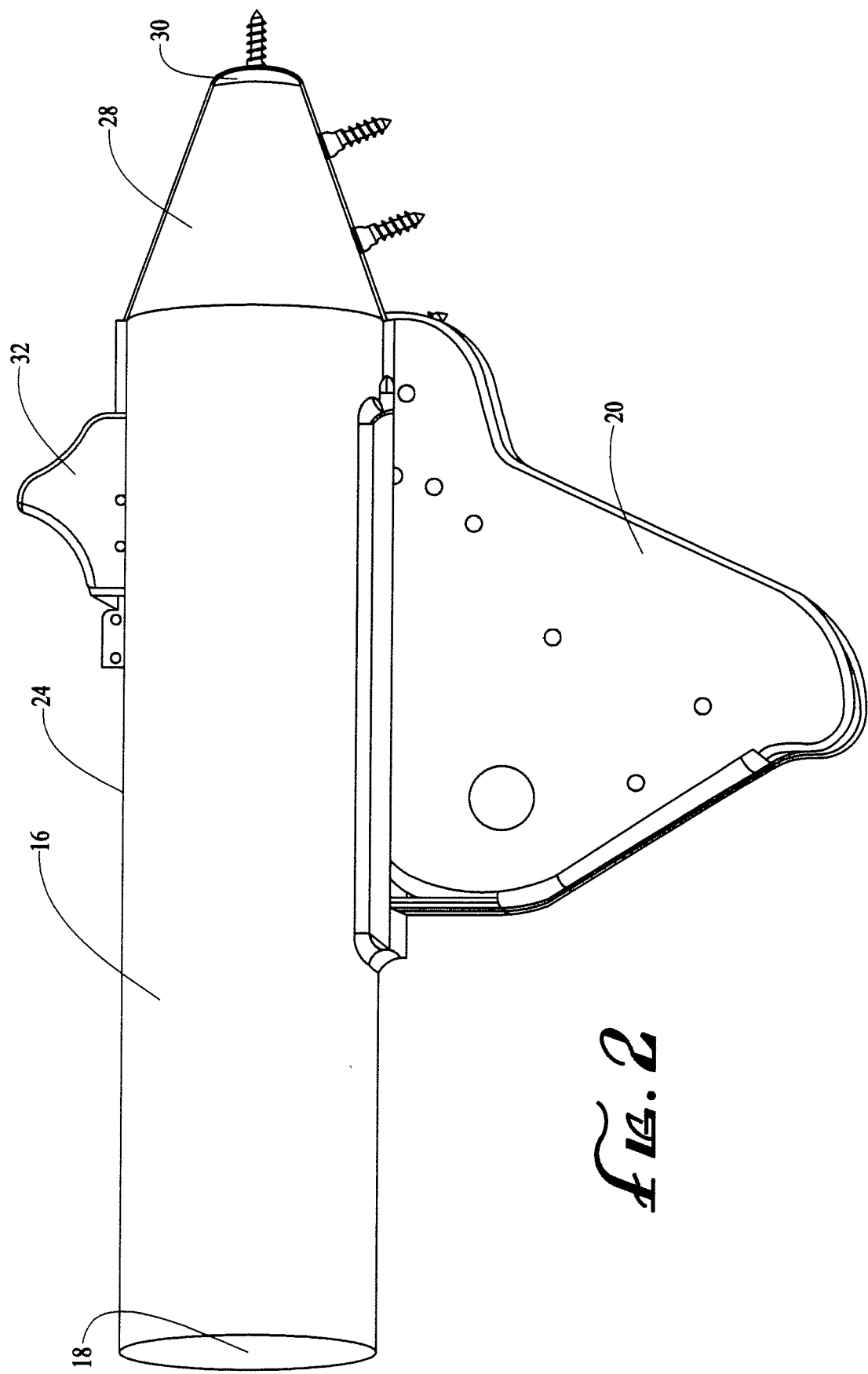
FIG. 2 is a side view of the screw delivery portion of the fastener placement system of FIG. 1.
Figure 3:
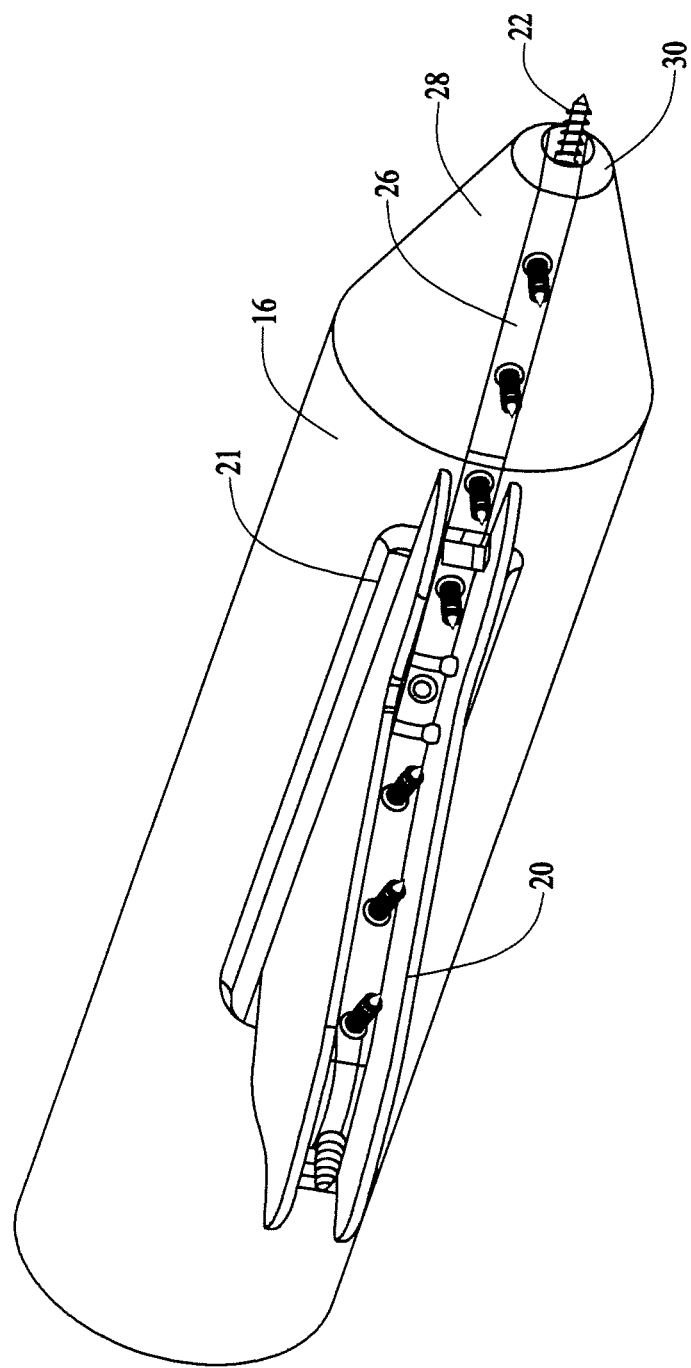
FIG. 3 is a perspective view of the lower side of the embodiment of FIG. 2 showing the fasteners in a carrying strip.
Figure 4:
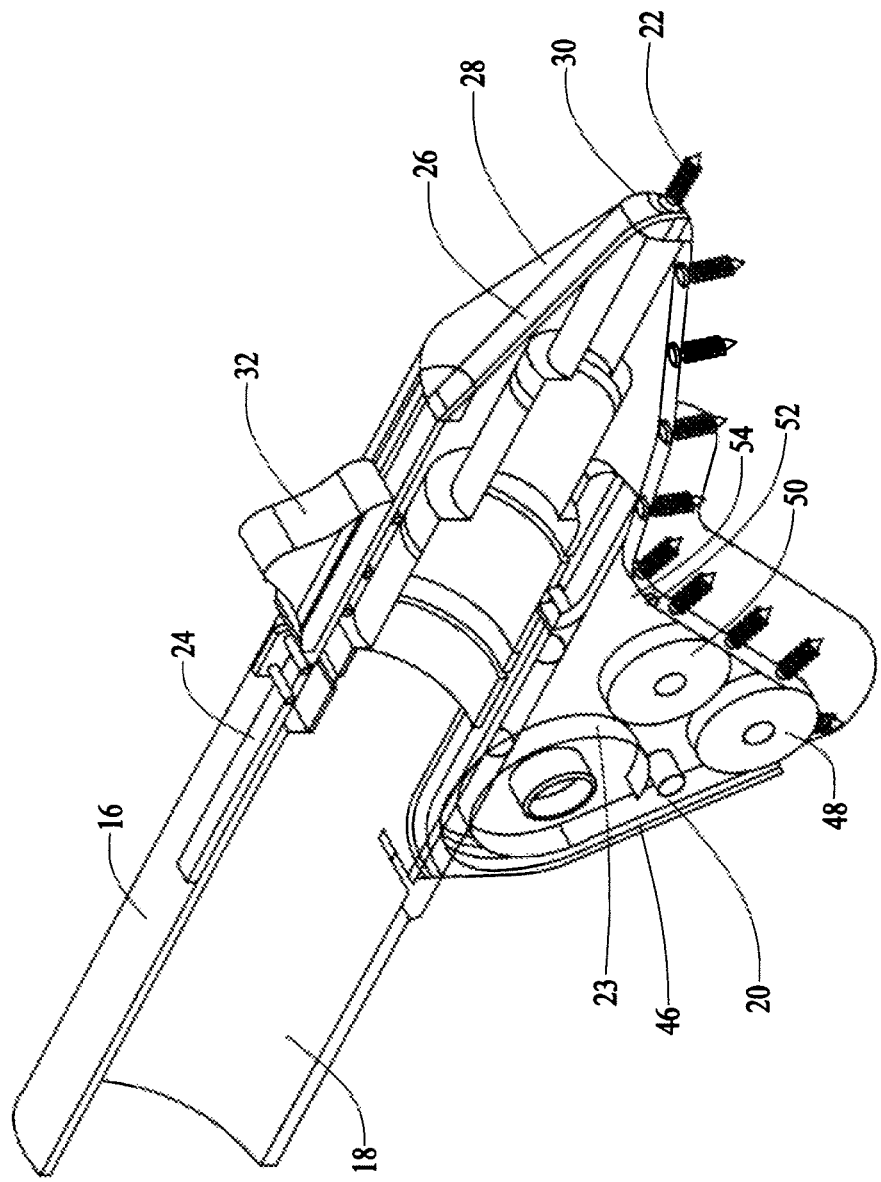
FIG. 4 is a perspective cutaway side view of the embodiment of FIG. 2 with screw fasteners placed in a band.

A perspective side view of a first embodiment of a fastener placement system 10, comprising a screw delivery portion 12 and a driver assembly 14 is shown in FIG. 1. The screw delivery portion 12, as best shown in FIGS. 2-4, comprises a cylindrical shell 16 which has a central, longitudinal opening 18 designed to receive and retain the driver assembly 14. A removable cartridge 20 carrying fasteners 22 is attached to a receiving track 21 on the lower surface of the cylindrical shell 16. The cartridge walls are preferably transparent so the user can see the quantity of fasteners remaining in the cartridge. The removable cartridge 20 is preloaded with a moveable strip 26 which carries the fasteners 22. Upon assembly for use the moveable strip 26 is extended from the removable cartridge 20 along the front portion 28 of the cylindrical shell 16, across the tip 30 of the shell 16 and rearwardly across the upper region of the front portion 28 where it is moveably connected to a trigger 32.

Figure 10:
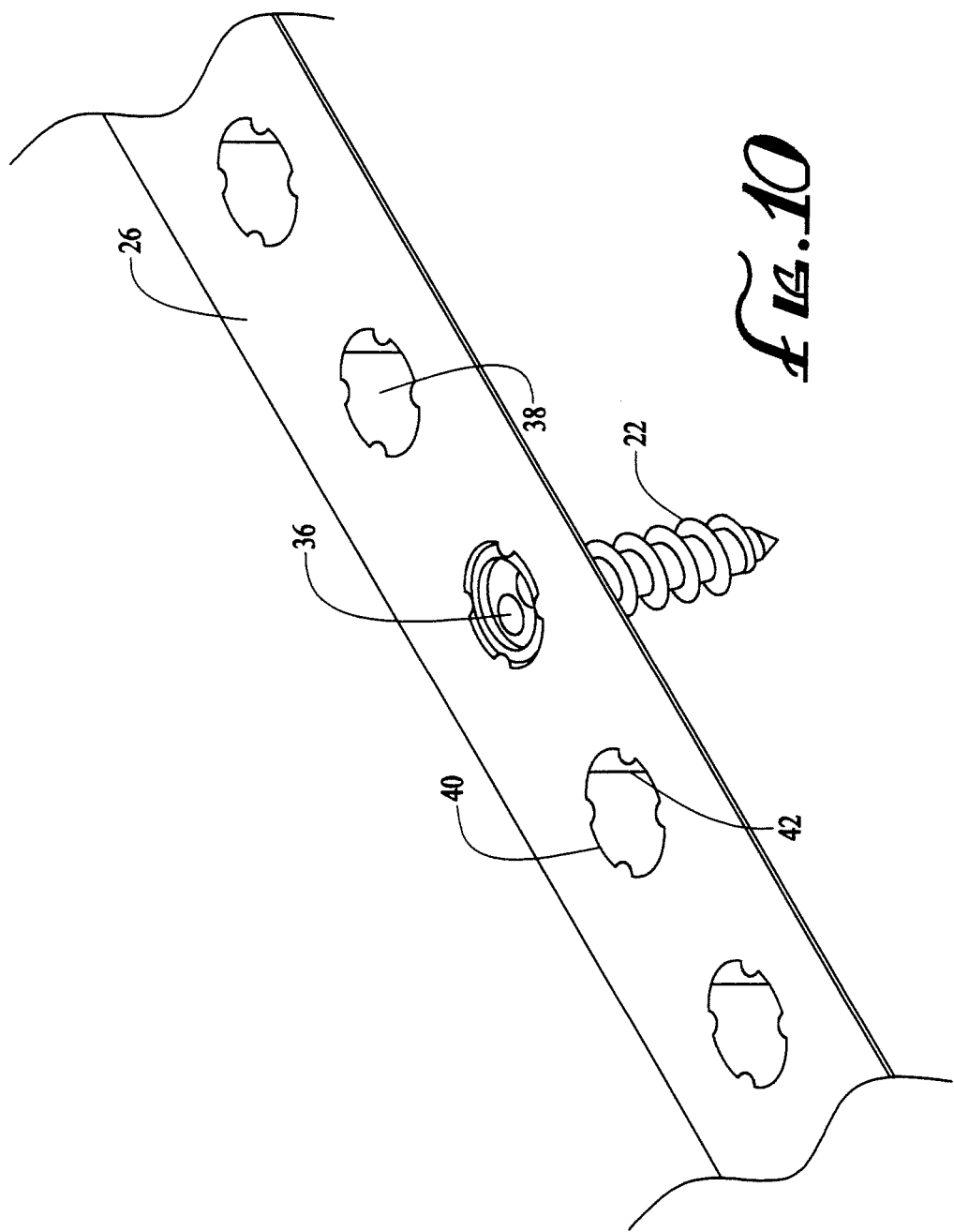
FIG. 10 is a top perspective view of the screw of FIG. 5 mounted in a first embodiment of a screw feeding band.

As shown in FIGS. 2 and 3, the fasteners 22 are temporarily and removeably attached to the elongated band or strip 26 such as shown in FIG. 10. The strip extends rearwardly beyond the last fastener 22 to provide a tail 23 for extending into the cartridge 20. A leading end 24 of the strip 26 extends forward from the front most fastener so that the strip 26 can be engaged with the under side of the trigger 32. In a preferred embodiment at least 10 fasteners 22 are attached and evenly spaced along the central portion of the strip 26. The attachment must be such that the fasteners 22 will remain in position on the strip 26 through assembly, packaging and transportation of the removable cartridge 20, installation of the cartridge 20 onto the cylindrical shell 16 and placement of the loaded strip across the tip 30 as well as movement across the front portion 28 of the cylindrical shell 16. The attachment must also be sufficient so that the driver tip 34 can engage with the head 36 of the fastener as the driver tip 34 is advanced forward. However, the temporary connection between the fastener 22 and the moveable strip 26 must also be readily disrupted thereafter by the further forward movement of the driver tip 34, the fastener 22 now temporarily and removeably carried by the driver tip 34. Typically, the fastener 22 is held in the strip 26 by a friction fit and/or horizontal or vertical extensions from the edge of mounting holes 38. Alternatively, a biocompatible glue or adhesive (not shown) could be used to temporarily secure the fastener 22 to the band 26.

Figure 11:
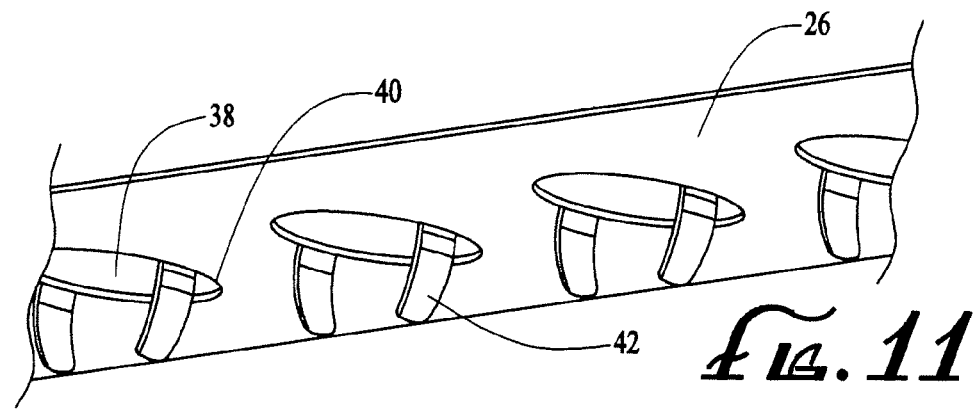
FIG. 11 is a bottom perspective view of the band of FIG. 10.
Figure 12A:
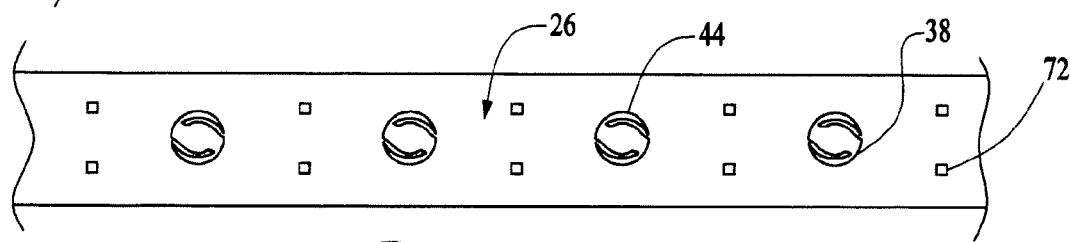
FIGS. 12-12d show several embodiments of screw retaining configurations as part of holes in a screw feeding band.
Figure 12B:
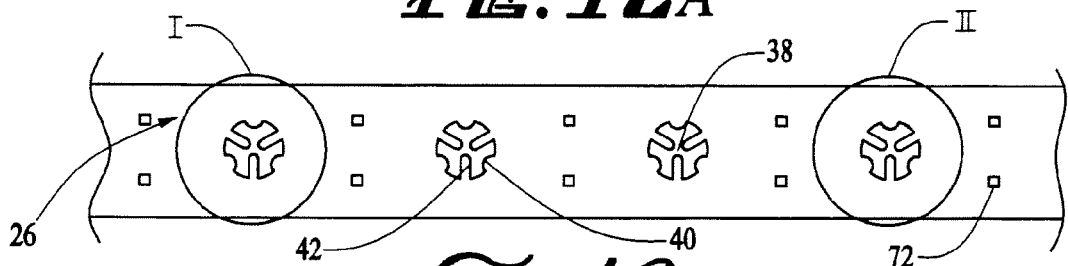
Figure 12C:
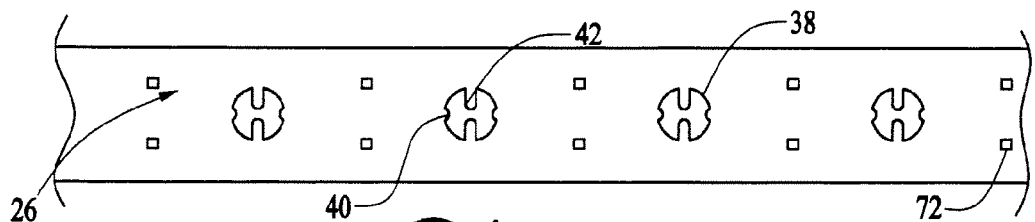
Figure 12D:
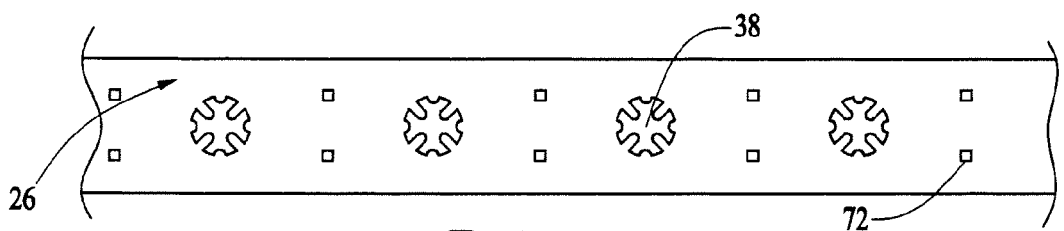

A particular embodiment illustrated in the drawings includes a hole 38 in the band with two lobes 40 extending outward from the edge of the band 26 partly across the opening of the hole 38 and two tabs 42 extending into the hole and downward from the surface. FIG. 11 is a bottom perspective view of a portion of the band or moveable strip 26 showing the tabs 42. Examples of alternative designs are shown in FIG. 12a-12d where a row of snowflake shaped openings are shown stamped or chemically etched into the band 26. In FIG. 12b one of the holes 38 is shown in its initial form (circled portion I) while another hole 38 (circled portions II of FIG. 12b demonstrates the bent down tabs 42 with inward extending lobes 40. FIG. 11c shows the embodiment of FIGS. 10 and 11. FIG. 12a shows an example of leaf spring structures 44 cut from the edge of the hole 38. The leaf spring structures 44 have a portion attached to the edge of the hole and one or two ends extending across the opening of the hole 38 to provide a spring-like grip against the side of the head 36 of the fastener 22. One skilled in the art will recognize that numerous different structures can be provided to grip the head 36 of the fastener 22.

Referring back to FIG. 4, the tail 23 on the band 26, with fasteners 22 attached to the band, extends into the cartridge 20 and through a tensioning means 46 within the cartridge. Alternatively, the tail 23 can be attached to a reel or spool which includes a tensioning spring (not shown). The band then passes over first and second guide rollers 48, 50 and behind guiding pins 52 which extend from the inner wall 54 of the cartridge 20 over the edge of the strip 26, but not far enough to contact the fasteners 20. The forward-most fastener 22 is positioned in front of the cylinder tip 30 and the leading end 24 of the strip 26 is passed under and is engaged with the trigger 32 so that when the trigger 32 retracts during use the band is moved forward placing the next available fastener 22 in position on the cylinder tip 30.

Figure 29:
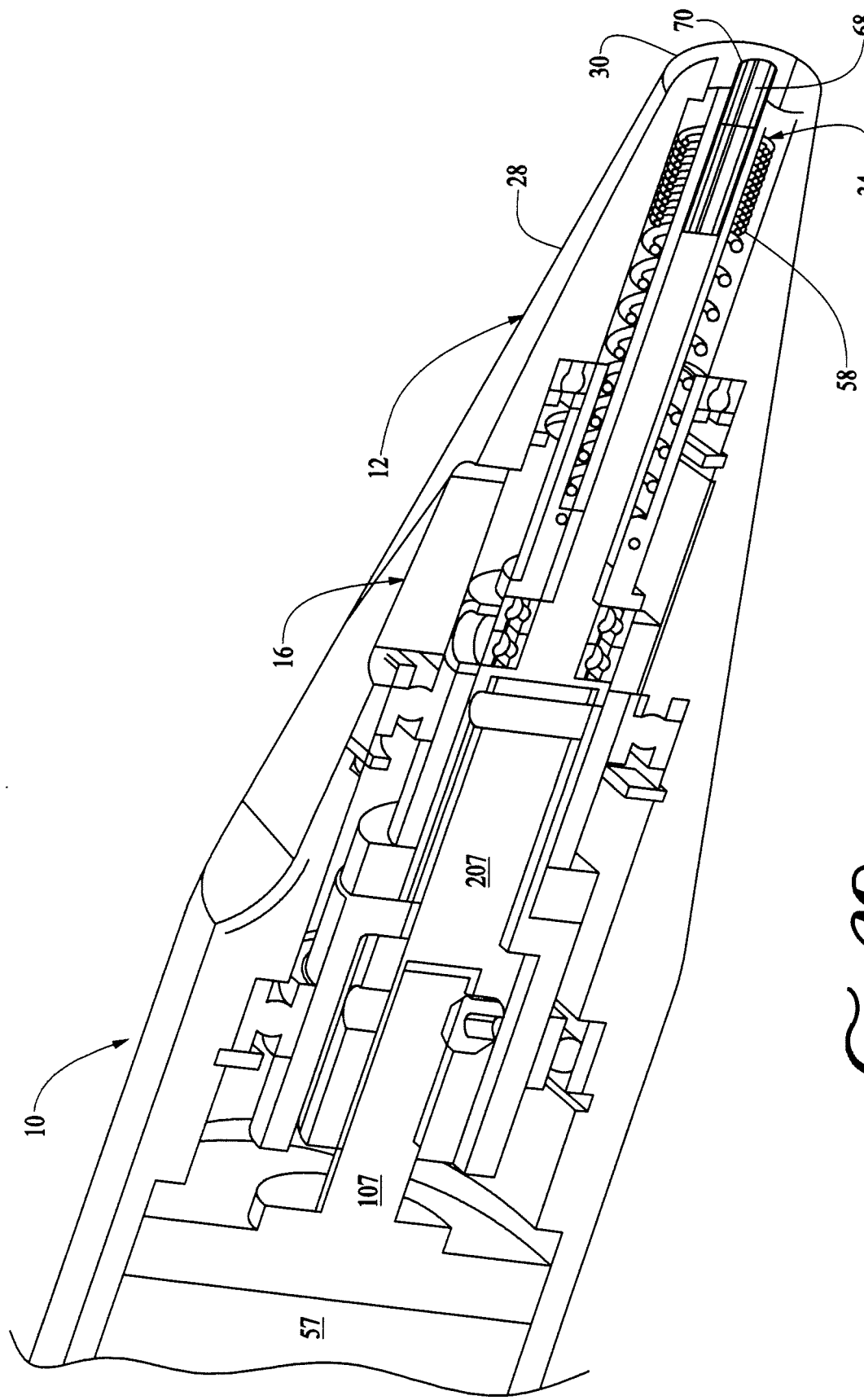
FIG. 29 is a longitudinal cross section view of the drive portion of the fastener placement system of FIG. 1.

FIG. 1 is a perspective side view and FIG. 29 is a longitudinal cross-sectional view of an embodiment of the fastener placement system 10 showing the driver assembly 14 within the screw delivery portion 12. Included within the screw delivery portion 12 is a power source, preferably a rechargeable or replaceable battery 56 which drives a motor 57, gear box 107 and drive transmission coupling 207 which in turn provides rotary motion to the driver tip 34. The motor 57 and gear assembly can include a reversing means so the tip can be rotated to insert or remove the fastener from the target bone surface. Also included are means for operatively connecting the trigger 32 on the cylinder 16 so that moving the trigger forward (toward the tip 34) also moves the driver tip 34 forward. When the trigger 32 is released a spring mechanism 58 causes the driver tip 34 to retract and, at the same time advance the strip 26, positioning the next fastener 22 for use. A separate spring (not shown) causes the pin 68 to retract.

FIGS. 5-7 show a preferred embodiment of the fastener 22 for use with the fastener placement system 10. The threaded portion 60 is similar to that on threaded fasteners currently used for medical applications. The head 36 of the fastener 22 has a recessed surface 62 which includes two radially spaced holes 64 extending perpendicular to the recessed surface 62. These holes are sized to receive two like-sized and shaped driver pins 68 which extend from and retract into the driver tip 34. While the driver pins 68 are preferably sized and shaped like the holes, they can be of any shape as long as they fit in the holes. Also, the holes 64 do not have to be round but can be of any shape and in fact can each be a different shape. The wall of the head 36 of the fastener 22 extending above the recessed surface 62 has a taper 66 extending inwardly from the top down, as best shown in FIG. 6a. FIGS. 8 and 9 show a similar shaped outwardly extending portion or flange 70 on the driver tip 34. The flange 70, being slightly larger than the top of the taper 66, allows the driver tip 34 to be inserted into the head of the fastener 22 and grasp the fastener head 36, interlocking with the head 36 of the fastener 22, as shown in FIG. 30 to separate the fastener from the strip 26.

To use the fastener placement system 10 a loaded cartridge 20 is slid into track 21 on the lower wall of the cylindrical shell 16, the moveable strip 26 is placed over the front portion 28 and across the tip 30. A first fastener 22 is positioned extending outward from the tip 30. The leading edge 24 is fed under the trigger 32. The trigger 32 is manually advanced toward the tip 30, which causes power from the battery 56 to be delivered to the motor 57, causing the tip 34 to rotate and to move forward toward the fastener head 36. Continued forward movement causes the flange 70 to enter the head of the fastener and interlock with the taper 66 while at the same time the driver pins 68 are extended into the holes 64 in the head of the fastener 22. Substantially simultaneously with the flange 70 and taper 66 grasping each other and the pins 68 entering the holes 64 the fastener 22 becomes detached from the strip 26. The driver tip 34, with the rotating fastener 22 attached thereto, now extends through the mounting hole 38 and the rotating fastener 22 can be applied to the bone surface for securing the bone pieces together. Releasing the trigger 32 allows spring 58 to exert rearward motion on the driver tip 34. The separate springs (not shown) also cause the pins 68 to retract, the driver tip 34 to separate from the fastener head 36 and the rotation of the driver tip 34 to cease. As the trigger moves back to its resting position extensions on the bottom of the trigger (not shown) set into drive holes 72 spaced along the edge of the band 26, grasping the band and causing the leading edge 24 to move rearward, which positions the next fastener 22 in front of the cylinder tip 30 and driver tip 34 so that the above described action can be repeated.

Figure 13A:
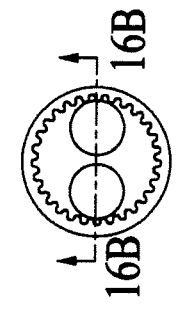
FIGS. 13a and 13b, 14a and 14b, 15a and 15b, and 16a and 16b show several additional embodiments of screw head constructions which provide structure within the screw head for grasping the fastener.
Figure 14A:
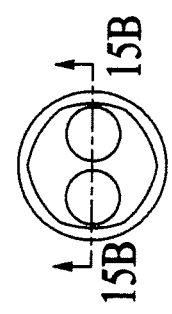
Figure 15A:
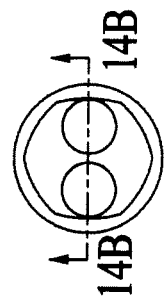
Figure 16A:
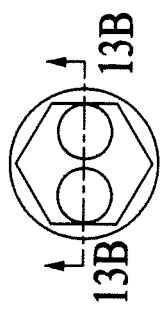
Figure 13B:
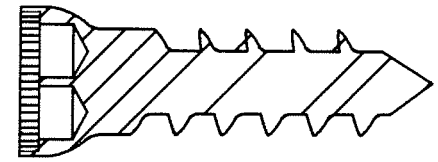
Figure 14B:
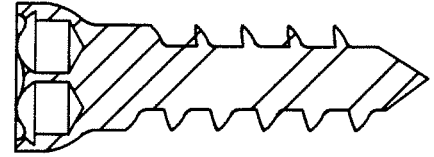
Figure 15B:
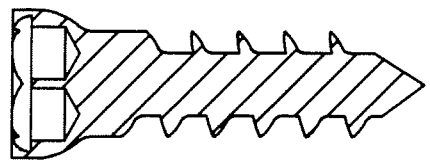
Figure 16B:
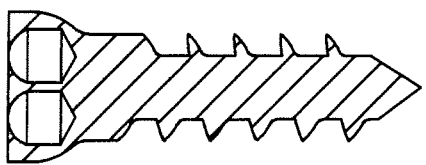
Figure 23A:
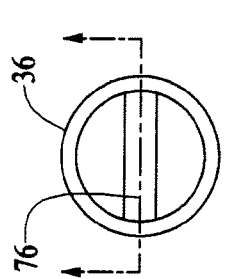
FIGS. 23a and b, 24a and b, 25a and b, and 26a and b are top and cross-sectional views respectively of further embodiments of the fastener including extensions from the head of the fastener in place of holes in the head.
Figure 23B:
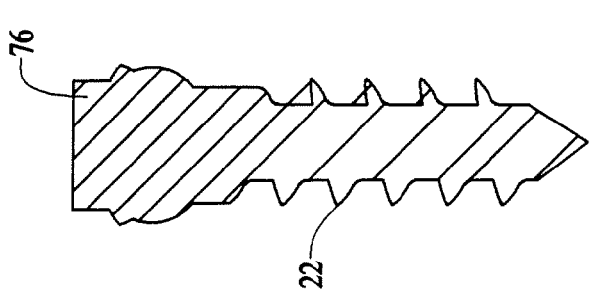
Figure 24A:
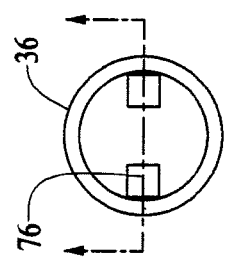
Figure 24B:
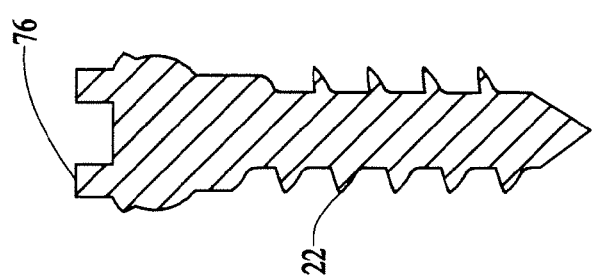
Figure 25A:
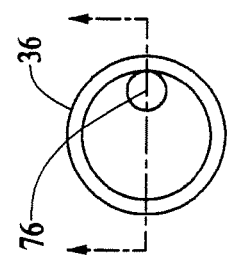
Figure 25B:
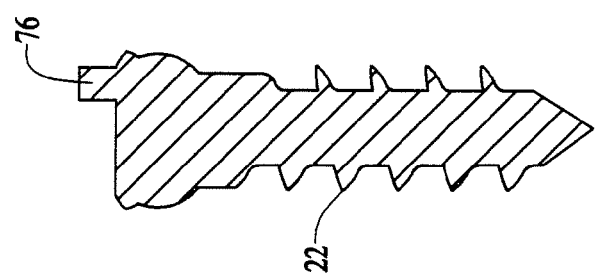
Figure 26A:
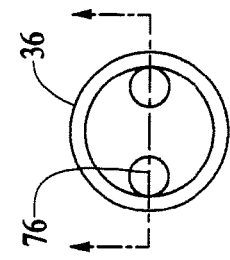
Figure 26B:
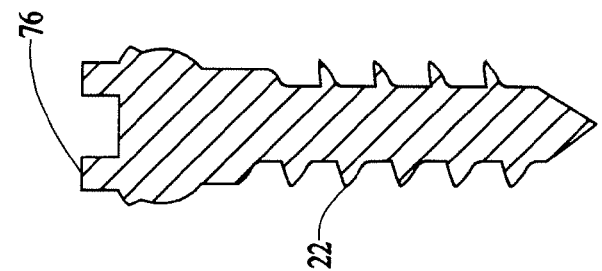
Figure 28:
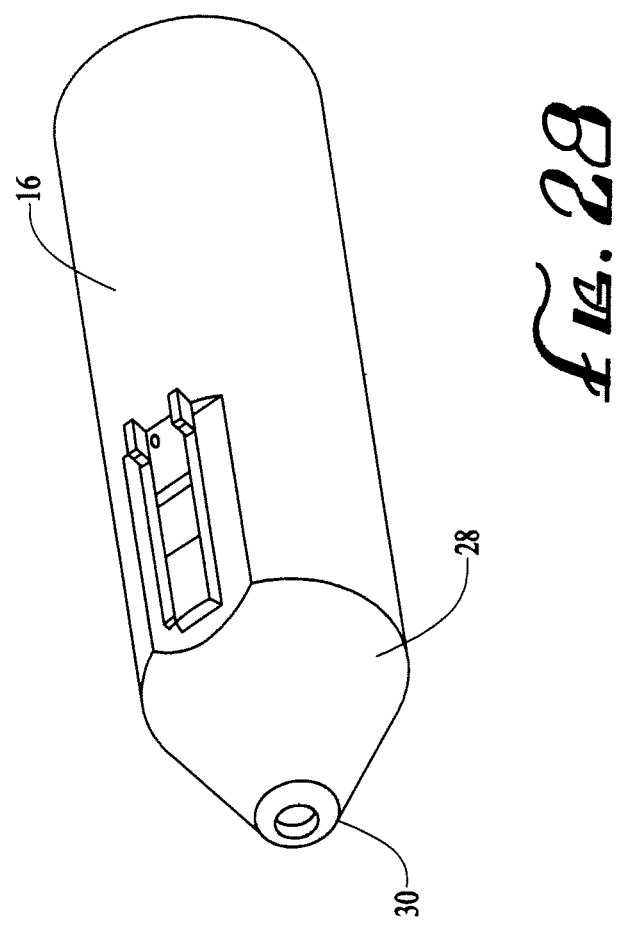
FIG. 28 is a top perspective view of the screw delivery portion showing the tape receiving rack with the advancement trigger removed.

While the above described embodiment describes two pins 68 that insert into holes 64 in the fastener head 36 one or more geometric shaped holes or slots in the head of the fastener 22, and matching structure on the driver tip 34 can be used to accomplish the same screw placement function. Alternative interacting hole or holes 64 and driver tip 34 include numerous common structures used on the head of screws and bolts including but not limited to Phillips head, Allen wrench, slots and other geometric shapes as shown in FIGS. 12-21a. FIGS. 13-16 show some alternative designs for the fastener head structure. While FIG. 7 shows a circular top inner edge on the recess, other non-circular or modified circular designs may be used. FIGS. 13-16a and b are top and cross-sectional views of four alternatives. FIGS. 16a and b show a fastener 34 with a round, serrated edge 67 to aid in grasping the fastener for rotation. FIGS. 13a and b show an upper inner edge with six sides, but other geometric shapes can be used. FIGS. 14 and 15 show rounded variations of the design of FIG. 13.

FIGS. 17-21a, b and c show top, cross sectional and side views of five alternative embodiments with different shaped hole 64 structures in the head 36 of the fastener 22. As best shown in FIGS. 17-21c, these fasteners 22 also have a taper 66 on the outer surface of the head 32 which can be grabbed by inwardly extending portion 74 on a driver tip 34 as shown in FIG. 22. FIGS. 23-26a and b are top and longitudinal cut-away views of still further embodiments which show extensions 76 from the head 36 of the fastener. The driver pins 68, instead of sitting into holes 64 in the head 36 of the fastener 22 are structured to grasp or surround the extensions 76. One skilled in the art will recognize that a combination of holes 64 and extensions 76 can also be used.

FIG. 31 shows an alternative band 126 which has an upper band 128, which holds the fastener 22 in a manner as described above, and a lower band 130 to aid in aligning the fastener. The lower band 130 also has holes there through which have a diameter greater than the head 36 of the fastener 22 so the fastener will pass through without bending. Also shown is the driver tip (with the cylindrical shell 16 not shown). The upper band 128 and lower band 130 are connected by posts 132. To allow the two layer band to wrap around curves, the lower band 130 has slits 134 across the width.

FIG. 32 is a perspective side view of a second embodiment of a fastener placement system 100, comprising a screw delivery portion 102 and a driver assembly 104 is shown in FIG. 32. The screw delivery portion 102, also shown in FIGS. 33 and 34, comprises a cylindrical shell 106 which has a central, longitudinal opening 108 designed to receive and retain the driver assembly 104. A removable cartridge 120 carrying fasteners 122 is attached to a receiving track 121 on the lower surface of the cylindrical shell 116. The cartridge walls are preferably transparent so the user can see the quantity of fasteners remaining in the cartridge. The removable cartridge 120 is preloaded with a moveable strip 126 which carries the fasteners 122. Upon assembly for use the moveable strip 126 is extended from the removable cartridge 20 along the front portion 128 of the cylindrical shell 116, across the tip 130 of the shell 116 and rearwardly across the upper region of the front portion 128 where it is moveably connected to a trigger 132. One difference between the embodiment of FIG. 32 and the embodiment of FIG. 1 is that the second embodiment has the trigger 132 located on the right side of the device. This was found to be more ergonomically favorable for operation then the top mounted trigger 32 of the first embodiment, particularly for a right handed operator. A further embodiment with the trigger on the left side for use by left handed individuals (not shown) can also be provided or the trigger 132 can be constructed with both a right and a left side trigger which provides ease of operation using either the right or the left hand.

Figure 33:
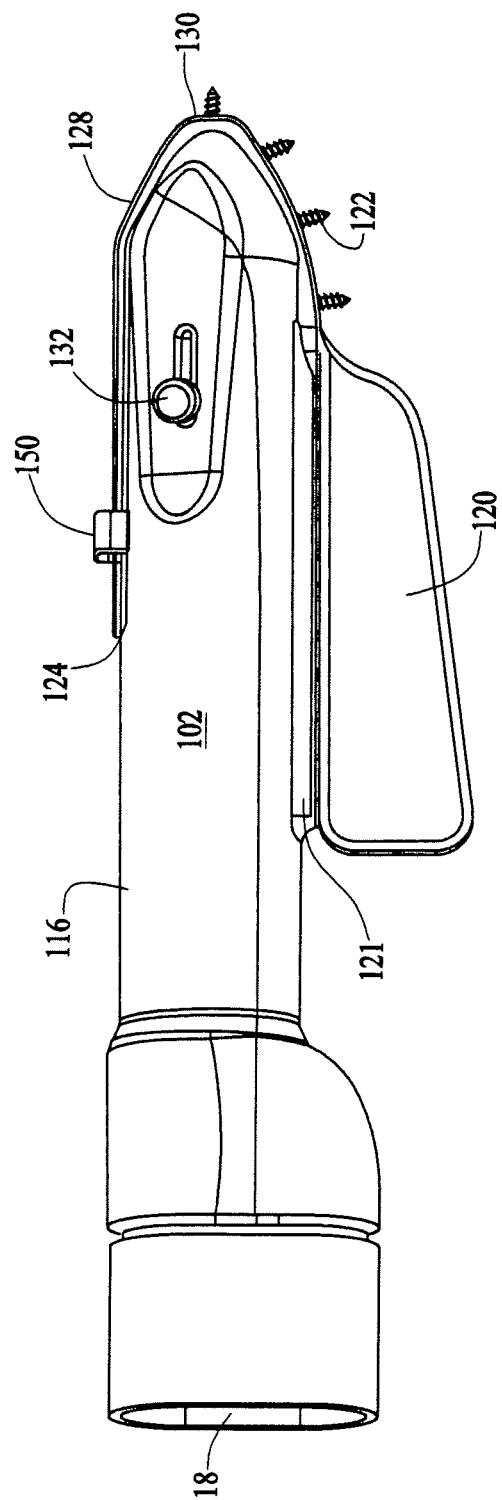
FIG. 33 is a side view of the screw delivery portion of the fastener placement system of FIG. 32.

As shown in FIGS. 33 and 34, the fasteners 122 are temporarily and removeably attached to the elongated band or strip 126 in the same manner as shown in FIG. 10. The strip extends rearwardly beyond the last fastener 122 to provide a tail (not shown) for extending into the cartridge 120. A leading end 124 of the strip 126 extends forward from the front most fastener so that the strip 126 can be engaged with structure attached to the trigger 132 within the fastener placement system 100. In a preferred embodiment at least 10 fasteners 122 are attached and evenly spaced along the central portion of the strip 126. The attachment must be such that the fasteners 122 will remain in position on the strip 126 through assembly, packaging and transportation of the removable cartridge 120, installation of the cartridge 120 onto the cylindrical shell 116 and placement of the loaded strip across the tip 130 as well as movement across the front portion 128 of the cylindrical shell 116. The attachment must also be sufficient so that the driver tip (not shown) can engage with the head 36 of the fastener 122 as the driver tip is advanced forward. However, the temporary connection between the fastener 122 and the moveable strip 126 must also be readily disrupted thereafter by the further forward movement of the driver tip, the fastener 122 now temporarily and removeably carried by the driver tip. Typically, the fastener 122 is held in the strip 126 by a friction fit and/or horizontal or vertical extensions from the edge of mounting holes 38. Alternatively, a biocompatible glue or adhesive (not shown) could be used to temporarily secure the fastener 122 to the band 126. Other components of the second embodiment not shown in FIGS. 32-34 are the same as in the first embodiment.

To use the fastener placement system 100 a loaded cartridge 120 is slid into track 121 on the lower wall of the cylindrical shell 116, and the moveable strip 126 is placed over the front portion 128 and across the tip 130. A first fastener 122 is positioned extending outward from the tip 130. The leading edge 124 is fed under a retainer clip 150. The trigger 132 is manually advanced toward the tip 130, which causes power from the battery 56 to be delivered to the motor 57, causing the tip 134 to rotate and to move forward toward the fastener head 36. Continued forward movement causes the flange 70 to enter the head of the fastener 122 and interlock with the taper 66 while at the same time the driver pins 68 are extended into the holes 64 in the head of the fastener 122. Substantially simultaneously with the flange 70 and taper 66 grasping each other and the pins 68 entering the holes 64 the fastener 122 becomes detached from the strip 126. The driver tip 34, with the rotating fastener 122 attached thereto, now extends through the mounting hole 38 and the rotating fastener 122 can be applied to the bone surface for securing the bone pieces together. Releasing the trigger 132 allows a spring to exert rearward motion on the driver tip 134. The separate springs (not shown) also cause the pins 68 to retract, the driver tip 34 to separate from the fastener head 36 and the rotation of the driver tip 34 to cease. As the trigger 132 moves back to its resting position extensions from the trigger (not shown) interact with drive holes 72 spaced along the edge of the band 126, grasping the band and causing the leading edge 124 to move rearward, which positions the next fastener 122 in front of the tip 130 and driver tip 34 so that the above described action can be repeated.

Other embodiments of the invention can comprise different fastener carrier arrangements such as a cartridge to carry the fasteners. One such preferred embodiment uses a rotating cartridge including multiple chambers. The cartridge can be either removable from or permanently attached to the fastener system. Further, the cartridge can be a fully pre-loaded disposable cartridge or a customer-loaded reusable cartridge.

The fasteners are preferably held in a specified orientation within each chamber of the rotating cartridge. Different embodiments of the invention can comprise different structures for holding the fasteners in this specified orientation. One preferred embodiment of the fastener system comprises at least one cantilever to hold a fastener in place. Another preferred embodiment comprises a spring system to hold a fastener in place. A third preferred embodiment comprises molded collars, either permanently or temporarily attached to the chamber or to the fastener, to hold the fastener in place. However, one skilled in the art, based on the teachings here, will recognize that numerous different structures can be used to retain the fasteners in the cartridge.

A particular advantage of preferred embodiments is that the fasteners are secured to the driver tip when removed from the carrier, but are readily released from the driver tip once placed in the bone or tissue in the surgical site. Different embodiments of the invention can comprise different structures or apparatus for performing this function. One preferred embodiment comprises a hook system within the hole or holes of the fastener head to which the driver tip engages. In some embodiments the hooks can either fully or partially rotate with the force of the driver tip and latch onto a feature on the driver tip head. Another preferred embodiment of the fastener system can comprise molded pieces within the screw head to perform this function. An example of such a retaining structure is illustrated by a fastener head with two holes therein to be engaged by a two-pronged driver tip. However, such a fastener and driver tip combination can be replaced by any of the previously described fastener and driver tip combinations, including a single driver tip.

Figure 35A:
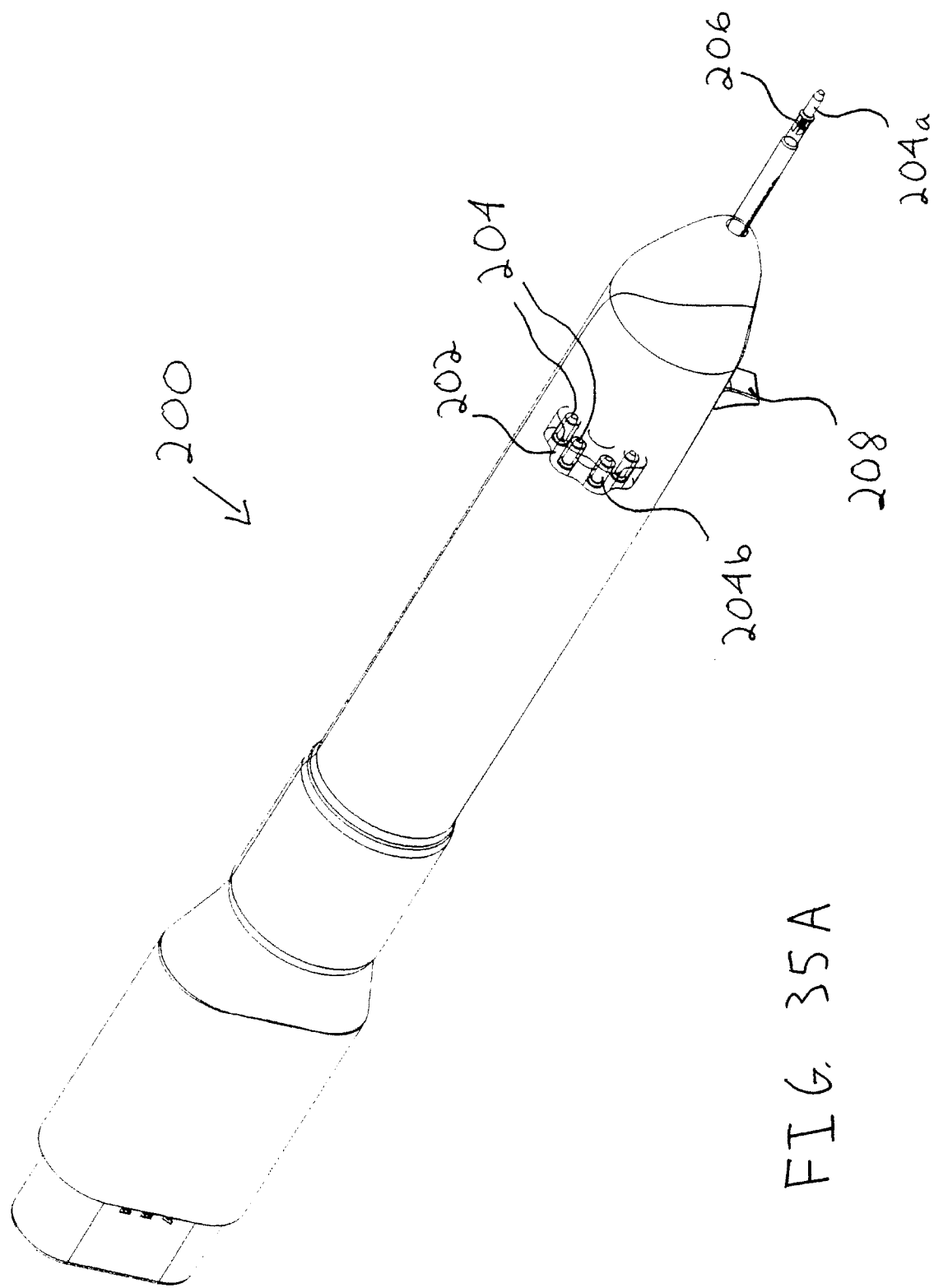
FIGS. 35A, B, and C are perspective, front, and side views of another embodiment of a fastener placement system incorporating features of the invention.
Figure 35B:
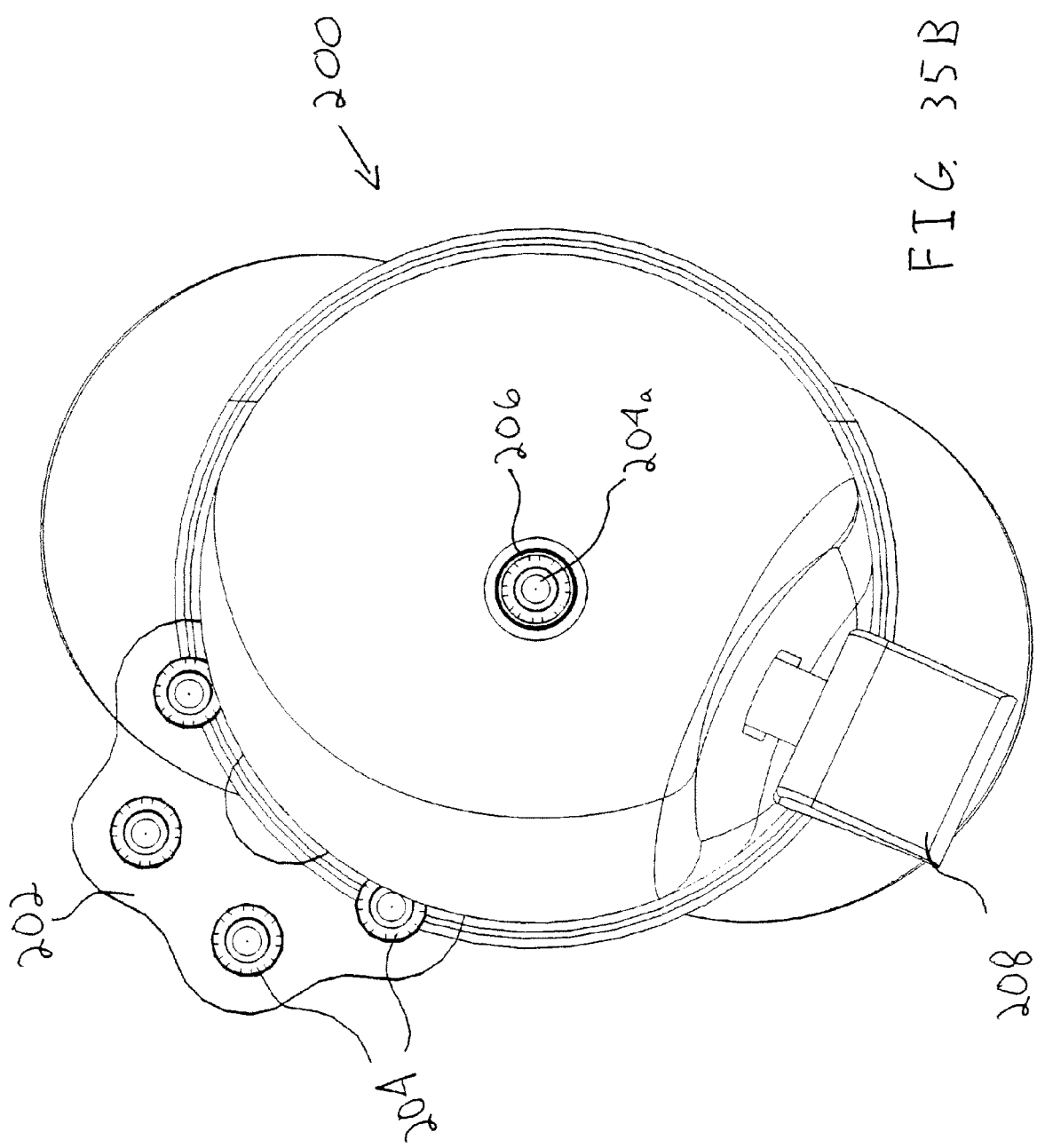
Figure 35C:
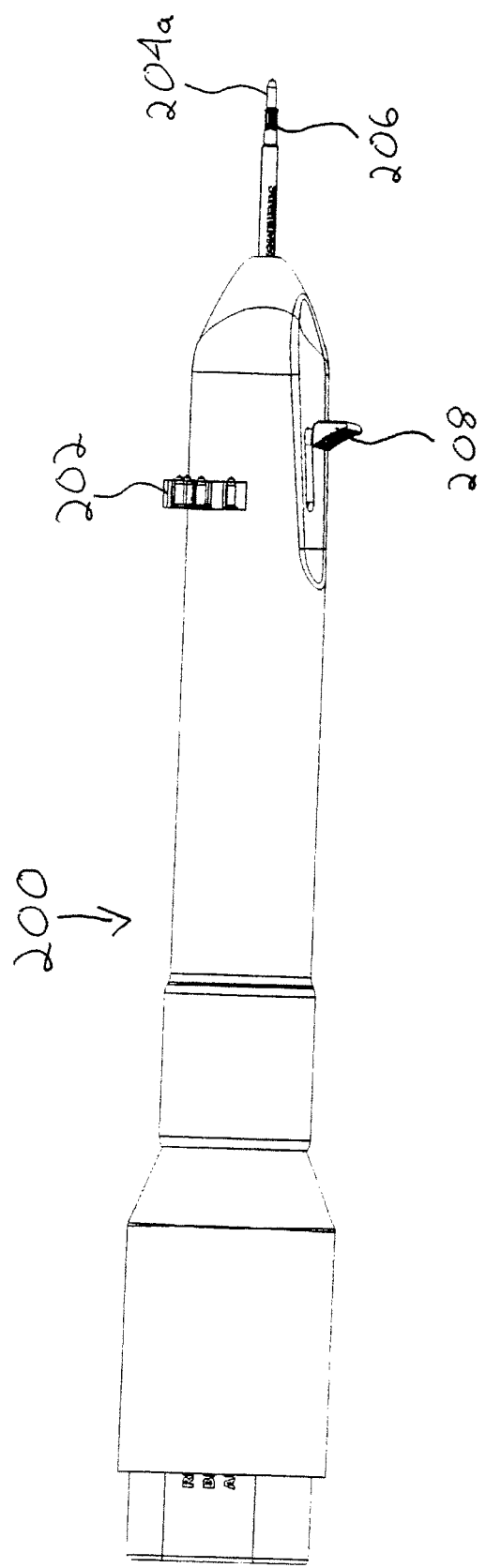

FIG. 35A, FIG. 35B, and FIG. 35C show a perspective view, front view, and side view, respectively, of a preferred embodiment comprising elements of the invention. The embodiment of FIG. 35A, FIG. 35B, and FIG. 35C comprises fasteners 204 (labeled 204a and 204b to illustrate the multiple fasteners in two different locations) in a cartridge fastener placement system 200 and trigger 208. As shown, the fastener 204a is attached to a driver tip 206. The embodiment of FIG. 35A, FIG. 35B, and FIG. 35C also comprises a cartridge 202. In this embodiment, cartridge 202 is a six-chamber cartridge. Cartridge 202 temporarily and removably holds fasteners 204b.

Figure 36A:
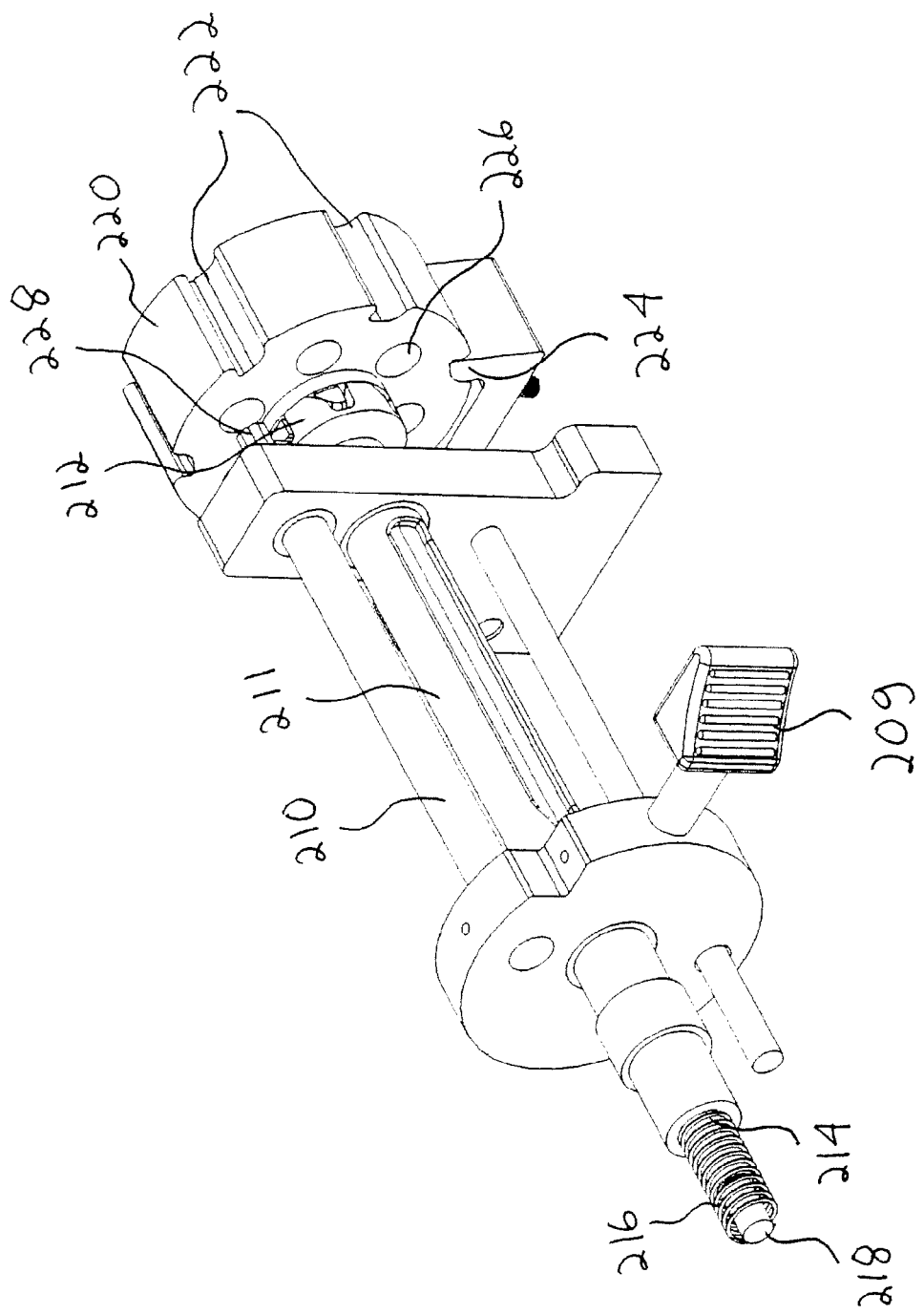
FIGS. 36A, B, and C are perspective, front, and side views of the inner mechanisms of an embodiment of a fastener placement system incorporating features of the invention.
Figure 36B:
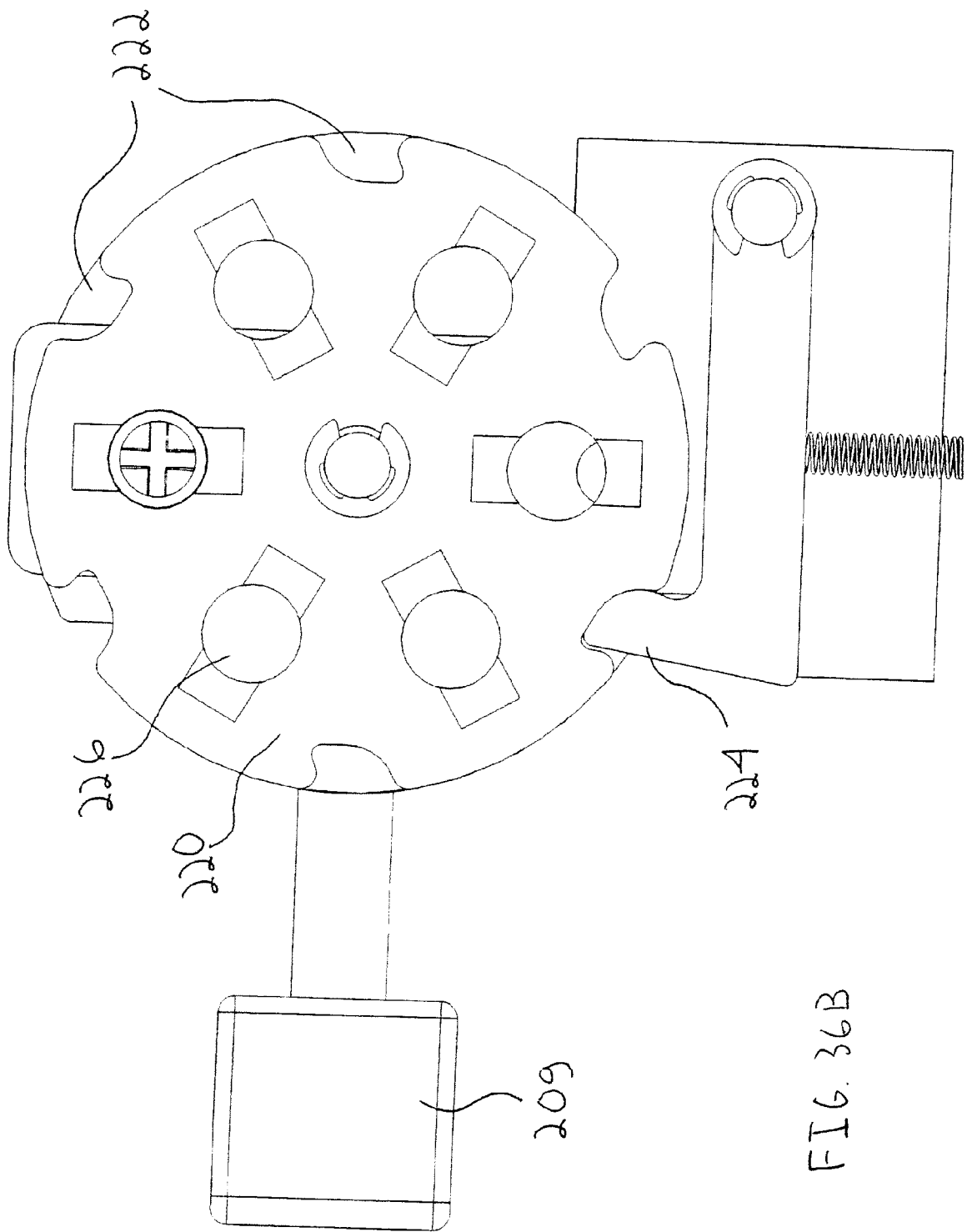
Figure 36C:
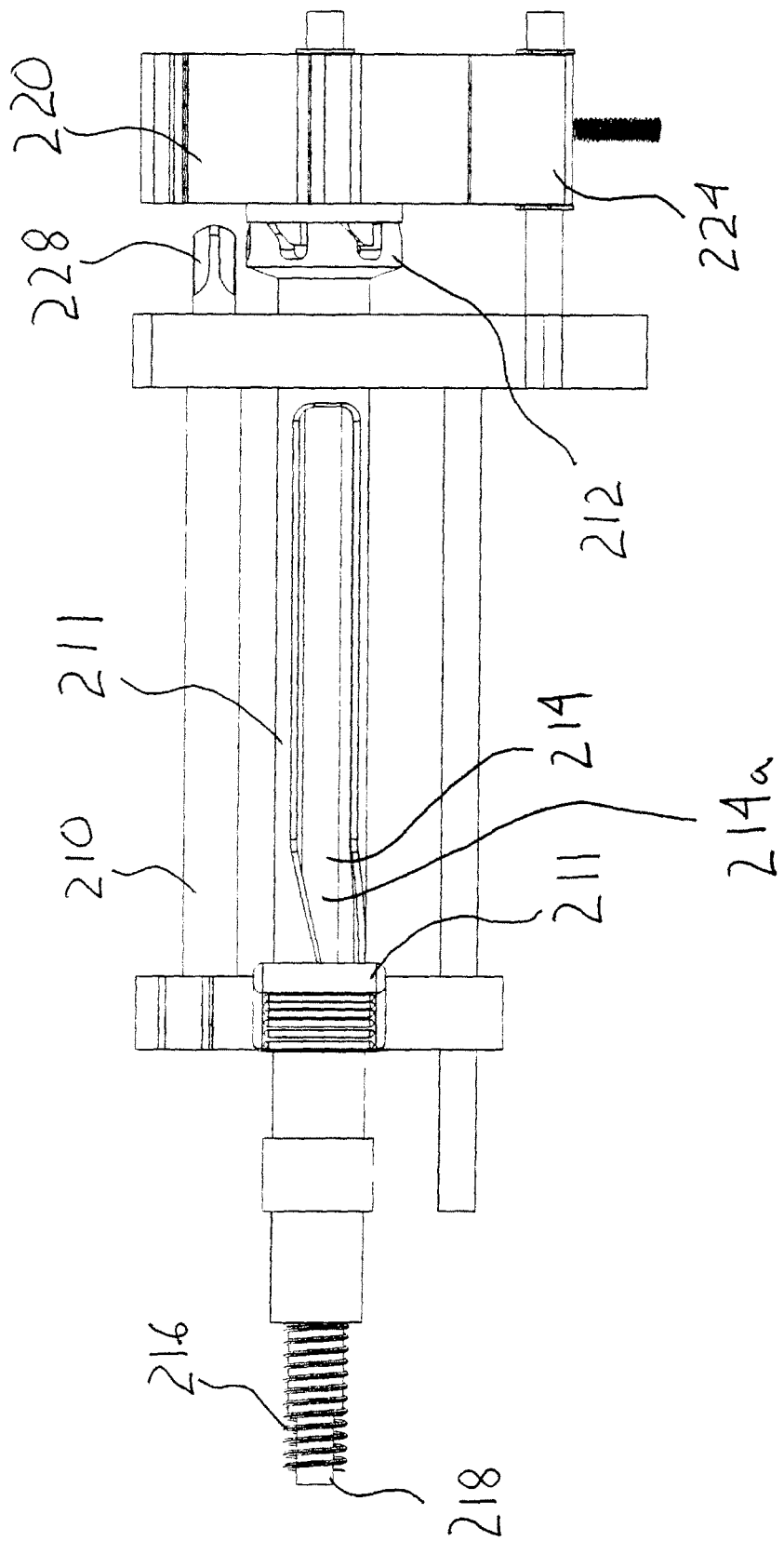

FIG. 36A, FIG. 36B, and FIG. 36C show a perspective view, front view, and side view, respectively, of the internal mechanisms of one embodiment of the invention. In this embodiment, unlike that of FIG. 35A, FIG. 35B, and FIG. 35C, the empty cartridge 220 is centered longitudinally with the drive shaft 210. In one embodiment, cartridge 220 rotates using an indexing mechanism that translates a linear motion into a rotational motion.

FIG. 36A, FIG. 36B, and FIG. 36C show some of the internal mechanisms of a device according to an embodiment of the present invention in the cocked position, meaning that the drive shaft 210 is static. The device comprises a longitudinal slot 214 running inside main index drive shaft 211 which itself comprises a main index drive shaft head 212. The main index drive shaft head can be integral to the main index drive shaft 211, or can be connected such that the main index drive shaft head 212 and the main index drive shaft 211 can at some times rotate independently or at the same time. Slot 214 comprises a longitudinal helix 214a, and a slot index drive shaft 218 occupies an area within the helix 214a. While the FIG. 36A, FIG. 36B, and FIG. 36C embodiment comprises a helix, other embodiments may comprise other three dimensional shapes that can cause rotational movement. As the device is engaged, the slot index drive shaft 218 moves forward longitudinally. As the slot index drive shaft 218 moves forward it encounters the helix 214*a*, which is attached to the main index drive shaft 211. The forward movement of slot index drive shaft 218 as influenced by the shape of the helix 214*a*, which is connected to the main index drive shaft 211, causes the main index drive shaft 211 to rotate. Spring 216 serves to reposition the main index drive shaft 211 after the shaft is pulled backwards through the operation of trigger 209.

Cartridge 220 comprises multiple notches 222. The device also comprises a spring-loaded lever 224, which occupies one notch 222 when the device is in the cocked position. As the device is engaged, slot index drive shaft 218 encounters helix 216, forcing the main index drive shaft 211 to rotate. The main index drive shaft head 212 is connected to the cartridge 220, also causing the cartridge 220 to rotate. As the cartridge 220 rotates, lever 224 is forced out of the notch 222. As the cartridge 220 rotates further, the spring-loaded lever 224 pushes against the circumference of the cartridge 220 until the lever 224 encounters another notch 222*b*. The spring-loaded lever 224 then moves into the next notch 222 such that a fastener (not shown) in the chamber 226 is in position to receive the driver tip 228. When loaded, the chamber 226 holds a fastener in a position such that driver tip 228 can engage the fastener head. The driver tip 228 can then temporarily interlock with and carry the fastener until it is deposited into the surgical site. The driver tip 228 then disengages the fastener head, and the drive shaft 210, main index drive shaft 211, and slot index drive shaft 218 return to the cocked position. In one embodiment, the shape of the lever 224 holds the cartridge 220 in place. The main index drive shaft 211 can then either be held rotationally in place as it retracts, or can rotate in a direction opposite that of the rotation during the forward movement to return to its original rotational position. In the embodiment shown in FIG. 36A, FIG. 36B, and FIG. 36C, the cartridge 220 and the chamber 226 are rotated during the forward movement of the drive shaft 210, in other embodiments the rotation can occur after the driver tip 228 has exited the chamber 226 on the way back to the cocked position.

Figure 37A:
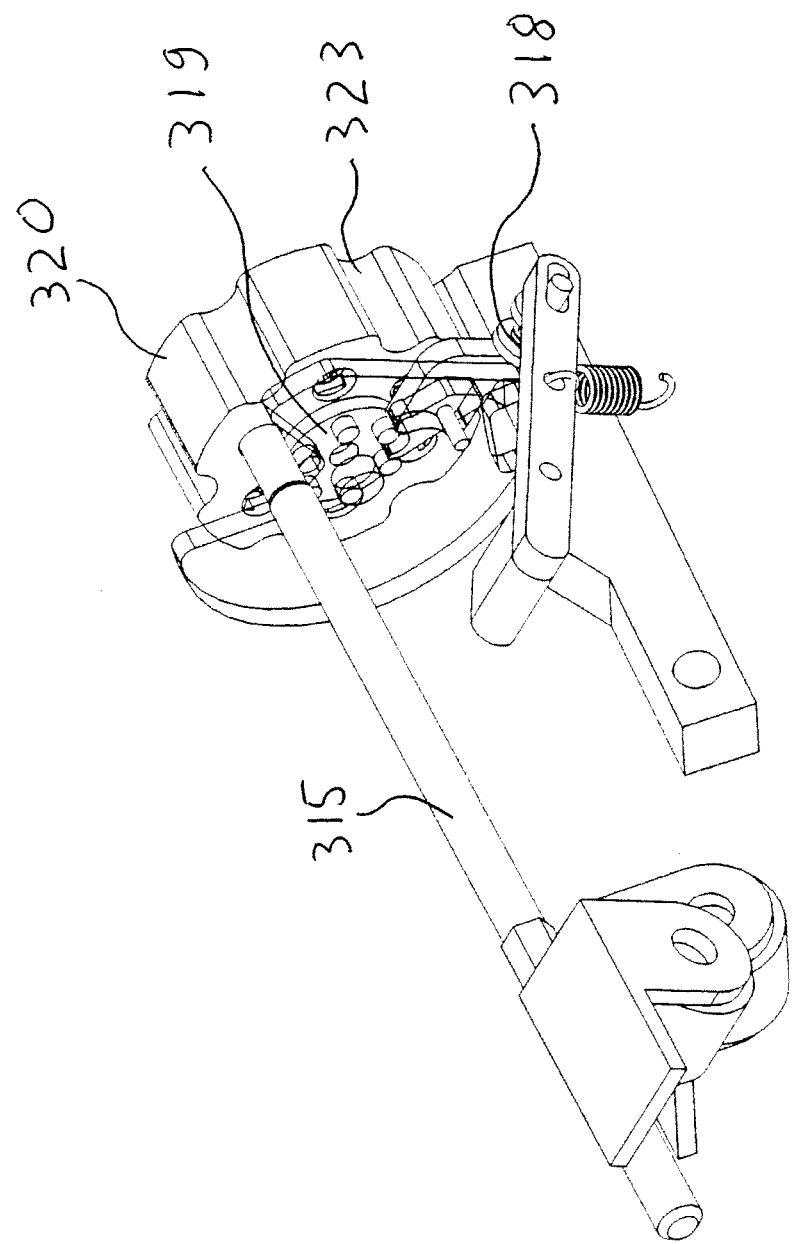
FIGS. 37A, B, and C are perspective, front, and side views of the inner mechanisms of another embodiment of a fastener placement system incorporating features of the invention.
Figure 37C:
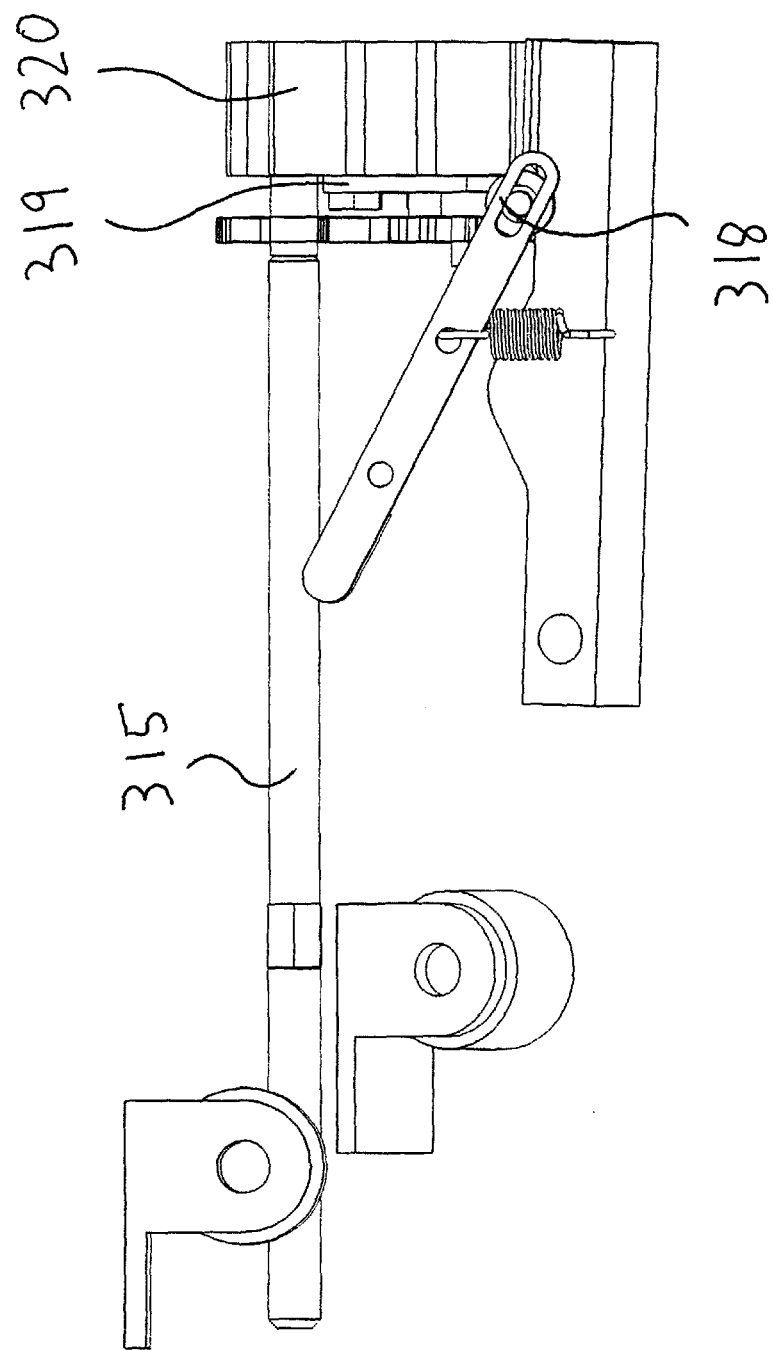

FIG. 37A, FIG. 37B, and FIG. 37C show perspective, front, and side views of internal mechanisms of a device according to another embodiment of the present invention. As the drive shaft 315 moves forward laterally, the device 318 engages the raised surfaces 319 of the cartridge 320, causing a chamber 321 to rotate into place such that a fastener 322 is properly positioned for engagement by the driver tip (not shown). The embodiment of FIG. 37A, FIG. 37B, and FIG. 37C also comprises notches 323 and a lever 324 to assist in the positioning process. Other embodiments comprising elements of the invention can comprise some of these positioning systems, all of these positioning systems, different positioning systems, or combinations thereof.

Figure 38A:
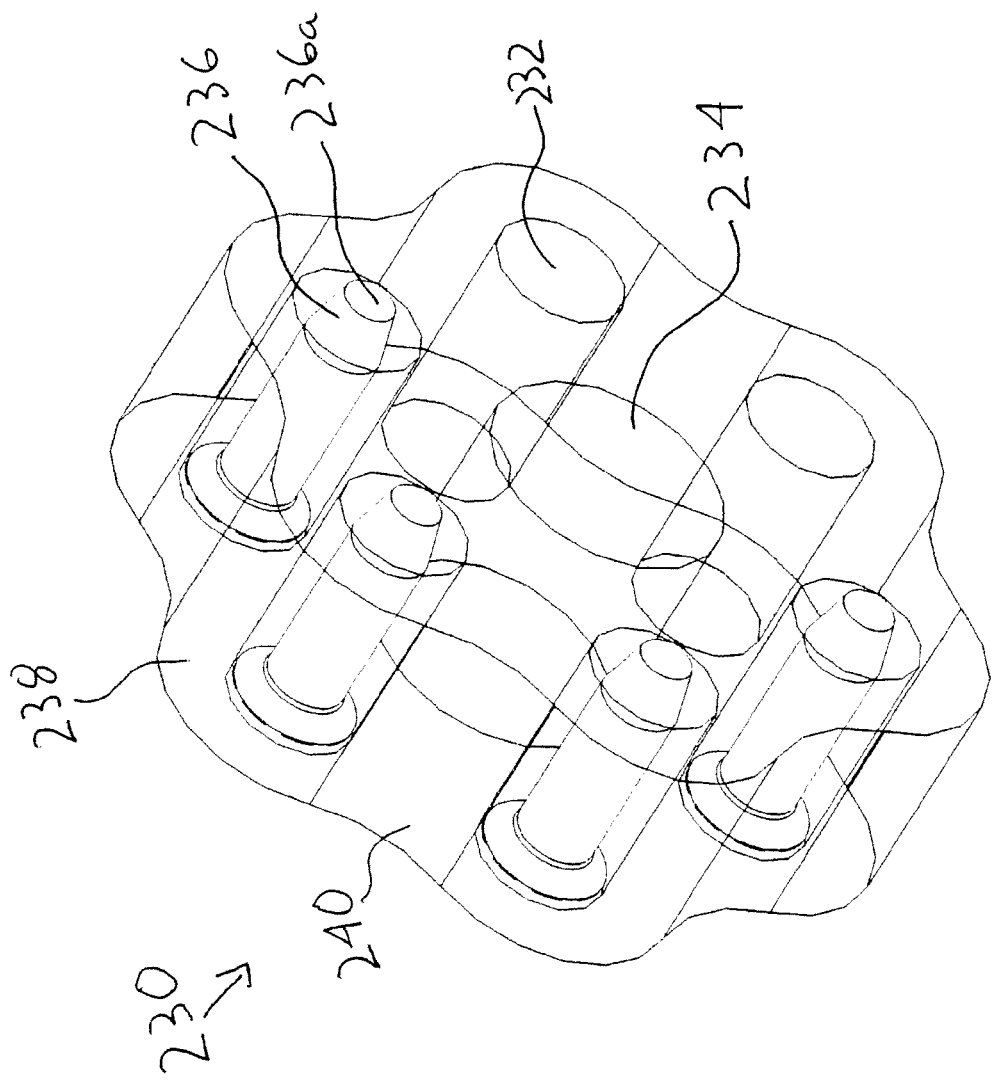
FIGS. 38A, B, and C are perspective, front, and side views respectively of a transparent cartridge holding fasteners.
Figure 38B:
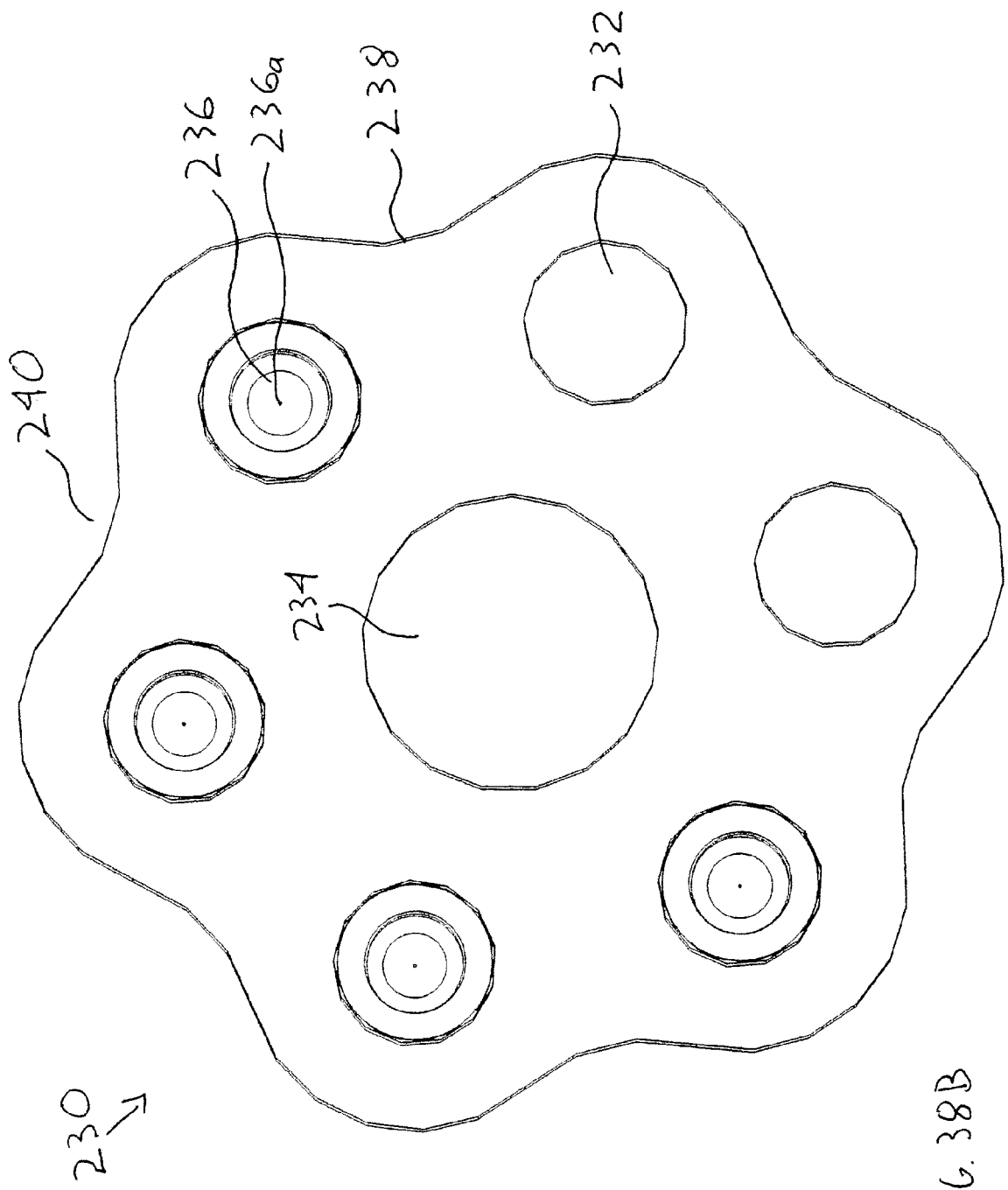
Figure 38C:
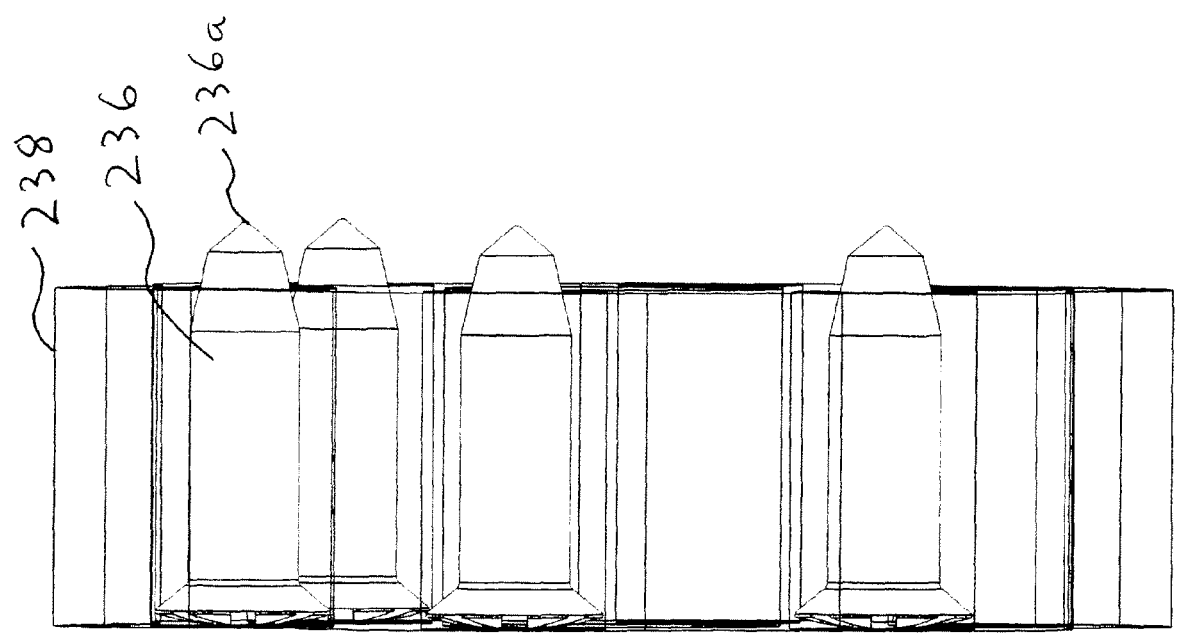

FIG. 38A, FIG. 38B, and FIG. 38C show perspective, front, and cross-sectional side views of another embodiment of a transparent cartridge incorporating features of the present invention. The cartridge 230, a six-chamber cartridge, comprises axial hole 234, chambers 232, and notches 240. The axial hole 234 is in the center of a symmetric cartridge 230. In this embodiment, the number of chambers 232 and notches 240 is equal, namely six of each. However, in other embodiments the number of chambers and cartridges can be unequal. The chambers 232 are arranged in a circle. The circumferential surface 238 of cartridge 230, including the surfaces of notches 240, is substantially smooth. In other embodiments the circumference of the cartridge can be smooth, angular, or a combination of the two. Also shown in FIG. 38A, FIG. 38B, and FIG. 38C are multiple fasteners 236, each in their own chamber 232. Not shown in FIG. 38 is an alignment system, which can either be integral to the fastener 236, integral to the walls 232*a* of chambers 232, separate element attached to either the fastener 236 or the chambers 232, or a combination thereof. Different embodiments of alignment systems are discussed below. Cartridge 230, as shown, can be substantially transparent to provide the operator views of chamber 232 and prevent line of sight problems during operation. In FIG. 38A, FIG. 38B, and FIG. 38C, sections of the fasteners 236 extend outside and forward of the chambers 232. In other embodiments, the ends 236*a* of the fasteners 236 can be flush with the end of the chambers 232, or can be completely within the chambers 232, not reaching the end of the chambers 232.

Figure 39A:
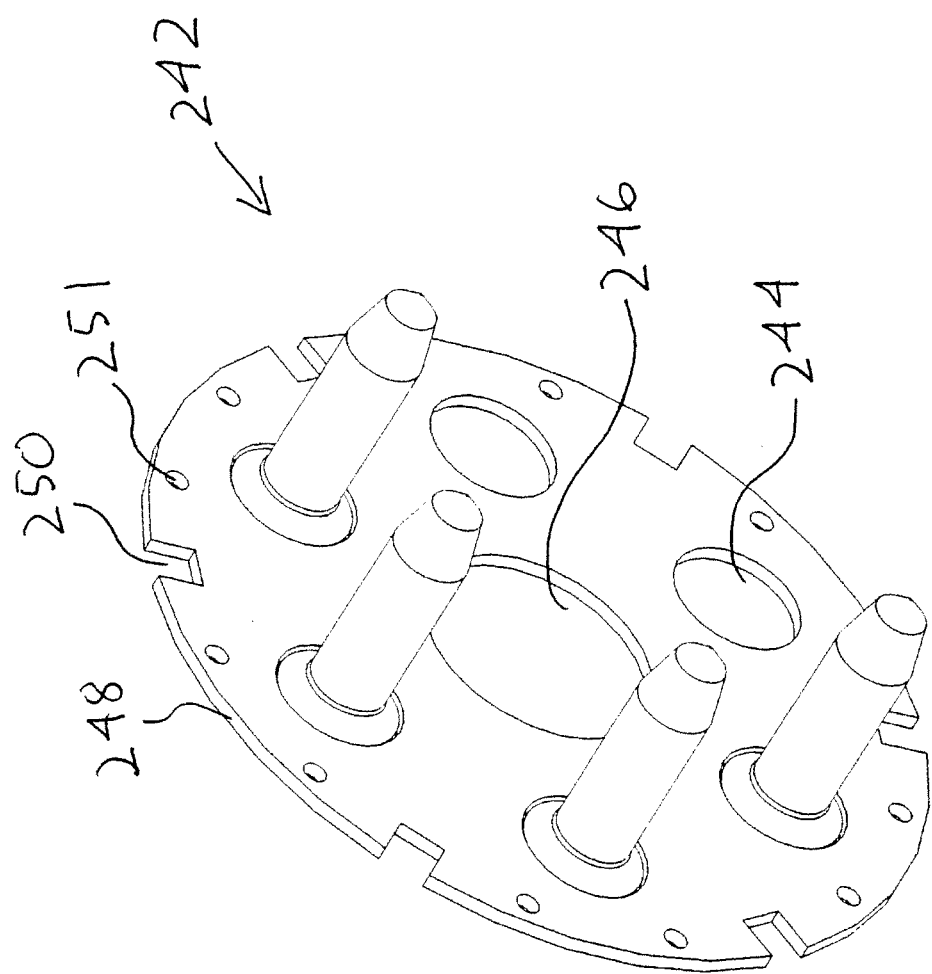
FIGS. 39A, B, and C are perspective, front, and side views respectively of another cartridge holding fasteners.
Figure 39B:
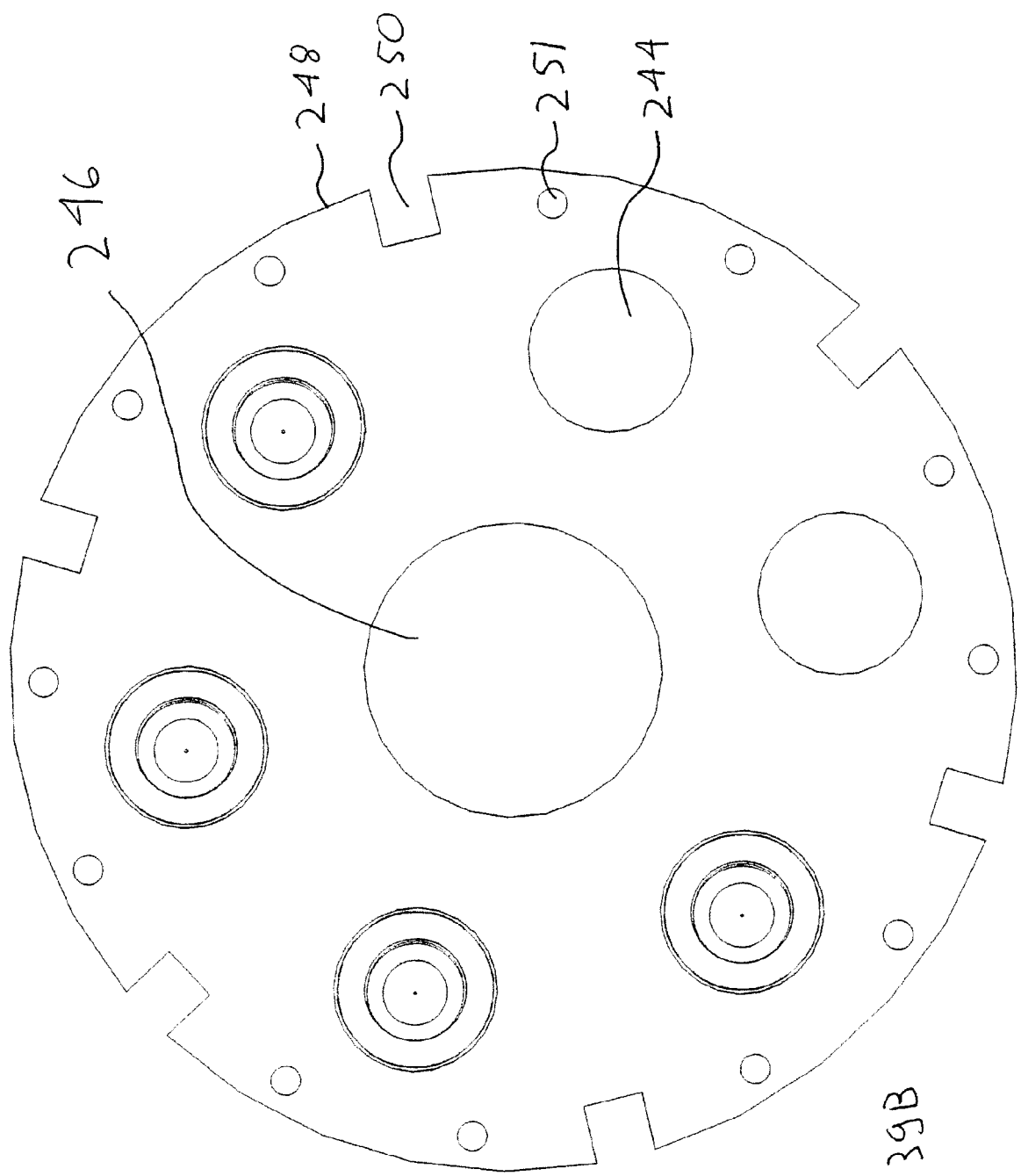

FIG. 39A, FIG. 39B, and FIG. 39C show perspective, front, and side views of another embodiment of a cartridge 242 according to the present invention. The cartridge 242 is thin so as to be substantially disc-shaped. Cartridge 242 comprises an axial hole 246, chambers 244 and notches 250. The chambers 244 are arranged in a circle with the axial hole 246 at its center. The circumferential surface 248, unlike 238, contains angular surfaces forming notches 250. The holes 251 can be used for purposes such as indexing.

Figure 40C:
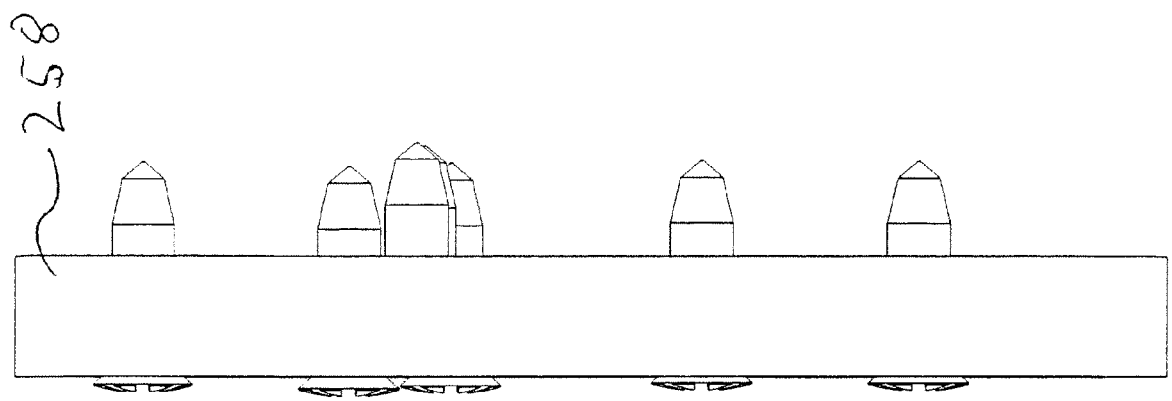
FIGS. 40A, B, and C are perspective, front, and side views respectively of yet another cartridge holding fasteners.

FIG. 40A, FIG. 40B, and FIG. 40C show perspective, front, and side views of a third cartridge embodiment according to the present invention. While cartridge 252 comprises axial hole 256 and chambers 254, it does not include notches. Instead, the cartridge 252 controls its rotation by another method, such as a separate element applying friction to the outside of the cartridge 252, indexing holes such as shown in FIG. 39B, or precisely designing the indexing mechanism to rotate exactly the correct amount. The chambers 254 are arranged in a spiral. This arrangement can increase the overall number of fasteners that a cartridge can carry. Cartridge 252, for instance, comprises ten chambers 254. Axial hole 256 is not at the center of cartridge 252 so as to enable a non-circular chamber rotation such that each successive chamber 254 and fastener 255 will be correctly placed in front of the driver.

Figure 41A:
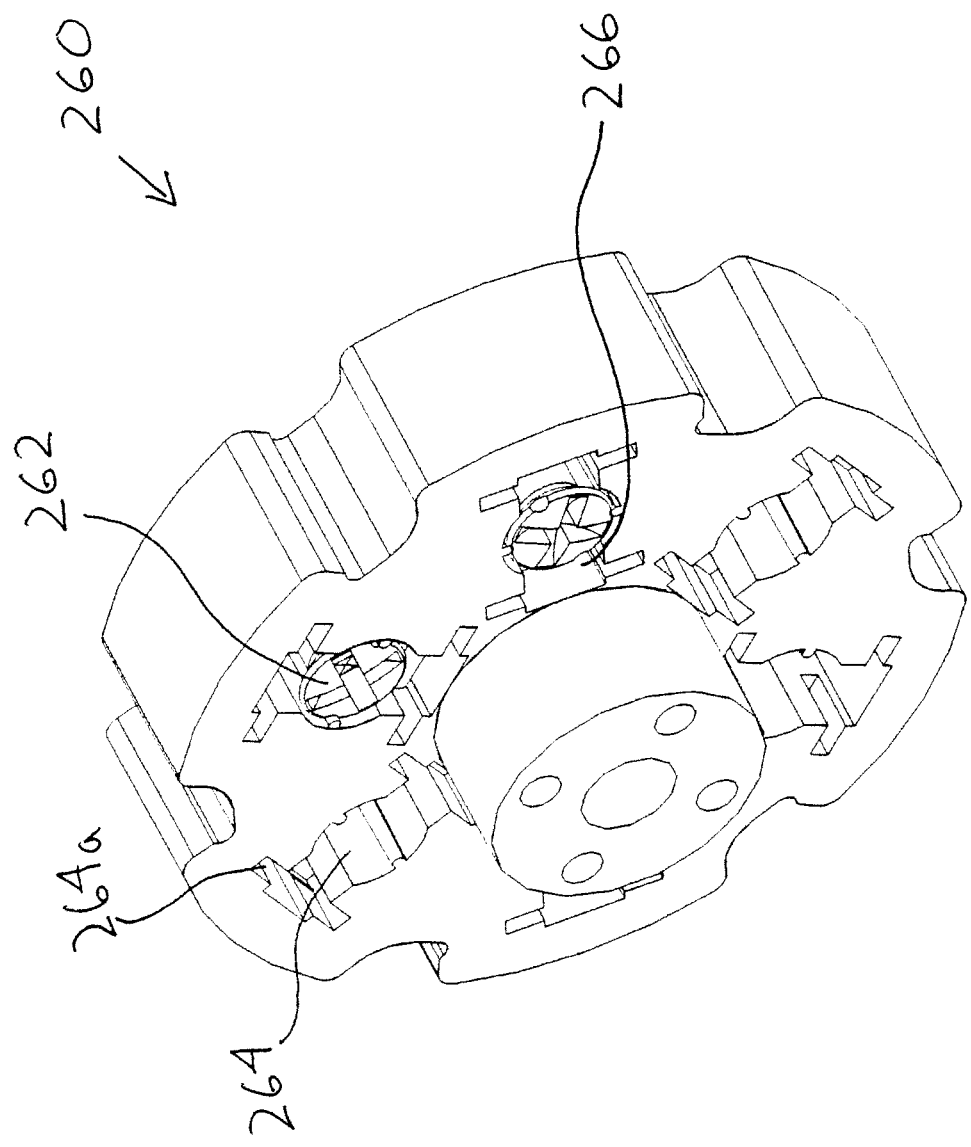
FIGS. 41A, B, and C are perspective, rear, and side views respectively of a cartridge comprising cantilever holders.
Figure 41B:
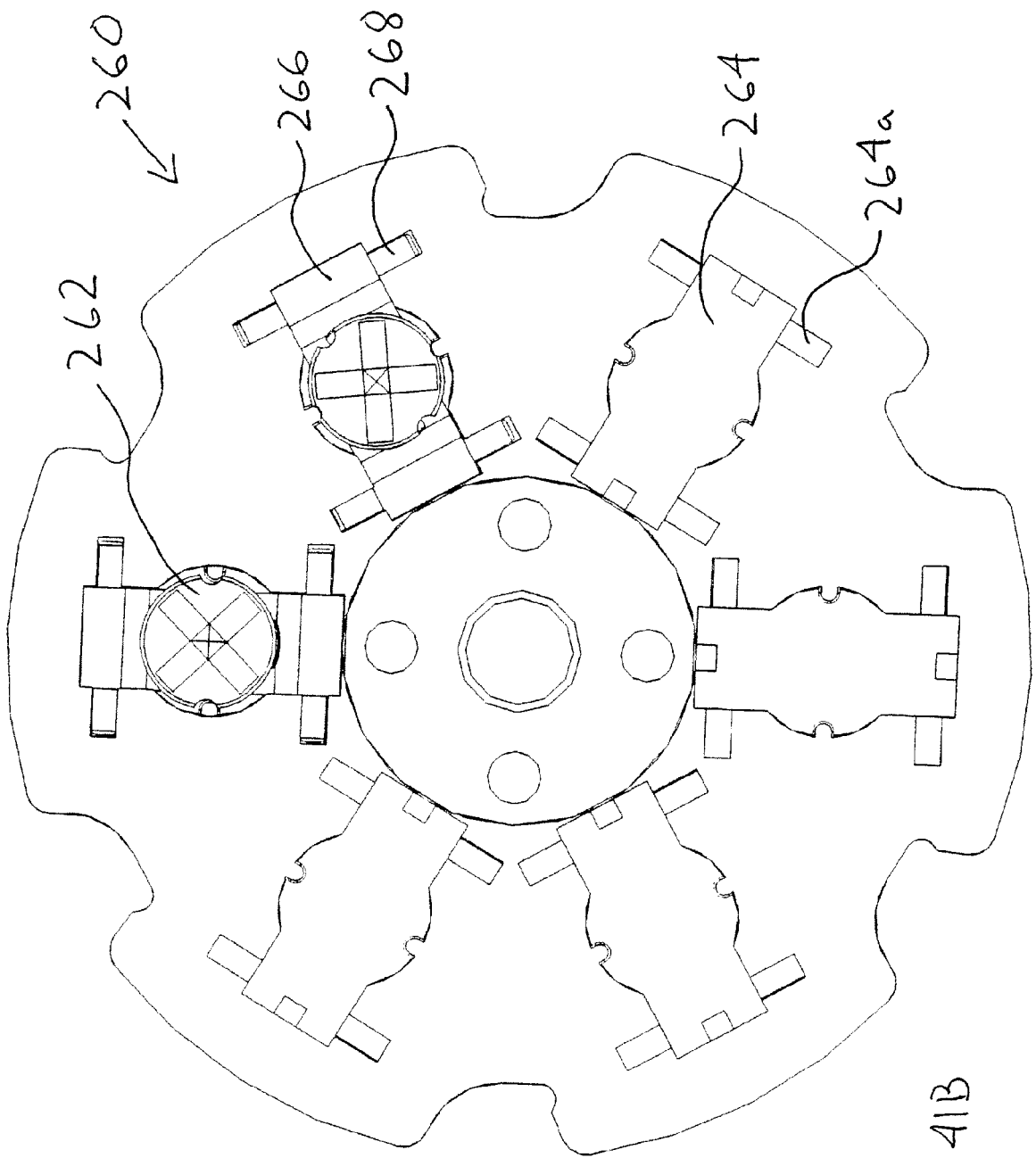
Figure 41C:
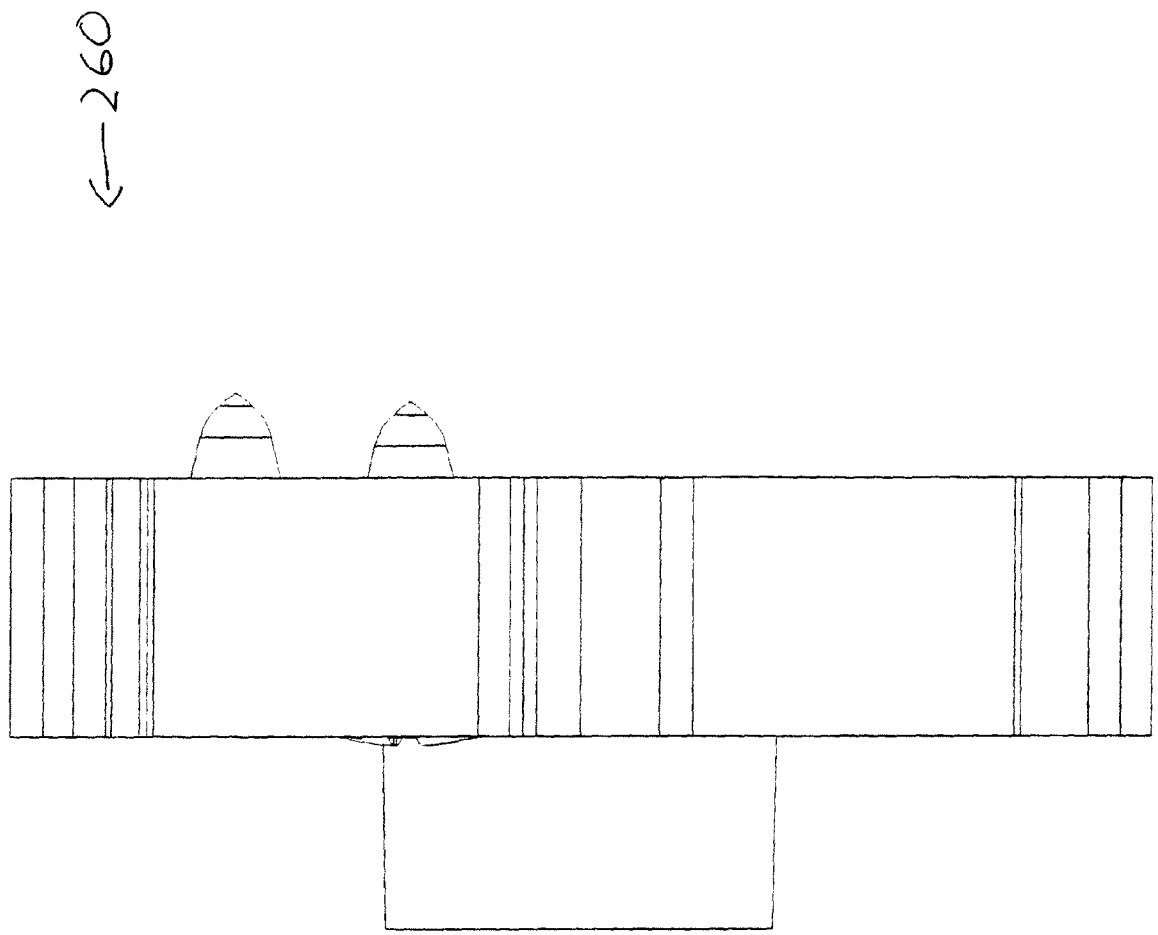

FIG. 41A, FIG. 41B, and FIG. 41C show perspective, rear, and side views, respectively, of a cartridge 260. The cartridge 260 comprises an alignment system to hold fasteners 262 in each chamber 264. In this embodiment, the alignment system comprises cantilever holders 266 which themselves comprise springs (not shown) which hold the fasteners 262 within the chambers 264. The cantilever holders 266 in this embodiment are attached to the cartridge 260 at channels 264*a*, within the inner wall of the chamber 264. The cantilever holders 266 also have a hole which is filled by a post 264*b*, also on the inner wall of the chamber 264. Other embodiments can comprise some, but not all, of these attachment features, or all of these attachment means as well as other attachment features.

Figure 42:
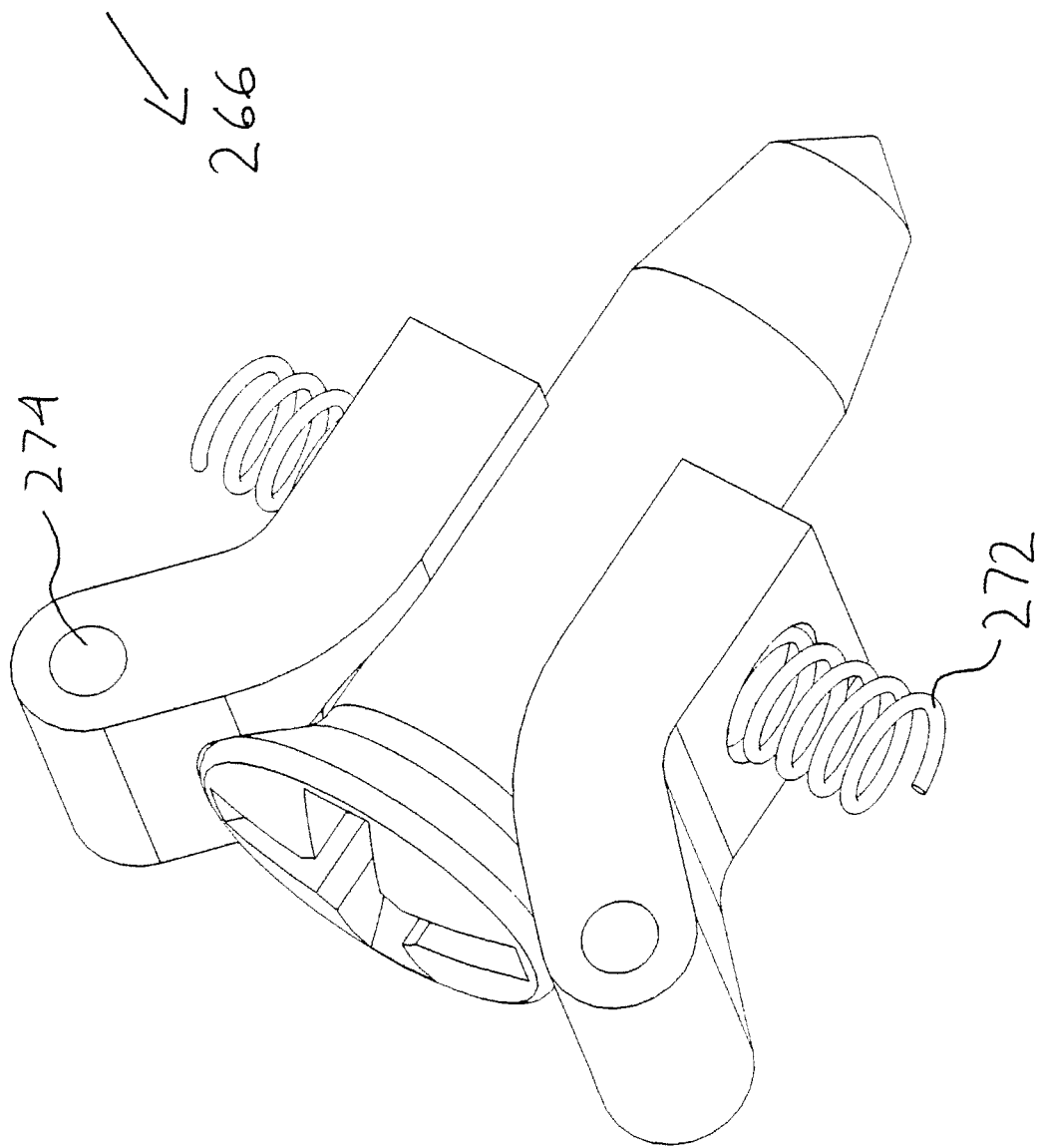
FIG. 42 is a perspective view respectively of cantilever holders.

FIG. 42 shows a perspective view of cantilever holders 266. The cantilever holders 266 comprise holes 274 to enable connection to extensions on the inner wall of a chamber. The cantilever holders 266 also comprise springs 272. FIG. 43A shows a perspective cross-sectional view of a cartridge 260. The springs 272 (not shown) attach to the inner wall feature 264*c* and fill the recess 266*a* within each cantilever holder. The springs push the cantilever holders 266 inward such that they grasp the fasteners 276 and hold them stable within the chambers 264. FIG. 43B shows a cross-sectional view of a housing wherein the driver tip (not shown) has engaged the fastener head 276 and pushed the fastener 268 out of the chamber 264. The springs are compressed and the cantilevers rotate outwards until they hit inner wall features 238*c*, enabling the fastener 268 to exit the chamber 264. In reusable embodiments, the cantilever holders will rebound to their initial position such that they can again hold fasteners. In disposable embodiments the cantilever holders are rendered unable to hold new fasteners, such as through the use of a one-use spring or by otherwise preventing the cantilever holder from returning to its original position.

In other embodiments, the cantilever holders 266 can be attached to the inner wall of chamber 238 with an adhesive or with a press-fit design and process. In other embodiments, the cantilever holders 266 can be attached to the fastener 268 before the fastener is inserted into the chamber 264. In such an embodiment, the inner wall of the chamber 264 comprises strictures to which the cantilever holder attaches. When a fastener 268 is engaged by the driver tip and pushed out of the chamber 268, the structures of the inner wall of the chamber 264 hold the cantilever holders 266 such that they remain within the chamber 264, and thus contamination of the surgical site is prevented.

Cartridge 260 also comprises an axial raised portion 278 and shaft head chambers 280 centered about the axial hole. The main axial drive shaft head can engage these holes to rotate the cartridge 260.

Figure 44A:
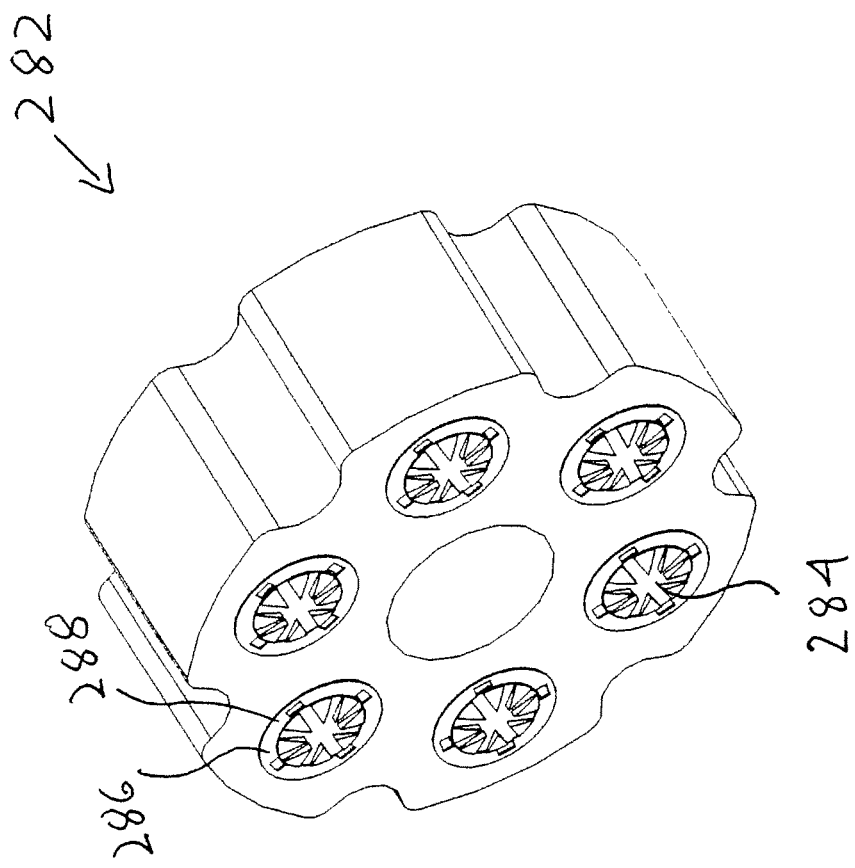
FIGS. 44A, B, and C are perspective, rear, and side views respectively of a cartridge comprising spring clips.

FIG. 44A, FIG. 44B, and FIG. 44C show front, rear, and side views of a cartridge 282 comprising another alignment system to hold fasteners 284 in each chamber. In this embodiment, the alignment system comprises spring clips 286 which themselves comprise a top portion 288 securing or surrounding the top portion of the cartridge 282. In an alternative of this embodiment spring clips 286 can be attached to the inner walls of the chambers.

Figure 45B:
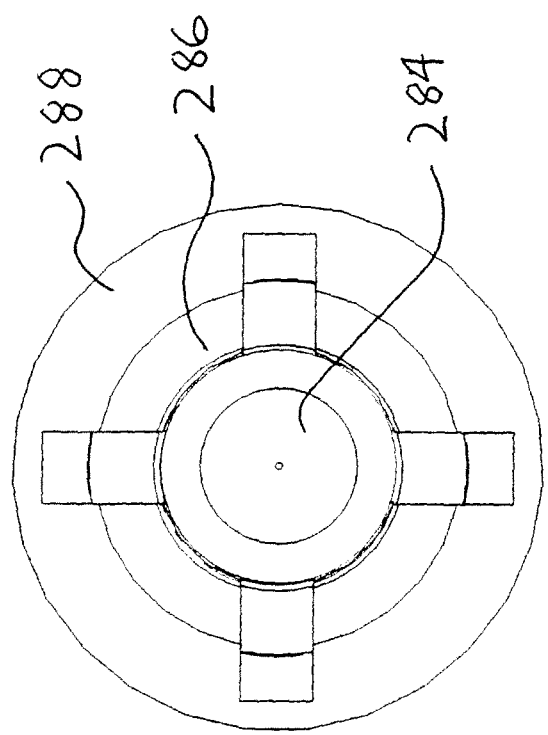
FIGS. 45A, B, and C are perspective, front, and side views respectively of a fastener held by a spring clip.
Figure 45C:
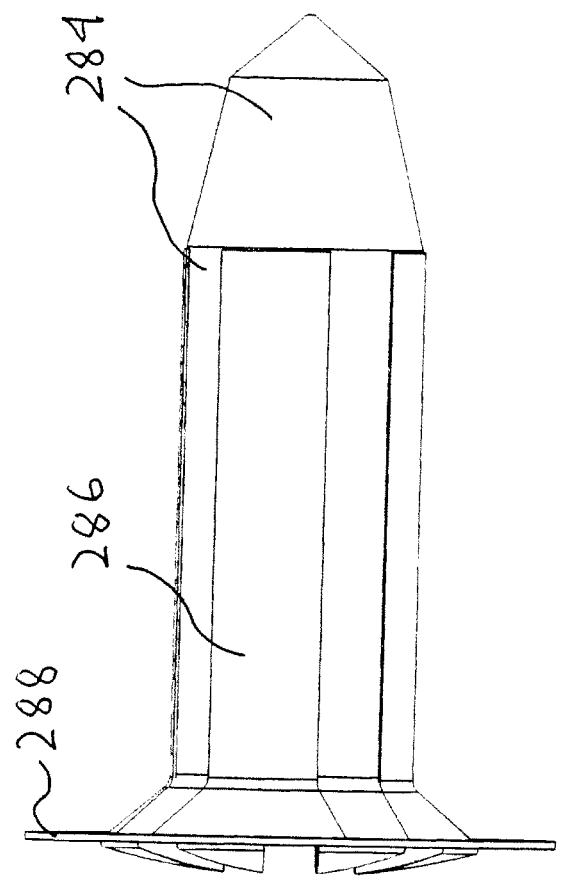
Figure 46A:
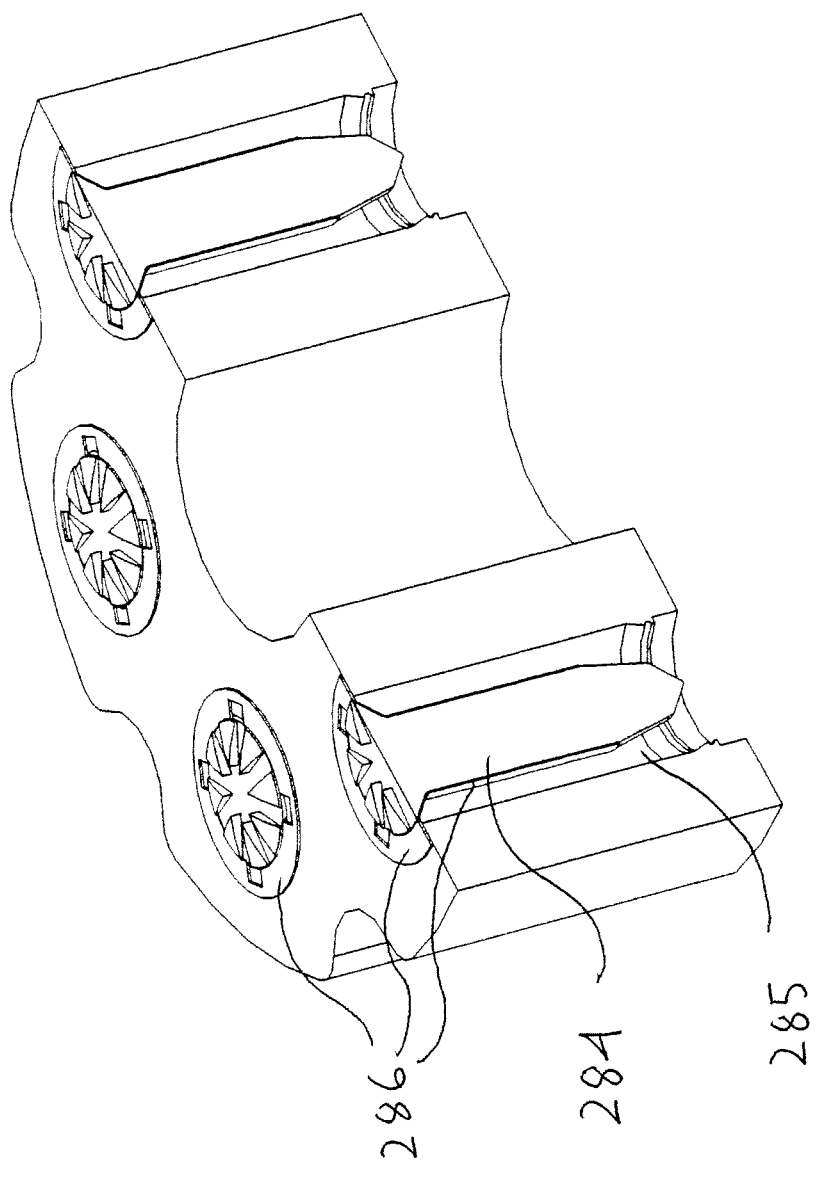
FIGS. 46A and B are cross-sectional perspectively and side views respectively of a cartridge comprising a fastener and a spring clip.
Figure 46B:
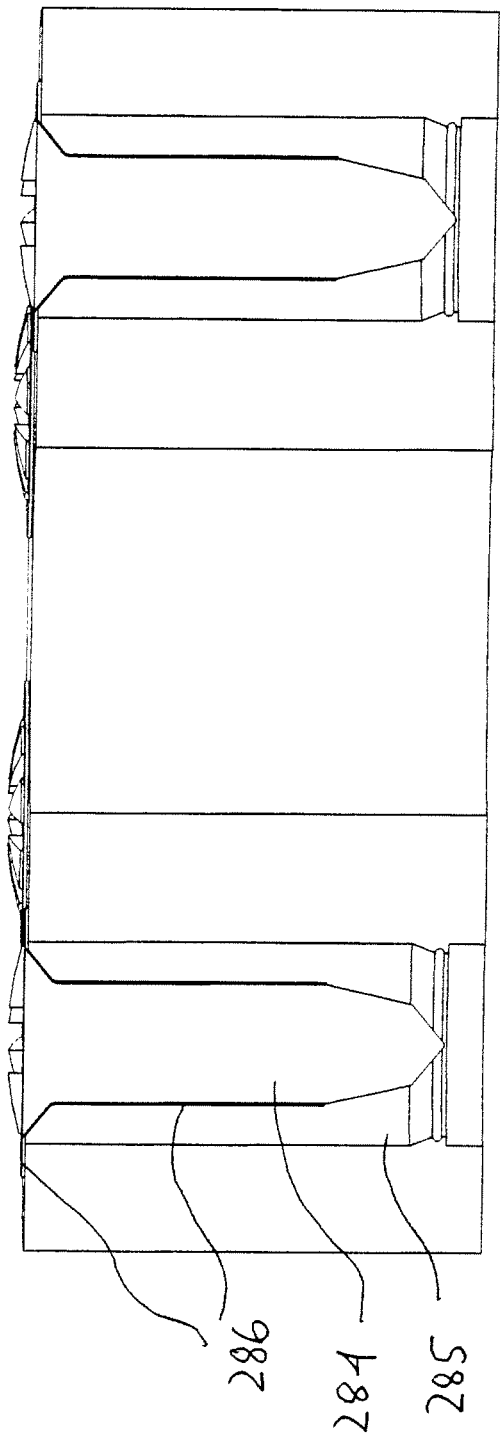

FIG. 45A, FIG. 45B, and FIG. 45C show perspective, top, and side views, respectively, of a spring clip 286 and a fastener 284. FIG. 46A and FIG. 46B show cross-sectional perspective and side views of fastener 284 and spring clip 286 within chamber 285. The tension applied by spring clip 286 can hold fastener 284 in the necessary alignment to be engaged by the driver tip. The spring clips 286 have enough flexibility such that once the driver tip engages the fastener 284 it can push the fastener 284 through and out of the chamber 285. The spring clip 286 can be designed to spring back to its initial position such that the chamber 285 can be reloaded with another fastener 284. In a disposable embodiment of the invention, the spring clip 286 can be designed to remain pushed against the inner wall 285a after the fastener 284 has exited chamber 285 such that it will no longer be able to retain a new fastener.

Figure 47B:
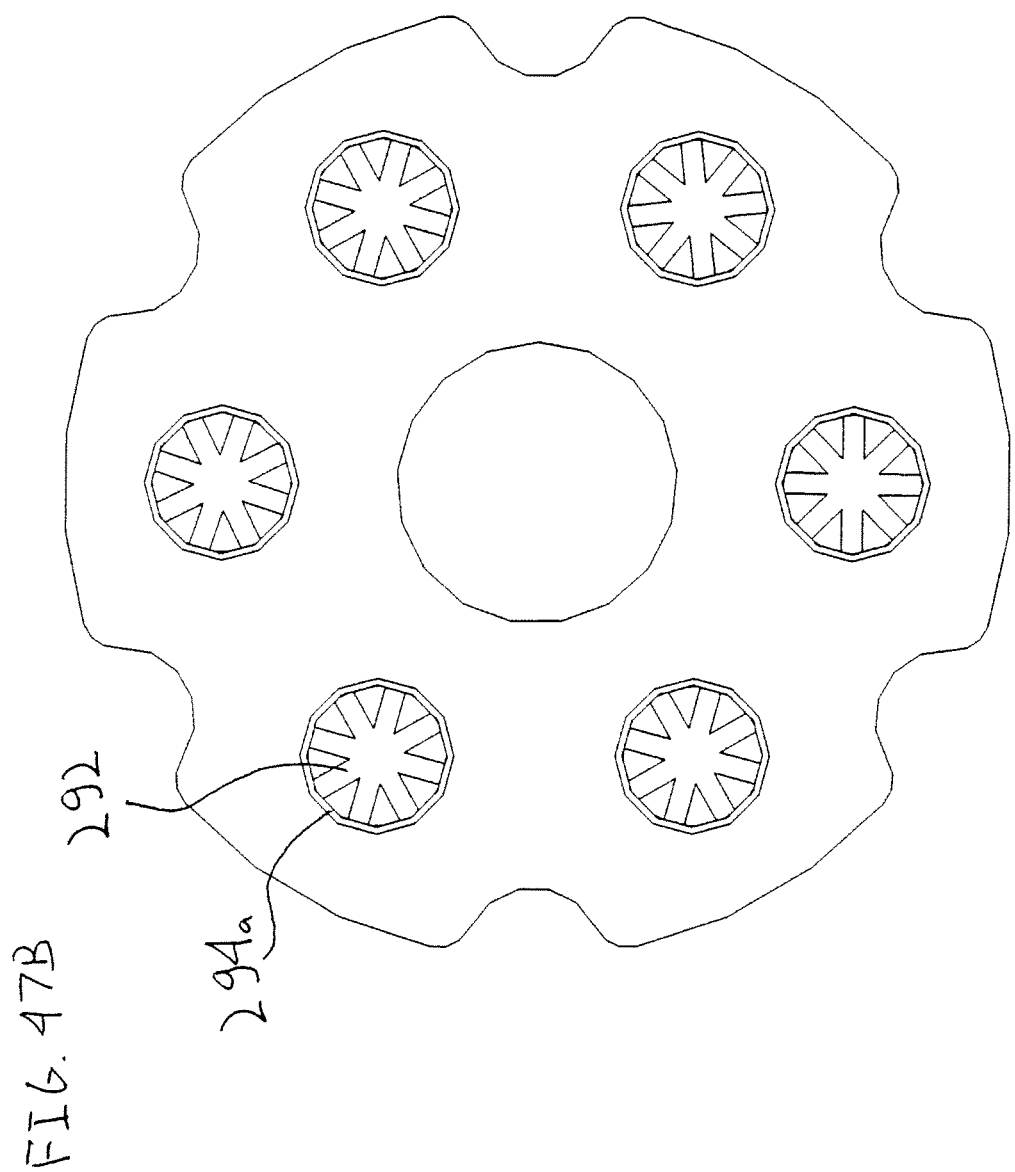
FIGS. 47A, B, and C are perspective, rear, and side views respectively of a cartridge comprising molded features to hold fasteners.
Figure 47C:
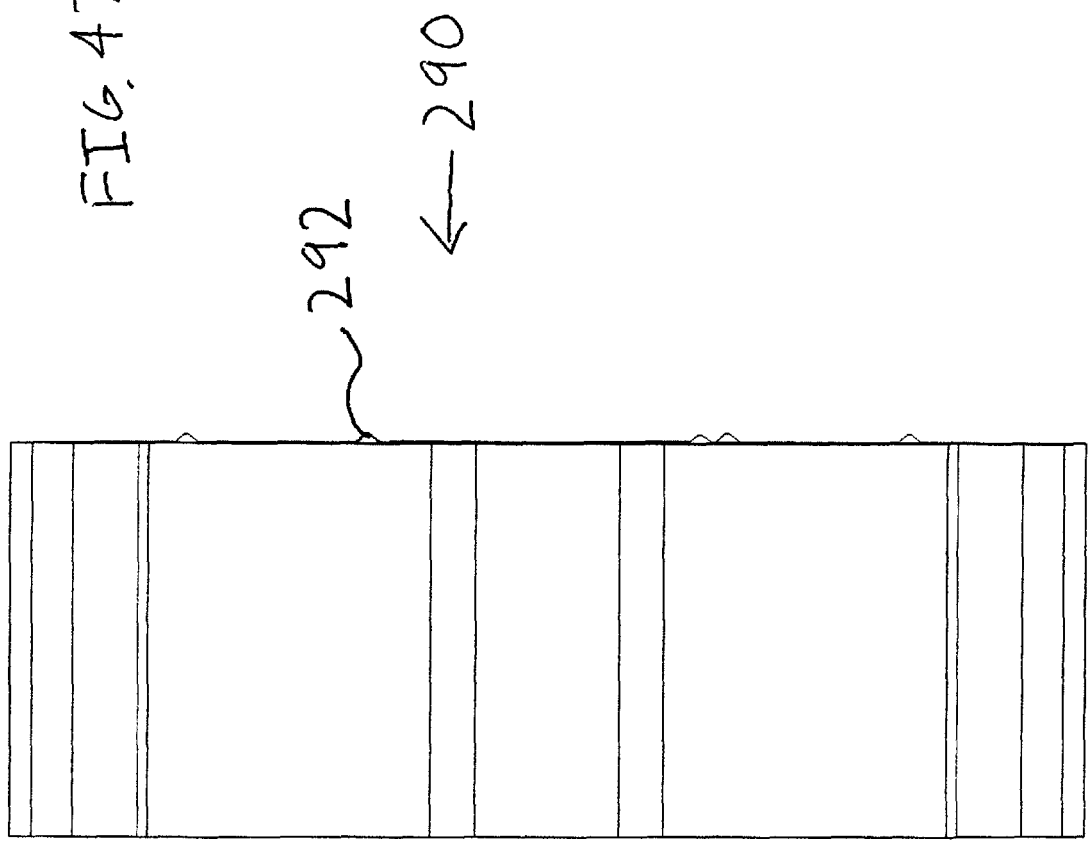

FIG. 47A, FIG. 47B, and FIG. 47C show perspective, rear, and side views, respectively, of cartridge 290 comprising fasteners 292 molded within chambers 294. FIG. 48A and FIG. 48B show cross-sectional perspective and side views of cartridge 290. As can be seen in FIG. 48A and FIG. 48B, the inner wall of chamber 294 comprises ring 294a which holds the fastener 292 in alignment within chamber 294. When the driver tip engages fastener 292, the fastener breaks free from ring 294a in order to travel through the chamber 294. Ring 294a is designed such that no debris can travel into the surgical site. Further, ring 294a can be designed such that the cartridge is either reusable or disposable. In reusable embodiments, ring 294a is manufactured in such a way so as to rebound to its original form after fastener 292 exits the chamber 294. These reusable embodiments can comprise o-rings, rubber wall features, or other features that will enable the chamber 294 to again hold a fastener 292. In disposable embodiments, features 294a are manufactured such that after fasteners 292 exit past features 294a, the features do not regain their original shape and thus cannot again hold fasteners 292 in the necessary alignment. While in the FIG. 48A, FIG. 48B, and FIG. 48C embodiment the features are attached to the side walls of the chamber, in other embodiments the features can be included with and attached to the fasteners.

FIGS. 49A through 51B show different embodiments in which driver tip 302 engages fastener head 300. In preferred embodiments, a fastener can be held securely by driver tip 302 so as to be securely aligned while in transit from the chamber to the surgical site. While the below embodiments show attachment systems wherein the driver tip is attached to the inside of the fastener head, other embodiments where the driver tip attaches to the periphery of the screw head are also possible.

Figure 49B:
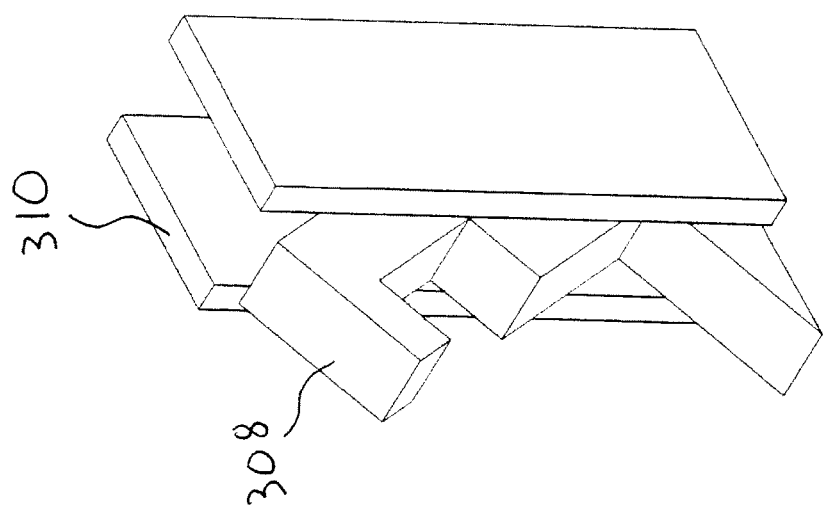
FIG. 49B is a perspective view of a latching component present in the head of the fastener.

FIG. 49A shows a perspective view of a fastener head 300 engaged by driver tip 302. In this embodiment, the attachment system comprises holes 304 and recesses 306 to house attachment hooks 308 and hook casings 310. Attachment hooks 308 are shown in detail in FIG. 49B. FIG. 49C shows a cross-sectional view of the attachment system within the head of a fastener. In this embodiment, the attachment hooks 308 are held in recesses 306. Surrounding the attachment hooks 308 are hook casings 310, attached to the hooks 308 at pivot points 310a. In other embodiments, attachment hooks can be attached directly to the fastener heads. As driver tip 302 slides into holes 304, the edge of the driver tip is engaged by the bottom section of attachment hooks 308. The attachment hooks 308 then rotate about pivot point 310a until the top section of the attachment hooks 308 engage circumferential ridges 312 of driver tip 302. This attachment system holds the fastener head 300 securely in alignment while the fastener is transported from the chamber to the surgical site. Upon deposition of the fastener into the surgical site and the cessation of the forward/inward movement of the driver tip 302, the force to keep the fastener within the surgical site is greater than the attachment force between driver tip 302 and fastener head 300, thus allowing the driver tip 300 to withdraw from the surgical site while leaving the fastener in place.

FIG. 50 shows a perspective view of an attachment system similar to that of FIG. 49. However, in the FIG. 50 embodiment, attachment hooks 308 are present in only one hole 304. While this embodiment comprises three recesses 306 in each hole 304, more or fewer recesses are possible in other embodiments. Further, while in this embodiment all three recesses 306 of hole 304a house attachment hooks 308, embodiments where less than all of the recesses house attachment hooks are also possible.

FIG. 51A and FIG. 51B show perspective and cross-sectional views, respectively, of another embodiment of an attachment system. In this embodiment, attachment hooks 314 are flexible pieces, preferably molded pieces, as opposed to rotational hooks 308. Attachment hooks 314 can be formed as part of screw head 300 or formed separately and then attached inside holes 304. Attachment hooks 314 work in a substantially similar manner to attachment hooks 308. Further, attachment hooks 314 can be manufactured to ensure that there is no breakage of molded attachment hooks 314 so as to prevent contamination of the surgical site.

Figure 52A:
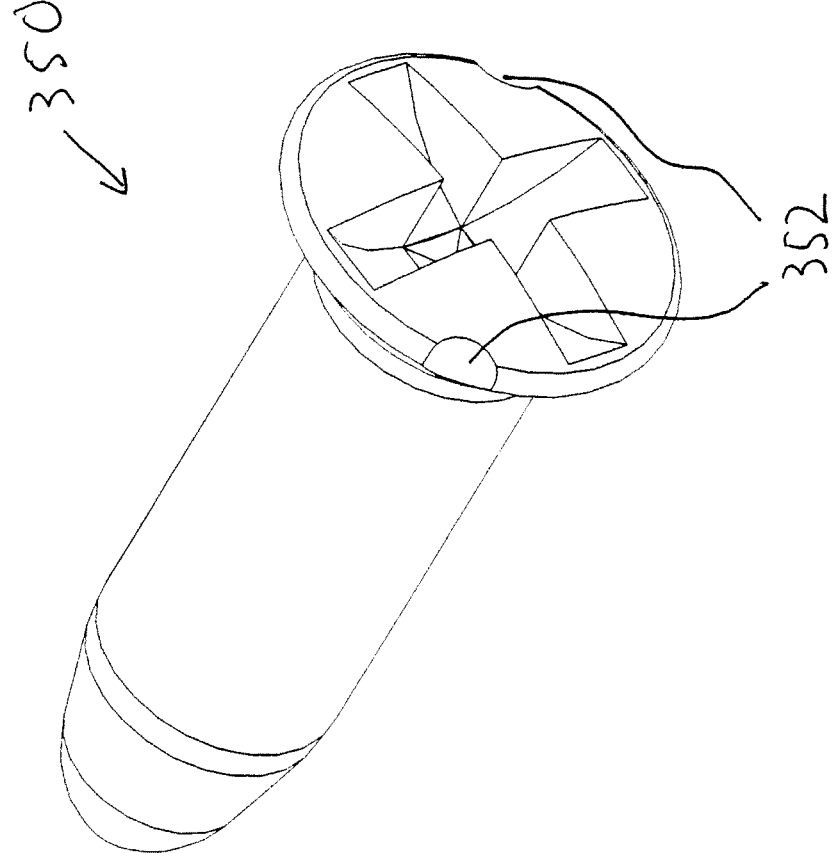
FIGS. 52A, B, and C are perspective, front, and side views respectively of a fastener comprising alignment features.
Figure 52B:
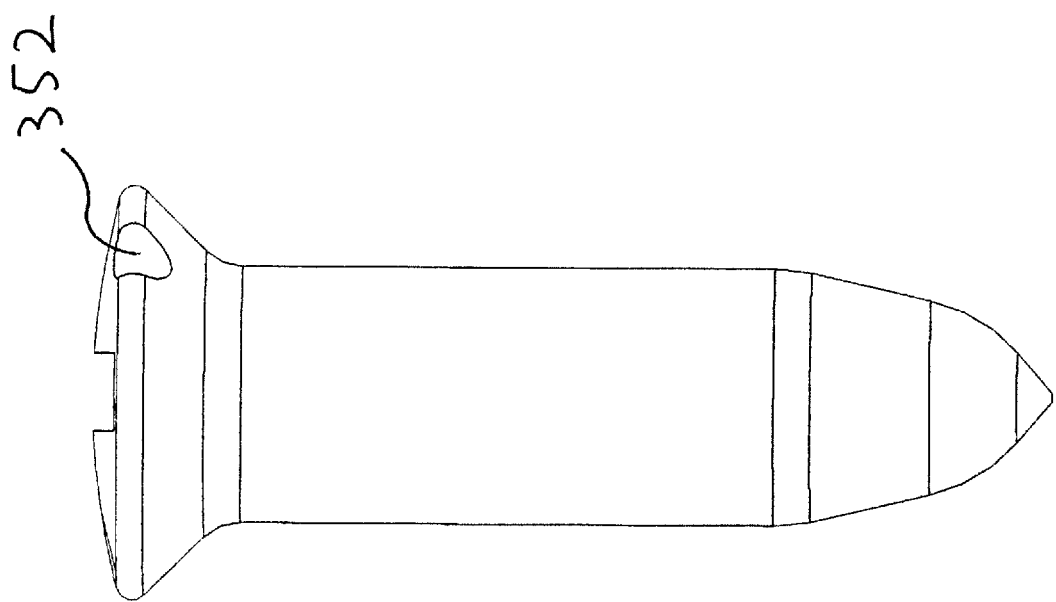

FIG. 52A, FIG. 52B, and FIG. 52C show perspective, rear, and side views of a fastener 350 comprising screw positioning features 352. In this case, screw positioning features 352 comprise notches. Each notch 352 may be used to orient the fastener within the chamber in a particular rotational alignment so that the drive blade engages the screw head at precisely the right rotational angle.

Figure 53A:
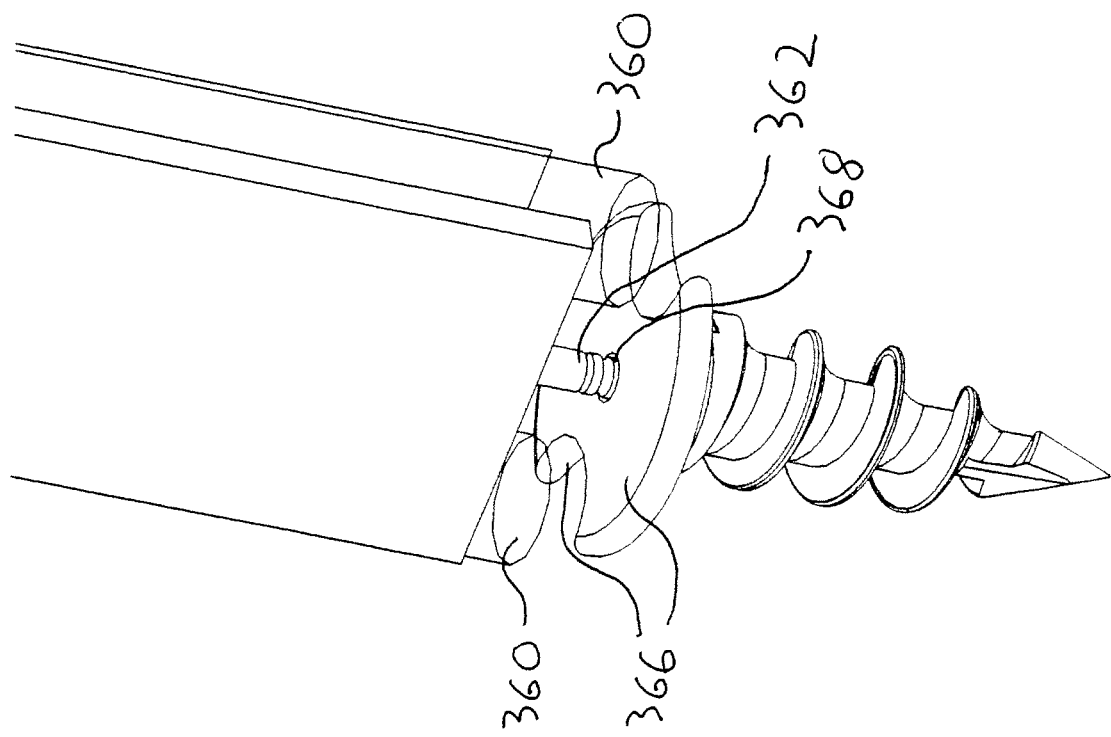
FIGS. 53A and B are perspective and side views respectively of a fastener system comprising peripheral driver tips and a guide pin.

FIG. 53A and FIG. 53B show perspective and side views of a fastener system comprising a driver tip with two peripheral prongs 360. In this case the prongs are transparent, but in other embodiments they are not transparent. These prongs engage the outer rim of the head 366 of fastener 364. Fastener head 366 comprises notches where the prongs 360 engage; other rim features are also possible. The prongs 360 both secure the fastener 364 and provide rotational torque. The fastener system also comprises a guide pin 362. In this case guide pin 362 is an axial guide pin. The pin engages a hole 368 on the fastener head 366. The pin 362 can correct any slight misalignment of prongs 360.

FIG. 54A and FIG. 54B show a perspective and side cross-sectional view, respectively, of a chamber comprising another embodiment of a cantilever system similar to that of FIG. 41A and FIG. 43A. In this case, the cantilevers 267 comprise leaf springs 273. The two opposing leaf springs are rigidly attached to the inner wall of chamber 264 and the side of cantilever body.

To use the cartridge of the placement system 200 described above, a loaded cartridge is slid into the lower wall placement system 200. A first fastener is positioned to receive the driver. The trigger 208 is manually operated, which causes power from battery 56 to be delivered to the motor 57, causing the driver tip to move forward toward the fastener head. Continued forward movement causes the driver tip to enter the head of the fastener and interlock therewith and to rotate the fastener. The driver tip, with the rotating fastener attached thereto, now extends through the end of the placement system 200 and the rotating fastener can be applied to the bone surface or tissue for securing the bone pieces and/or tissue together. Releasing the trigger 208 allows a spring to exert rearward motion on the driver tip. As the trigger 208 moves back to its resting position, structures interact with the cartridge causing the cartridge to rotate and position the next fastener in front of the driver tip so that the above described action can be repeated. In other embodiments, structures interact with the cartridge causing the cartridge to rotate during the initial manual operation of the trigger 208, causing the cartridge to position the next fastener as the driver tip moves forward.

I claim:

1. A device for automatically feeding a series of medical fasteners to a location for mating with a rotary driver tip and for placement of each of said series of medical fasteners into tissue or bone structure to hold said tissue or bone structure together, comprising:
    a driver body,
    a powered screw driver positioned within said driver body; said screw driver having a tip, the screw driver configured for lateral and rotational movement;
    a fastener carrier system comprising a cartridge having multiple chambers, each chamber carrying a fastener therein, removable from and attached to said driver body; and
    a positioning mechanism within the driver for advancing the cartridge to position a fastener of the series of medical fasteners in the chambers of the cartridge in a controlled manner to receive the tip of the screw driver, to interlock the tip to structure on or in the head of the fastener, to rotate the fastener, and to move the interlocking tip and fastener laterally forward for placement of the fastener.

2. The device of claim 1, further comprising structure for translating linear motion into rotational motion to rotate said rotatable multi-chamber cartridge.

3. The device of claim 2, wherein said rotatable multi-chamber cartridge rotates during a forward movement of said screw driver tip such that an individual fastener is in position to receive said screw driver tip.

4. The device of claim 1, further comprising a structure for temporarily and removably holding a fastener within each chamber.

5. The device of claim 4, wherein said structure for temporarily and removably holding said fasteners is reusable to receive and hold further fasteners.

6. The device of claim 4, wherein said structure for temporarily and removably holding a first fastener therein cannot hold a second fastener after the removal of said first fastener.

7. The device of claim 4, wherein said structure for temporarily and removably holding a first fastener comprises at least one cantilever system attached to the inner wall of at least one chamber.

8. The device of claim 7, wherein said at least one cantilever system comprises a cantilever and a spring.

9. The device of claim 8, wherein said spring is a leaf spring.

10. The device of claim 4, wherein said structure for temporarily and removably holding a first fastener comprises at least one spring clip.

11. The device of claim 10, wherein said spring clip is attached to the outer surface of said cartridge.

12. The device of claim 4, wherein said structure for temporarily and removably holding a first fastener comprises at least a molded extension between a fastener and an inner wall of a corresponding chamber.

13. The device of claim 12, wherein said molded extension is attached to the inner wall of said corresponding chamber.

14. The device of claim 12, wherein said molded extension is attached to said fastener.

15. The device of claim 1, wherein said individual fasteners comprise a rotation alignment structure to position said individual fasteners to receive said screw driver tip.

16. The device of claim 1, wherein said individual fasteners comprise a structure for attachment of the fastener to said screw driver tip.

17. The device of claim 16, wherein said attachment structure comprises rotatable hooks.

18. The device of claim 1, further comprising a guide pin.

19. The device of claim 18, wherein said screw driver tip attaches to the periphery of said fastener.

* * * * *